US011866479B2

(12) United States Patent
Carrillo Molina et al.

(10) Patent No.: US 11,866,479 B2
(45) Date of Patent: Jan. 9, 2024

(54) HIV ANTIBODY DERIVATIVES WITH DUAL ANTIVIRAL AND IMMUNOMODULATORY ACTIVITIES FROM CD4 AND GP41

(71) Applicant: AlbaJuna Therapeutics, S.L., Badalona (ES)

(72) Inventors: Jorge Carrillo Molina, Badalona (ES); Bonaventura Clotet Sala, Badalona (ES); Julian M. Blanco Arbues, Badalona (ES)

(73) Assignee: FUNDACIÓ PRIVADA INSTITUTE DE RECERA DE LA SIDA-CAIXA, Badalona (ES)

( * ) Notice: Subject to any disclaimer, the term of this patent is extended or adjusted under 35 U.S.C. 154(b) by 871 days.

(21) Appl. No.: 15/777,666

(22) PCT Filed: Nov. 19, 2016

(86) PCT No.: PCT/IB2016/001868
§ 371 (c)(1),
(2) Date: Oct. 22, 2019

(87) PCT Pub. No.: WO2017/085563
PCT Pub. Date: May 26, 2017

(65) Prior Publication Data
US 2021/0238252 A1 Aug. 5, 2021

(51) Int. Cl.
*C07K 19/00* (2006.01)
*C07K 14/705* (2006.01)
*C07K 14/005* (2006.01)
*A61P 31/18* (2006.01)
*G01N 33/569* (2006.01)
*C07K 14/73* (2006.01)
*A61K 38/16* (2006.01)
*A61K 38/17* (2006.01)
*C07K 14/715* (2006.01)
*A61K 45/06* (2006.01)

(52) U.S. Cl.
CPC ...... *C07K 14/70514* (2013.01); *A61K 38/162* (2013.01); *A61K 38/1774* (2013.01); *A61K 38/1793* (2013.01); *A61P 31/18* (2018.01); *C07K 14/005* (2013.01); *C07K 14/7158* (2013.01); *C07K 19/00* (2013.01); *G01N 33/56988* (2013.01); *A61K 45/06* (2013.01); *C07K 2319/30* (2013.01); *C12N 2740/16022* (2013.01); *C12N 2740/16033* (2013.01); *G01N 2333/16* (2013.01)

(58) Field of Classification Search
CPC  C07K 14/70514; C07K 14/005; C07K 19/00; A61P 31/18; G01N 33/56988
See application file for complete search history.

(56) References Cited

U.S. PATENT DOCUMENTS

| | | |
|---|---|---|
| 4,179,337 A | 12/1979 | Davis et al. |
| 4,439,196 A | 3/1984 | Higuchi |
| 4,447,224 A | 5/1984 | Decant et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,495,285 A | 1/1985 | Shimizu et al. |
| 4,522,811 A | 6/1985 | Eppstein et al. |
| 4,596,556 A | 6/1986 | Morrow |
| 4,609,546 A | 9/1986 | Hiratani |
| 4,766,106 A | 8/1988 | Katre et al. |
| 4,790,824 A | 12/1988 | Morrow |
| 4,941,880 A | 7/1990 | Burns |
| 5,064,413 A | 11/1991 | McKinnon et al. |
| 5,312,335 A | 5/1994 | McKinnon et al. |
| 5,374,548 A | 12/1994 | Caras |
| 5,383,851 A | 1/1995 | McKinnon et al. |
| 5,399,163 A | 3/1995 | Peterson et al. |
| 5,399,331 A | 3/1995 | Loughrey et al. |
| 5,464,933 A | 11/1995 | Bolognesi et al. |
| 5,824,538 A | 10/1998 | Branstorm et al. |
| 5,877,159 A | 3/1999 | Powell et al. |
| 6,500,419 B1 | 12/2002 | Hone et al. |
| 7,368,114 B2 * | 5/2008 | Arthos ............ A61P 37/04 530/300 |

(Continued)

FOREIGN PATENT DOCUMENTS

| | | |
|---|---|---|
| JP | 2004-518624 A | 6/2004 |
| WO | WO 2009/053339 A2 | 4/2009 |
| WO | WO 2011/156747 A1 | 12/2011 |

OTHER PUBLICATIONS

Yu et al (2008; Retrovirology. 5:93; 12 pages as printed.*

(Continued)

*Primary Examiner* — Zachary C Howard
(74) *Attorney, Agent, or Firm* — Knobbe, Martens, Olson & Bear LLP

(57) ABSTRACT

The present invention relates to antibody derivatives against HIV based on a mutated CD4-IgG scaffold with enhanced antiviral and immunomodulatory activities. These antibody derivatives are characterized for having an increased ability to (i) block the entry of human immunodeficiency virus (HIV) into host cells and (ii) elicit effector functions through the activation, of natural killer (NK) cells. The present invention further relates to nucleic acids, vectors and host cells expressing said antibody derivatives, as well their therapeutic and diagnostic applications in human health.

19 Claims, 27 Drawing Sheets

Specification includes a Sequence Listing.

(56) References Cited

U.S. PATENT DOCUMENTS

| | | | |
|---|---|---|---|
| 7,736,649 B2 | 6/2010 | Olson | |
| 2010/0249022 A1* | 9/2010 | Clapham | A61P 35/00 514/19.2 |
| 2011/0269676 A1* | 11/2011 | Jiang | A61P 31/18 514/21.3 |
| 2011/0305670 A1* | 12/2011 | Farzan | A61P 31/12 435/235.1 |

OTHER PUBLICATIONS

Miyamoto et al (2012, Antiviral Chemistry & Chemotherapy; 22: 151-158).*
Tokuriki et al, 2009, Current Opinion in Structural Biology. 19: 596-604.*
Bhattacharya et al, 2017. Plos One. 12(3): e0171355, pp. 1-22 as printed.*
Haas et al., Listeriolysin genes: complete sequence of ilo from *Listeria ivanovii* and of lso from *Listeria seeligeri*, Biochimica et Biophysica Acta, vol. 1130, pp. 81-84, 1992.
Mastroeni et al., Role of T cells, TNF alpha and IFN gamma in recall of immunity to oral challenge with virulent *Salmonellae* in mice vaccinated with live attenuated aro-*Salmonella* vaccines, Microbial Pathogenesis, vol. 13, pp. 477-491, 1992.
Sizemore et al., Attenuated *Shigella* as a DNA Delivery Vehicle for DNA-Mediated Immunization, Science, vol. 270, pp. 299-302, 1995.
Ulmer, J.B., An update on the state of the art of DNA vaccines, Current Opinion in Drug Discovery and Development, vol. 4, No. 2, pp. 192-197, 2001.
Adachi et al., Production of Acquired Immunodeficiency Syndrome-Associated Retrovirus in Human and Nonhuman Cells Transfected With an Infectious Molecular Clone, Journal of Virology, vol. 59, pp. 284-291, 1986.
Adler et al., Range and Natural History of Infection, The BMJ, vol. 294, pp. 1145-1147, 1987.
Akers et al., Formulation Development of Protein Dosage Forms, Pharmaceutical Biotechnology, vol. 14, pp. 47-127, 2002.
Alpert et al., A Novel Assay for Antibody-Dependent Cell-Mediated Cytotoxicity against HIV-1- or SIV-Infected Cells Reveals Incomplete Overlap with Antibodies Measured by Neutralization and Binding Assays, Journal of Virology, vol. 86, pp. 12039-12052, 2012.
Altschul et al., Basic Local Alignment Search Tool, Journal of Molecular Biology, vol. 215, pp. 403-410, 1990.
Altschul et al., Gapped BLAST and PSI-BLAST: A New Generation of Protein Database Search Programs, Nucleic Acids Research, vol. 25, pp. 3389-3402, 1977.
Altschul et al., Local Alignment Statistics, Methods in Enzymology, vol. 266, pp. 460-480, 1996.
Andre et al., Increased Immune Response Elicited by DNA Vaccination with a Synthetic gp120 Sequence with Optimized Codon Usage, Journal of Virology, vol. 72, pp. 1497-1503, 1998.
Angelakopoulos et al., Safety and Shedding of an Attenuated Strain of Listeria Monocytogenes With a Deletion of Acta/Plcb in Adult Volunteers: A Dose Escalation Study of Oral Inoculation, Infection and Immunity, vol. 70, pp. 3592-3601, 2002.
Auer H., Determining the Meaning of Claim Terms, Nature Biotechnology., vol. 24, pp. 41-43, 2006.
Ayuso et al., High AAV Vector Purity Results in Serotype- and Tissue-Independent Enhancement of Transduction Efficiency, Gene Therapy, vol. 17, pp. 503-510, 2010.
Bournazos et al, Broadly Neutralizing Anti-HIV-1 Antibodies Require Fc Effector Functions for In Vivo Activity, Cell, Cell Press, vol. 158, No. 6, pp. 1243-1253, 2014.
Carrillo et al., Gp120/CD4 Blocking Antibodies Are Frequently Elicited in ART-Naïve Chronically HIV-1 Infected Individuals, PLOS One, vol. 10, No. 3, pp. 0120648, 2015.

Chambers et al., Heptad Repeat Sequences are Located Adjacent to Hydrophobic Regions in Several Types of Virus Fusion Glycoproteins, Journal of General Virology, vol. 71, pp. 3075-3080, 1990.
Chan et al., Core Structure of gp41 from the HIV Envelope Glycoprotein, Cell, vol. 89, pp. 263-273, 1997.
Collins et al., Mutation of the Principal Sigma Factor Causes Loss of Virulence in a Strain of the *Mycobacterium tuberculosis* Complex, Proceedings of the National Academy of Sciences of the USA., vol. 92, pp. 8036, 1995.
Dietrich et al., Live Attenuated Bacteria as Vectors to Deliver Plasmid DNA Vaccines., Current Opinion in Molecular Therapeutics, vol. 5, pp. 10-19, 2003.
Donnelly et al., DNA Vaccines, Annual Review of Immunology, vol. 15, pp. 617-648, 1997.
Donnenberg et al., Internalization of *Escherichia coli* into Human Kidney Epithelial Cells: Comparison of Fecal and Pyelonephritis-Associated Strains, The Journal of Infectious Diseases, vol. 169, pp. 831-838, 1994.
Eggink et al, Resistance of Human Immunodeficiency Virus Type 1 to a Third-Generation Fusion Inhibitor Requires Multiple Mutations in gp41 and Is Accompanied by a Dramatic Loss of gp41 Function, Journal of Virology, vol. 85, No. 20, pp. 10785-10797, 2011.
Eggink et al., Selection of T1249-Resistant Human Immunodeficiency Virus Type 1 Variants, Journal of Virology, vol. 82, No. 13, pp. 6678-6688, 2008.
Euler et al., Exploring the Potential of Monoclonal Antibody Therapeutics for HIV-1 Eradication, AIDS Research and Human Retroviruses, vol. 31, No. 1, pp. 13-24, 2015.
Evans et al., Plasmid-Controlled Colonization Factor Associated With Virulence in *Esherichia coli* Enterotoxigenic for Humans, Infection and Immunity, vol. 12, pp. 656-667, 1975.
FACSCalibur Flow Cytometer, BD Biosciences Corp.
Feng et al., High-Level Expression and Mutagenesis of Recombinant Human Phosphatidylcholine Transfer Protein Using a Synthetic Gene: Evidence for a C-Terminal Membrane Binding Domain, Biochemistry, vol. 39, No. 50, pp. 15399-15409, 2000.
Gardner et al, AAV-expressed eCD4-Ig provides durable protection from multiple SHIV challenges, Nature, vol. 519, No. 7541, pp. 87-91, 2015.
Gartner et al., The role of mononuclear phagocytes in HTLV-III/LAV infection, Science, vol. 233, pp. 215-219, 1986.
Gentschev et al., Delivery of Protein Antigens and DNA by Virulence-Attenuated Strains of *Salmonella typhimurium* and Listeria Monocytogenes, Journal of Biotechnology, vol. 83, pp. 19-26, 2000.
Griffith et al., Tuberculosis Outbreak Among Healthcare Workers in a Community Hospital, American Journal of Respiratory and Critical Care Medicine, vol. 152, pp. 808-811, 1995.
Gurunathan et al., DNA Vaccines: Immunology, application and Optimization, Annual Review of Immunology, vol. 18, pp. 927-974, 2000.
Haynes, B., New Approaches to HIV Vaccine Development, Current Opinion in Immunology vol. 35, pp. 39-47, 2015.
Hondalus et al., Attenuation of and Protection Induced by a Leucine Auxotroph of *Mycobacterium tuberculosis*, Infection and Immunity, vol. 68, No. 5, pp. 2888-2898, 2000.
Hone et al., Construction of Genetically Defined Double Aro Mutants of *Salmonella typhi*, Vaccine, vol. 9, pp. 810-816, 1991.
Hone et al., Vaccination with a Shigella DNA Vaccine Vector Induces Antigen-Specific CD8+ T Cells and Antiviral Protective Immunity, Journal of Virology, vol. 75, pp. 9665-9670, 2001.
Humphreys et al., High-Level Periplasmic Expression in *Escherichia coli* Using a Eukaryotic Signal Peptide: Importance of Codon Usage at the 5' End of the Coding Sequence, Protein Expression and Purification, vol. 20, No. 2, pp. 252-264, 2000.
International Search Report With Written Opinion dated Apr. 19, 2017 in International Application No. PCT/IB2016/001868.
Jacobson et al, Treatment of Advanced Human Immunodeficiency Virus Type 1 Disease with the Viral Entry Inhibitor PRO 542, Antimicrobial Agents and Chemotherapy, vol. 48, No. 2, pp. 423-429, 2004.
Karlin et al., Applications and statistics for multiple high-scoring segments in molecular sequences, Proceedings National Academy of Sciences of the USA, vol. 90, pp. 5873-5877, 1993.

(56) References Cited

OTHER PUBLICATIONS

Karlin et al., Methods for assessing the statistical significance of molecular sequence features by using general scoring schemes, Proceedings National Academy of Sciences of the USA, vol. 87, pp. 2264-2268, 1990.

Lagenaur et al., sCD4-17b Bifunctional Protein: Extremely Broad and Potent Neutralization of HIV-1 Env Pseudotyped Viruses From Genetically Diverse Primary Isolates, Retrovirology, vol. 7, pp. 11, 2010.

Li et al., Human Immunodeficiency Virus Type 1 env Clones from Acute and Early Subtype B Infections for Standardized Assessments of Vaccine-Elicited Neutralizing Antibodies, Journal of Virology, vol. 79, No. 16, po. 10108-10125, 2005.

Lu et al., A Bivalent Recombinant Protein Inactivates HIV-1 by Targeting the Gp41 Prehairpin Fusion Intermediate Induced by CD4 D1D2 Domainsm, Retrovirology, vol. 9, No. 104, pp. 1-14, 2012.

Lupas A, Coiled Coils: New Structures and New Functions, Trends in Biochemical Sciences, vol. 21, pp. 375-382, 1996.

Mascola et al, HIV-1 neutralizing antibodies: understanding nature's pathways, Immunological Reviews, vol. 254, No. 1, pp. 225-244, 2013.

Mascola et al., Human Immunodeficiency Virus Type 1 env Clones from Acute and Early Subtype B Infections for Standardized Assessments of Vaccine-Elicited Neutralizing Antibodies, Journal of Virology, vol. 79, No. 16, pp. 10103, 2005.

Matsushita et al., Adeno-Associated Virus Vectors Can Be Efficiently Produced Without Helper Virus, Gene Therapy, vol. 5, pp. 938-945, 1998.

McKee et al., Investigation of Enterohemorrhagic *Escherichia coli* O157:H7 Adherence Characteristics and Invasion Potential Reveals a New Attachment Pattern Shared by Intestinal *E. coli*, Infection and Immunity, vol. 63, pp. 2070-2074, 1995.

Milligan et al., Passively Acquired Antibody-Dependent Cellular Cytotoxicity (ADCC) Activity in HIV-Infected Infants Is Associated with Reduced Mortality, Cell Host & Microbe, vol. 17, No. 4, pp. 500-506, 2015.

Mulligan et al., Human Trials of HIV-1 Vaccines, AIDS, vol. 13, No. A, pp. S105-S112, 1999.

Nagashima et al, Human Immunodeficiency Virus Type 1 Entry Inhibitors PRO 542 and T-20 Are Potently Synergistic in Blocking Virus-Cell and Cell Cell Fusion, Journal of Infectious Diseases, vol. 183, No. 7, pp. 1121-1125, 2001.

Narum et al., Codon Optimization of Gene Fragments Encoding Plasmodium falciparum Merzoite Proteins Enhances DNA Vaccine Protein Expression and Immunogfenicity in Mice, Infection and Immunity, vol. 69, No. 12, pp. 7250-7253, 2001.

Needleman et al., A general method applicable to the search for similarities in the amino acid sequence of two proteins, Journal of molecular Biology, vol. 48, pp. 443-453, 1970.

O'Hagan et al., Induction of Potent Immune Responses by Cationic Microparticles with Adsorbed Human Immunodeficiency Virus DNA Vaccines, Journal of Virology, vol. 75, pp. 9037-9043, 2001.

Outchkourov et al., Optimization of the Expression of Equistatin in Pichia Pastoris, Protein Expression and Purification, vol. 24, No. 1, pp. 18-24, 2002.

Pearson et al., Improved Tools for Biological Sequence Comparison, Proceedings of the National Academy of Sciences of the United States of America, Bestfit, FASTA and TFASTA Programs, vol. 85, pp. 2444-2448, 1988.

Peisajovich S et al., Viral fusion proteins: multiple regions contribute to membrane fusion, Biochimica et Biophysica Acta (BBA)—Biomembranes, vol. 1614, pp. 122-129, 2003.

Peters et al., Tailoring host immune responses to Listeria by manipulation of virulence genes—the interface between innate and acquired immunity, Pathogens and Disease, vol. 35, pp. 243-253, 2003.

Rainczuk et al., A Bicistronic DNA Vaccine Containing Apical Membrane Antigen 1 and Merozoite Surface Protein 4/5 Can Prime Humoral and Cellular Immune Responses and Partially Protect Mice against Virulent Plasmodium chabaudi adami DS Malaria, Infection and Immunity, vol. 72, pp. 5565-5573, 2004.

Rapp et al., DNA Vaccination With Gp96-Peptide Fusion Proteins Induces Protection Against an Intracellular Bacterial Pathogen, International Immunology, vol. 16, pp. 597-605, 2004.

Robinson et al., DNA Vaccine for Viral Infections: Basic Studies and Applications, Advances in Virus Research, vol. 55, pp. 1-74, 2000.

Sambandamurthy et al., A Pantothenate Auxotroph of *Mycobacterium tuberculosis* Is Highly Attenuated and Protects Mice Against Tuberculosis, Nature Medicine, vol. 8, pp. 1171-1174, 2002.

Samulski et al., AAV-Mediated Gene Therapy for Research and Therapeutic Purposes, Annual Review of Virology, vol. 1, pp. 427-451, 20144.

Sanchez-Palomino et al., A Cell-To-Cell HIV Transfer Assay Identifies Humoral Responses With Broad Neutralization Activity, Vaccine, vol. 29, pp. 5250-5259, 2011.

Sansonetti et al., Plasmid-mediated invasiveness of "Shigella-like" *Escherichia coli*, Annales de Microbiologie, vol. 132A, pp. 351-355, 1982.

Seaman et al., Tiered Categorization of a Diverse Panel of HIV-1 Env Pseudoviruses for Assessment of Neutralizing Antibodies, Journal Virology, vol. 84, pp. 1439-1452, 2010.

Shata et al., Mucosal and systemic HIV-1 Env-specific CD8+ T-cells develop after intragastric vaccination with a *Salmonella* Env DNA vaccine vector, Vaccine, vol. 20, pp. 623-629, 2001.

Shata et al., Recent advances with recombinant bacterial vaccine vectors, Molecular Medicine Today, vol. 6, pp. 66-71, 2000.

Siliciano et al., Recent developments in the search for a cure for HIV-1 infection: Targeting the latent reservoir for HIV-1, Journal of Allergy and Clinical Immunology, vol. 134, No. 1, pp. 12-19, 2014.

Sizemore et al., Attenuated bacteria as a DNA delivery vehicle for DNA-mediated immunization, Vaccine, vol. 15, pp. 804-807, 1997.

Smith et al., Comparison of Biosequences, Advances in Applied Mathematics, vol. 2, pp. 482-489, 1981.

Stevens et al., Oral Immunization with Recombinant Listeria monocytogenes Controls Virus Load after Vaginal Challenge with Feline Immunodeficiency Virus, Journal of Virology, vol. 78, pp. 8210-8218, 2004.

Strejan et al., Suppression of chronic-relapsing experimental allergic encephalomyelitis in strain-13 guinea pigs by administration of liposome-associated myelin basic protein, Neuroimmunoly, vol. 7, pp. 27-41, 1984.

Suarez et al., The Pre-Transmembrane Region of the Human Immunodeficiency Virus Type-1 Glycoprotein: A Novel Fusogenic Sequence, FEBS Letters, vol. 477, pp. 145-149, 2000.

Thompson et al., Pathogenicity and Immunogenicity of Alisteria Monocytogenes Strain That Requiresd-Alanine for Growth, Infection and Immunity, vol. 66, pp. 3552-3561, 1998.

Ulmer et al., Heterologous Protection Against Influenza by Injection of DNA Encoding a Viral Protein, Science, vol. 259, pp. 1745-1749, 1993.

Van Soolingen et al., Predominance of a single genotype of *Mycobacterium tuberculosis* in countries of east Asia, Journal of Clinical Microbiology, vol. 33, pp. 3234-3238, 1995.

Wei et al., Antibody neutralization and escape by HIV-1, Nature, vol. 422, pp. 307-312, 2003.

Wright et al., Identification of factors that contribute to recombinant AAV2 particle aggregation and methods to prevent its occurrence during vector purification and formulation, Molecular Therapy, vol. 12, pp. 171-178, 2005.

Yang et al., Stoichiometry of Antibody Neutralization of Human Immunodeficiency Virus Type 1, Journal of Virology, vol. 79, pp. 3500-3508, 2005.

Zhang et al., Peptide Fusion Inhibitors Targeting The HIV-1 Gp41: A Patent Review (2009-2014) Expert Opinion on Therapeutic Patents, vol. 25, pp. 159-173, 2015.

\* cited by examiner

Fig.1

| | IC50 (ng/ml) | | | | | | | | | | |
|---|---|---|---|---|---|---|---|---|---|---|---|
| | AC10 | SVBP 6 | SVBP 8 | SVBP 11 | SVBP 12 | SVBP 14 | SVBP 15 | SVBP 17 | SVBP 18 | SVBP 19 | Description |
| MOLEC-0 | >100 | >100 | >100 | >100 | >100 | >100 | >100 | >100 | >100 | >100 | CD4-IgG1 |
| MOLEC-1 | >100 | 69.98 | >100 | >100 | >100 | >100 | >100 | >100 | >100 | >100 | eCD4-Ig /reference |
| MOLEC-5 | 4.7 | 1.1 | 3.6 | 8.1 | 5.2 | 1.4 | 1.8 | 12.0 | 1.2 | 8.5 | CD4-mIgG1-CCR5-4L-T20 |
| MOLEC-7 | 1.3 | 2.5 | 4.1 | 7.1 | 2.8 | 1.0 | 1.2 | 18.7 | 2.3 | 10.3 | CD4-mIgG1-10L-T20 |
| MOLEC-8 | 3.6 | 13.8 | 3.7 | 13.4 | 3.1 | 1.4 | 1.5 | 25.0 | 3.4 | 14.0 | CD4-mIgG1-4L-T20 |
| | Tier 2 | Tier 2 | Tier 2 | Tier 3 | Tier 2 | Tier 2 | Tier 2 | Tier 3 | Tier 2 | Tier 2 | |
| RATIO MOLECULE-7/ MOLECULE-1 | >60 | >40 | >20 | >15 | >35 | >100 | >80 | >6 | >40 | >9 | |

Fig. 9

HIV ANTIBODY DERIVATIVES WITH DUAL ANTIVIRAL AND IMMUNOMODULATORY ACTIVITIES FROM CD4 AND GP41

SEQUENCE LISTING IN ELECTRONIC FORMAT

The present application includes an Electronic Sequence Listing as an xml file filed electronically. The Electronic Sequence Listing is provided as a file entitled DURC074001APCSEQLIST.xml, created and last saved on Jul. 25, 2022, which is 89,679 bytes in size. The information in the Electronic Sequence Listing is incorporated herein by reference in its entirety.

FIELD OF THE INVENTION

The present invention relates to antibody derivatives against HIV with enhanced antiviral and immunomodulatory activities. The antibody derivatives of the present invention are characterized for having an increased ability to (i) block the entry of human immunodeficiency virus (HIV) into host cells and (ii) elicit effector functions through the activation of natural killer (NK) and other immune system cells. Various forms of these polypeptides are disclosed and exemplified. Isolated nucleic acids, vectors and host cells expressing these polypeptides, as well their therapeutic and diagnostic applications in human health, are also within the scope of the present invention.

BACKGROUND OF THE INVENTION

HIV infection is one of the major threats to global human health. It is estimated that more than 78 million people worldwide have been infected by the human immunodeficiency virus since 1981. Nearly half of these infected individuals have died of the resultant Acquired Immunodeficiency Syndrome (AIDS) during the same time frame. See UNAIDS, www.unaids.org, October 2015.

The generation of protective antibodies is the main mechanism for developing vaccines against human pathogens. However, the development of immunogens able to elicit such antibodies against HIV has failed so far. The design of these immunogens requires, firstly, identifying conserved epitopes to assure a continuous and stable response and, secondly, devising new and more efficient immunogens that present those epitopes properly. See Haynes B, Curr Opin Immunol. 2015; 35:39-47. In contrast to these insufficient advances in immunogen design, a large number of new, potent and broad-spectrum antibodies (i.e. broadly neutralizing antibodies, bNAbs) against HIV envelope glycoprotein isolated from HIV infected individuals have been identified recently. See Mascola J, et al., Immunol Rev. 2013; 254:225-244. In addition, synthetic molecules based on antibody structure have been also proposed as new therapeutic agents. See Gardner M, et al., Nature 2015; 519:87-91. Indeed, highly potent antibodies may protect uninfected individuals from HIV acquisition or may be used in eradication strategies in HIV infected patients. See Mascola, 2013, supra. The use of neutralizing antibodies against the envelope glycoprotein and its subunits has also been proposed to prevent HIV replication in vivo. See Yang X, et al., J. Virol. 2005; 79:3500-3508.

In therapeutic grounds, antibodies are especially relevant due to their dual function as antiviral agents able to block HIV replication through binding to HIV envelope glycoprotein and as NK cell activators though the interaction of constant regions of antibody chains (Fc) with the Fc receptor CD16 expressed on the surface of NK and other cells. This interaction enables CD16+ immune cells to kill infected cells through a mechanism known as antibody-dependent cellular cytotoxicity (ADCC). See Milligan C, et al., Cell Host Microbe. 2015; 17:500-506. Both activities seem to be required for the protection of uninfected subjects. Therefore, there is a need in the art for neutralizing antibodies with increased antiviral and ADCC activities.

SUMMARY OF THE INVENTION

In a first aspect, the present invention refers to antibody derivatives which comprise from the N- to C-terminus:
(a) the D1 and D2 extracellular domains of a human CD4 receptor,
(b) the Fc portion of a human IgG,
(c) a moiety selected from the group consisting of
  (i) a linker polypeptide of sequence $(GGGGS)_n$ wherein $1 \leq n \leq 10$,
  (ii) a human CCR5 receptor sequence and
  (iii) combinations thereof, and
(d) a gp41-derived polypeptide.

The antibody derivatives of the invention have an antiviral and ADCC activity higher than any other comparable antibody derivatives known in the art. See Gardner, 2015, supra.

In an additional aspect, the invention relates to the nucleic acids encoding the antibody derivatives of the invention, to vectors comprising said nucleic acids and to host cells comprising the nucleic acids and vectors indicated before.

In a further aspect, the invention refers to pharmaceutical compositions comprising the antibody derivatives, nucleic acids, vectors and host cells of the invention, or mixtures thereof.

In another aspect, the invention is directed to a combination comprising the antibody derivatives, nucleic acids, vectors, host cells and pharmaceutical compositions of the invention and at least one therapeutic agent.

In a still further aspect, the invention relates to the use of the antibody derivatives, nucleic acids, vectors, host cells, pharmaceutical compositions and combinations of the invention, or mixtures thereof, as a medicament. In a further version of this aspect, the invention refers to the use of the antibody derivatives, nucleic acids, vectors, host cells, pharmaceutical compositions and combinations of the invention, or mixtures thereof, in the treatment or prevention of HIV infection or AIDS. In an alternative form of this aspect, the invention relates to a method of treating or preventing HIV infection or AIDS in a subject which comprises the administration of a therapeutically effective amount of the antibody derivatives, nucleic acids, vectors, host cells, pharmaceutical compositions and combinations of the invention, or mixtures thereof, to the subject. In a further alternative form of this aspect, the invention refers to the use of the antibody derivatives, nucleic acids, vectors, host cells, pharmaceutical compositions and combinations of the invention, or mixtures thereof, in the manufacture of a medicament for the treatment or prevention of HIV infection or AIDS.

Additionally, the present invention relates to a method of preparing the antibody derivatives of the invention which comprises the steps of (a) culturing a host cell comprising a nucleic acid according to the invention, (b) expressing the nucleic acid sequence and (c) recovering the antibody derivative from the host cell culture.

In another aspect, the invention refers to a method of inactivating HIV which comprises the step of contacting the virus with an antibody derivative of the invention.

In an additional aspect, the invention is directed to a method of inducing the expression of gp120 in a HIV infected cell which comprises the step of contacting the infected cell with the antibody derivatives, nucleic acids, vectors, host cells, pharmaceutical compositions and combinations of the invention, or a mixture thereof.

In a further aspect, the invention relates to a method of detecting HIV in a sample which comprises the steps of (a) contacting the sample with an antibody derivative of the invention and (b) determining whether the antibody derivative specifically binds to a molecule of the sample.

In a still further aspect, the invention relates to a kit comprising the antibody derivatives, nucleic acids, vectors, host cells and pharmaceutical compositions of the invention, or mixtures thereof.

BRIEF DESCRIPTION OF THE DRAWINGS

FIG. 1. Schematic representation of the different changes introduced into the human IgG1 molecule to obtain the first generation antibody derivatives of the invention.

FIG. 9. Neutralization capacity of the second generation antibody derivatives MOLECULE-5, MOLECULE-7 and MOLECULE-8 against a panel of HIV SVBP subtype isolates. MOLECULE-0 and MOLECULE-1 were included in the analysis as references.

DETAILED DESCRIPTION OF THE INVENTION

Figure 2:
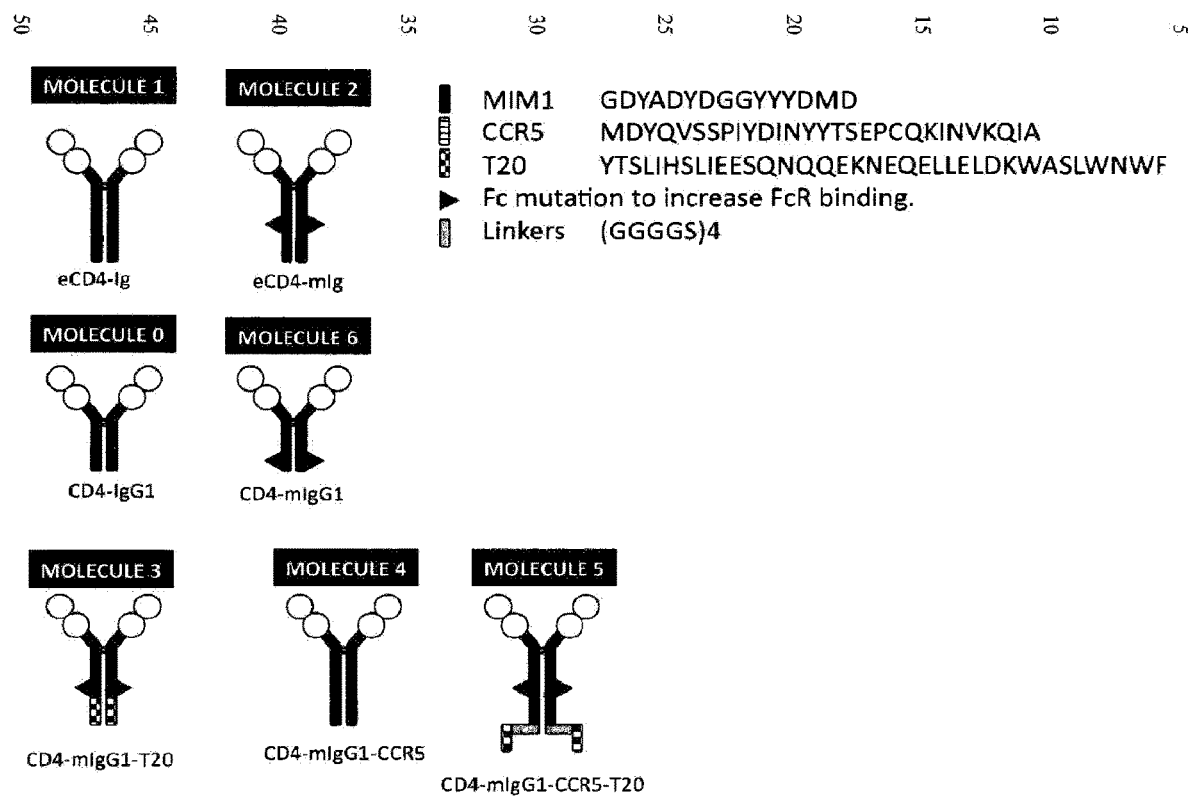
FIG. 2. Schematic representation of the first generation antibody derivatives MOLECULES-1-5. MIM1=Amino acids 443-457 of SEQ ID NO: 12 (SEQ ID NO: 43); CCR5=SEQ ID NO: 6; T20=SEQ ID NO: 7, GGGGS=SEQ ID NO: 5.

The present invention relates to HIV antibody derivatives with enhanced dual antiviral and immunomodulatory activities. The antibody derivatives of the present invention are characterized for having an increased ability to (i) block the entry of human immunodeficiency virus (HIV) into host cells and (ii) elicit effector functions through the activation of natural killer (NK) cells.

1. Definitions of General Terms and Expressions

The term "AC10", as used herein, refers to a HIV primary isolate characterized by its resistance to anti-CD4 binding site antibodies. AC10 is classified as a tier 2 isolate. See Seaman M, et al., J. Virol. 2010; 84:1439-1452.

The term "adeno-associated virus" or "AAV", as used herein, refers to a virus member of the Parvoviridae family which comprises a linear, single-stranded DNA genome of about 5,000 nucleotides. At least 11 recognized serotypes of AAV (AAV1-11) are known in the art.

The term "AAV vector", as used herein, refers to a nucleic acid having an AAV 5' inverted terminal repeat (ITR) sequence and an AAV 3' ITR flanking a polypeptide-coding sequence operably linked to transcription regulatory elements (e.g. promoters, enhancers) and a polyadenylation sequence. The AAV vector may include, optionally, one or more introns inserted between exons of the polypeptide-coding sequence. See Samulski J, et al., Annu. Rev. Virol. 2014; 1:427-451.

The term "AIDS", as used herein, refers to the symptomatic phase of HIV infection, and includes both Acquired Immune Deficiency Syndrome (commonly known as AIDS) and "ARC," or AIDS-Related Complex. See Adler M, et al., Brit. Med. J. 1987; 294: 1145-1147. The immunological and clinical manifestations of AIDS are well known in the art and include, for example, opportunistic infections and cancers resulting from immune deficiency.

The term "amino acid", as used herein, refers to naturally occurring and synthetic amino acids, as well as amino acid analogs and amino acid mimetics that function in a manner similar to the naturally occurring amino acids. Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

The term "antibody drug conjugate" or "ADC", as used herein, refers to an antibody, antigen-binding antibody fragment, antibody derivative, antibody complex or antibody fusion protein that is conjugated to a therapeutic agent. Conjugation may be covalent or non-covalent. Preferably, conjugation is covalent.

The term "antiretroviral therapy" or "AT", as used herein, refers to the administration of one or more antiretroviral drugs (i.e. HIV antiretrovirals) to inhibit the replication of HIV. Typically, AT involves the administration of at least one antiretroviral agent (or, commonly, a cocktail of antiretrovirals) such as nucleoside reverse transcriptase inhibitor (e.g. zidovudine (AZT, lamivudine (3TC) and abacavir), non-nucleoside reverse transcriptase inhibitor (e.g. nevirapine and efavirenz) and protease inhibitor (e.g. indinavir, ritonavir and lopinavir). The term Highly Active Antiretroviral Therapy ("HAART") refers to treatment regimens designed to suppress aggressively HIV replication and disease progression. HAART usually consists of three or more different drugs, such as, for example, two nucleoside reverse transcriptase inhibitors and a protease inhibitor.

The term "binding efficacy", as used herein, refers to the affinity of a molecule to the CD4 receptor and, preferably, the D1 and D2 domains of said receptor. In the context of the invention, "affinity" means the strength with which an antibody derivative binds, for example, to the CD4 binding site of gp120. As used herein, the term "binding" or "specifically binding", refers to the interaction between binding pairs (e.g. two proteins or compounds, preferably between (i) the CD4 binding site of gp120 and (ii) the CD4 receptor or the D1 and D2 domains of the CD4 receptor. In some embodiments, the interaction has an affinity constant of at most $10^{-6}$ moles/liter, at most $10^{-7}$ moles/liter, or at most $10^{-8}$ moles/liter. In general, the phrase "binding" or "specifically binding" refers to the specific binding of one compound to another, wherein the level of binding, as measured by any standard assay, is statistically significantly higher than the background control for the assay.

The term "C34", as used herein, refers to a gp41-derived polypeptide of SEQ ID NO:9 covering part of the HR2 region of gp41. See Eggink D, et al., J. Virol. 2008; 82(13):6678-6688.

The term "CCR5", as used herein, refers to the human C—C chemokine receptor 5, also known as CD195, a 7 transmembrane domain receptor coupled to G proteins. CCR5 binds to different chemokines and acts as the coreceptor of HIV Env during the process of HIV entry into target cells. The HIV coreceptor function involves different regions of CCR5; however, the first interaction is established between the N-terminal extracellular region of CCR5 and the coreceptor binding site of HIV Env located in the gp120 subunit. See Lagenaur L, et al., Retrovirology 2010; 7:11. The complete protein sequence for human CCR5 has the UniProt accession number P51681 (Aug. 18, 2015).

The term "CD4" or "CD4 receptor", as used herein, refers to a cluster of differentiation 4, a glycoprotein expressed on the surface of T helper cells, monocytes, macrophages and dendritic cells. CD4 assists the T cell receptor (TCR) in its joining with an antigen-presenting cell. Using its portion that resides inside the T cell, CD4 amplifies the signal generated by the TCR by recruiting an enzyme, known as the tyrosine kinase lck, which is essential for activating many molecules involved in the signaling cascade of an activated T cell. The complete protein sequence for human CD4 has the UniProt accession number P01730 (Jun. 18, 2012).

The term "codon optimized", as used herein, refers to the alteration of codons in nucleic acids to reflect the typical codon usage of the host organism to improve the expression of a reference polypeptide without altering its amino acid sequence. There are several methods and software tools known in the art for codon optimization. See Narum D, et al., Infect. Immun. 2001; 69(12):7250-7253), Outchkourov N, et al., Protein Expr. Purif. 2002; 24(1):18-24, Feng L, et al., Biochemistry 2000; 39(50):15399-15409 and Humphreys D, et al., Protein Expr. Purif. 2000; 20(2):252-264.

The term "comprising" or "comprises", as used herein, discloses also "consisting of" according to the generally accepted patent practice.

The term "Env" or "gp160", as used herein, refers to a glycoprotein having either the antigenic specificity or the biological function of the outer envelope protein (Env) of HIV and encompassing two subunits, the gp120 and the gp41 glycoproteins. Exemplary sequences of wild type (wt) gp160 polypeptides are available. See GenBank accession nos. AAB05604 and AAD12142.

The term "fragment crystallizable region" or "Fc region", as used herein, refers to the tail region of an antibody that interacts with cell surface receptors called Fc receptors and some proteins of the complement system.

The expression "functionally equivalent variant", as used herein, refers to: (i) a polypeptide resulting from the modification, deletion or insertion or one or more amino acids and which substantially preserves the activity of its reference polypeptide and (ii) a polynucleotide resulting from the modification, deletion or insertion or one or more bases and which substantially preserves the activity of the polypeptide expressed by the reference nucleic acid. Functionally equivalent variants contemplated in the context of the present invention, include polypeptides which show at least 60%, 70%, 80%, 85%, 90%, 92%, 94%, 96%, 98%, 99% of similarity or identity with sequences SEQ ID NOs:1-10 or polynucleotides which show at least 60%, 70%, 80%, 85%, 90%, 92%, 94%, 96%, 98%, 99% of similarity or identity with sequences SEQ ID NOs:22-31. The degree of identity or similarity between two polypeptides or two polynucleotides is determined by using computer-implemented algorithms and methods that are widely known in the art. The identity and similarity between two sequences of amino acids is preferably determined using the BLASTP algorithm. See Altschul S, et al., "BLAST Manual" (NCBI NLM NIH, Bethesda, Md., USA, 2001).

The term "fusion protein", as used herein, relates to proteins generated by gene technology which consist of two or more functional domains derived from different proteins. A fusion protein may be obtained by conventional means (e.g. by means of gene expression of the nucleotide sequence encoding for said fusion protein in a suitable cell).

The term "gp41", as used herein, refers to human immunodeficiency virus-I envelope glycoprotein gp41. Gp41 is a subunit which forms the Env glycoprotein of HIV-1 together with gp 120. Env is a trimer composed of three external subunits (gp120) and three transmembrane subunits (gp41). The extracellular moiety of gp41 protein contains three essential functional regions: a fusion peptide (FP), a N-terminal heptad repeat (HR1) and a C-terminal heptad repeat (HR2). The HR1 and HR2 regions contain a number of leucine zipperlike motifs which have tendency to form coiled structures. See Peisajovich S, Shai Y, Biochem. Biophys. Acta 2003; 1614:122-129; Suarez T, et al., FEBS Lett. 2000; 477:145-149; Chan D, et al., Cell 1997; 89:263-273. The nucleic acid and amino acid sequences of a large number of HIV gp-41 are readily available to the public. See HIV Sequence Database, www.hiv.1an1.gov/content/seauence/H1V/mainpage.htm1, November 2015.

The term "gp41 inhibitors", as used herein, include a series of polypeptides of different length that cover the HR2 region of gp41. These inhibitors include, but are not limited to, the T-20, C34, T-1249 and T-2635 gp41-derived polypeptides.

The expression "gp41-derived polypeptide", as used herein, refers to a polypeptide derived from the heptad repeat 1 (HR1) or the heptad repeat 2 (HR2) motifs of gp41.

The gp41 HR1 and HR2 sequences are well known in the art. See Lupas A, Trends Biochem. Sci. 1996; 21:375-382 and Chambers P, et al., J. Gen. Virol. 1990; 71:3075-3080. Preferably, the gp41-derived polypeptide originates from HR2. The gp41-derived polypeptides may contain additional exogenous amino acid located at their N- or C-terminals. Preferably, the exogenous amino acids are less than 10, more preferably, less than 5, and, most preferably, less than 3.

The term "gp120", as used herein, refers to a glycoprotein having either the antigenic specificity or the biological function of the outer envelope protein (env) of HIV. A "gp120 protein" is a molecule derived from a gp120 region of an Env polypeptide. The amino acid sequence of gp120 is approximately 511 amino acids. Gp120 is a heavily N-glycosylated protein with an apparent molecular weight of 120 kD. Gp120 contains five relatively conserved domains (C1-05) interspersed with five variable domains (V1-V5). The variable domains contain extensive amino acid substitutions, insertions and deletions. A "gp120 polypeptide" includes both single subunits and multimers. The gp41 portion is anchored in (and spans) the membrane bilayer of the virion, while the gp120 segment protrudes into the surrounding environment. The receptor binding domain of gp120 is localized to N-terminal half of the protein. This is followed by a proline rich region (PRR), which behaves either as a hinge or trigger to communicate receptor binding to the fusion machinery. The C-terminus of gp120 is highly conserved and interacts with gp41. See GenBank accession nos. AAB05604 and AAD12142.

The term "HIV", as used herein, include HIV-1 and HIV-2, SHIV and SIV. "HIV-1" means the human immunodeficiency virus type-1. HIV-1 includes, but is not limited to, extracellular virus particles and the forms of HIV-1 associated with HIV-1 infected cells. The HIV-1 virus may represent any of the known major subtypes (Classes A, B, C, D E, F, G and H) or outlying subtype (Group 0) including laboratory strains and primary isolates. "HIV-2" means the human immunodeficiency virus type-2. HIV-2 includes, but is not limited to, extracellular virus particles and the forms of HIV-2 associated with HIV-2 infected cells. The term "SIV" refers to simian immunodeficiency virus which is an HIV-like virus that infects monkeys, chimpanzees, and other nonhuman primates. SIV includes, but is not limited to, extracellular virus particles and the forms of SIV associated with SIV infected cells.

The term "HIV exposure", as used herein, refers to the contact of an uninfected subject with a subject having an HIV infection or AIDS, or the contact with body fluids from such HIV-infected subject, in which such fluids from the infected subject contact a mucous membrane, a cut or abrasion in the tissue (e.g. needle stick, unprotected sexual intercourse), or other surface of the uninfected subject in such a way that the virus could be transmitted from the infected subject or infected subject's body fluids to the uninfected subject.

The term "HIV infection", as used herein, refers to indications of the presence of the HIV virus in an individual including asymptomatic seropositivity, AIDS-related complex (ARC), and acquired immunodeficiency syndrome (AIDS).

The term "$IC_{50}$", as used herein, refers to the amount of a particular active agent required for inhibiting 50% of a given biological process or component of a biological process (i.e. an enzyme, cell, cell receptor or microorganism).

The terms "identical" or percent "identity" in the context of two or more nucleic acids or polypeptides refer to two or more sequences or subsequences that are the same or have a specified percentage of nucleotides or amino acid residues that are the same when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art which can be used to obtain alignments of amino acid or nucleotide sequences. Examples of algorithms suitable for determining sequence similarity include, but are not limited to, the BLAST, Gapped BLAST, and BLAST 2.0, WU-BLAST-2, ALIGN, and ALIGN-2 algorithms. See Altschul S, et al., Nuc. Acids Res. 1977; 25:3389-3402, Altschul S, et al., J. Mol. Biol. 1990; 215:403-410, Altschul S, et al., Meth. Enzymol. 1996; 266:460-480, Karlin S, et al., Proc. Natl. Acad. Sci, USA 1990; 87:2264-2268, Karlin S, et al., Proc. Natl. Acad. Sci. USA 1993; 90:5873-5877, Genentech Corp, South San Francisco, CA, US, blast.ncbi.nlm.nih.gov/Blast.cgi, November 2015, Methods of alignment of sequences for comparison are well known in the art. Optimal alignment of sequences for comparison can be conducted, for instance, by the Smith-Waterman local homology algorithm, by the Needleman-Wunsch homology alignment algorithm, by the Pearson-Lipman similarity search method, by computerized implementations of these algorithms or by manual alignment and visual inspection. See Smith T, et al., Adv. Appl. Math, 1981; 2:482-489, Needleman S, et al., J. Mol. Biol. 1970; 48:443-453, Pearson W, et al., Lipman D, Proc. Natl, Acad. Sci. USA 1988; 85:2444-2448, the GAP, BESTFIT, FASTA and TFASTA programs, Wisconsin Genetics Software Package, Genetics 30 Computer Group, Madison, WI, USA; Ausubel F, et al., Eds., "Short Protocols in Molecular Biology", 5$^{th}$ Ed. (John Wiley and Sons, Inc., New York, NY, USA, 2002).

The term "kit", as used herein, refers to a product containing the different reagents necessary for carrying out the uses and methods of the invention which is packed so as to allow their transport and storage. Materials suitable for packing the components of the kit include crystal, plastic (e.g. polyethylene, polypropylene, polycarbonate), bottles, vials, paper or envelopes.

The term "neutralizing antibody", as used herein, is any antibody, antigen-binding fragment or antibody derivative that binds to an extracellular molecule (e.g. a protein or a protein domain in the surface of a pathogenic virus) and interferes with the ability of the extracellular molecule to infect a cell or modulate its activity. Typically, the antibody derivatives of the invention can bind to the surface of the extracellular molecule and are able to inhibit its coupling to a cell by at least 99%, 95%, 90%, 85%, 80%, 75%, 70%, 60%, 50%, 45%, 40%, 35%, 30%, 25%, 20% or 10% relative to the attachment of the extracellular molecule to the cell in the absence of said antibody derivatives or in the presence of a negative control. Methods for confirming whether an antibody derivative is neutralizing have been described in the art. See Li M, et al., J. Virol. 2005; 79:10108-10125, Wei X, et al., Nature 2003; 422:307-312, and Montefiori D, Curr. Protoc. Immunol. 2005; Jan, Chapter 12:Unit 12.11. In the context of the invention, the pathogen is preferably HIV, and more specifically, the gp120 protein of the HIV viral envelope. In particular, the term "HIV neutralizing antibody" refers to an antibody derivative with affinity to the CD4 binding site of gp120 such as IgGb12. The term "neutralizing antibodies" includes the subclass of bnAbs. As used herein, "broadly neutralizing antibody" or "bnAb" is understood as an antibody obtained by any method that, when delivered at an effective dose, can be used as a therapeutic agent for the prevention or treatment of HIV infection or AIDS against more than 7 strains of HIV, preferably more than 8, 9, 10, 11, 12, 13, 14, 15, 16, 17, 18, 19, 20 or more strains of HIV.

The term "NK cell", as used herein, refers to a "Natural Killer cell", a type of cytotoxic lymphocyte critical to the innate immune system. NK cells provide rapid responses to virally infected cells and respond to tumor formation, acting at around 3 days after infection. Typically, immune cells detect HLA presented on infected cell surfaces, triggering cytokine release causing lysis or apoptosis. NK cells are unique, however, as they have the ability to recognize stressed cells in the absence of antibodies and HLA, allowing for a much faster immune reaction. NK cells are defined as large granular lymphocytes and constitute the third kind of cells differentiated from the common lymphoid progenitor generating B and T lymphocytes. NK cells are known to differentiate and mature in the bone marrow, lymph node, spleen, tonsils and thymus where they enter into circulation. NK cells express usually the surface markers CD16 (FcγRIII) and CD56 in humans.

The terms "NL4-3" and "BaL", as used herein, refer to two different HIV isolates commonly used in the laboratory. The NL4-3 isolate was cloned from NY5 and LAV proviruses. See Adachi A, et al., J. Virol. 1986; 59:284-291. The BaL isolate was obtained from a primary culture of adherent cells grown from explanted lung tissue. See Gartner S, et al., Science 1986; 233:215-219.

The terms "nucleic acid", "polynucleotide" and "nucleotide sequence", as used interchangeably herein, relate to any polymeric form of nucleotides of any length and composed of ribonucleotides or deoxyribonucleotides. The terms include both single-stranded and double-stranded polynucleotides, as well as modified polynucleotides (e.g. methylated, protected). Typically, the nucleic acid is a "coding sequence" which, as used herein, refers to a DNA sequence that is transcribed and translated into a polypeptide in a host cell when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g. mammalian) DNA, and even synthetic DNA sequences. A transcription termination sequence will usually be located 3' to the coding sequence.

The term "operably linked", as used herein, means that the nucleotide sequence of interest is linked to the regulatory sequence(s) in a manner that allows for expression of the nucleotide sequence (e.g. in an in vitro transcription/translation system or in a host cell when the vector is introduced into the host cell). See Auer H, Nature Biotechnol. 2006; 24: 41-43.

The expression "panel of HIV isolates", as used herein, refers to a collection of reference HIV isolates designed for use as Env-pseudotyped viruses to facilitate standardized tier 2/3 assessments of neutralizing antibody responses. See Mascola R, et al., J. Virol. 2005; 79(16):10103. The pseudoviruses exhibit a neutralization phenotype that is typical of most primary HIV-1 isolates. The gp160 genes were cloned from sexually acquired, acute/early infections and comprise a wide spectrum of genetic, antigenic and geographic diversity within subtype B. These clones use CCR5 as co-receptor. See Li, et al., J. Virol. 2005; 79(16): 10108-10125.

The expression "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and, intrasternal injection and infusion.

The expression "pharmaceutically acceptable carrier", as used herein, includes any and all solvents, dispersion media, coatings, antibacterial and antifungal agents, isotonic and absorption delaying agents that are physiologically compatible with the antibody derivatives, nucleic acids, vectors and host cells of the invention.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The terms "prevent," "preventing" and "prevention", as used herein, refer to inhibiting the inception or decreasing the occurrence of a disease in a subject. The prevention may be complete (e.g. the total absence of pathological cells in a subject). The prevention may also be partial, such as, for example, lowering the occurrence of pathological cells in a subject. Prevention also refers to a reduced susceptibility to a clinical condition. Within the context of the present invention, the terms "prevent," "preventing" and "prevention", refer specifically to averting or reducing the probability of HIV infection in a subject sustaining HIV exposure.

The term "sample", as used herein, refers to any biofluid and, in particular, blood, serum, plasma, lymph, saliva, peripheral blood cells or tissue cells serum, semen, sputum, cephalorachidian liquid (CRL), tears, mucus, sweat, milk or brain extracts obtained from a subject. The bodily tissue may comprise thymus, lymph node, spleen, bone marrow or tonsil tissue. The term "sample" refers also to non-biological samples (e.g. obtained from water, beverages).

The term "subject", as used herein, refers to an individual, plant or animal, such as a human, a nonhuman primate (e.g. chimpanzees and other apes and monkey species); farm animals, such as birds, fish, cattle, sheep, pigs, goats and horses; domestic mammals, such as dogs and cats; laboratory animals including rodents, such as mice, rats and guinea pigs. The term does not denote a particular age or sex. The term "subject" encompasses an embryo and a fetus. In a preferred embodiment, the subject is a human.

The term "T-1249", a used herein, refers to a gp41-derived polypeptide of SEQ ID NO:8 covering part of the HR2 region of gp41. See Eggink, 2008, supra.

The term "T-20", a used herein, refers to a gp41-derived polypeptide of SEQ ID NO:7 covering part of the HR2 region of gp41, also known as enfuvirtide. See CAS [159519-65-0] and U.S. Pat. No. 5,464,933. This polypeptide has antiviral activity in the nanomolar range and has been used in therapy against HIV infection. See Zhang D, et al., Expert Opin Ther Pat. 2015; 25:159-173 and Eggink, 2008, supra.

The term "T-2635", a used herein, refers to a gp41-derived polypeptide of SEQ ID NO:10 covering part of the HR2 region of gp41. See Eggink, 2008, supra.

The term "therapeutic agent" as used herein, refers to an atom, molecule or compound useful in the treatment or prevention of a disease. Examples of therapeutic agents include, but are not limited to, antibodies, antibody fragments, HIV antiretrovirals, drugs, cytotoxic agents, pro-apopoptotic agents, toxins, nucleases (e.g. DNAses and RNAses), hormones, immunomodulators, chelators, boron compounds, photoactive agents or dyes, radionuclides, oligonucleotides, interference RNA, siRNA, RNAi, anti-angiogenic agents, chemotherapeutic agents, cytokines, chemokines, prodrugs, enzymes, binding proteins, peptides or combinations thereof.

The term "therapeutically effective amount", as used herein, refers to the dose or amount of the antibody derivatives, nucleic acids, vectors, pharmaceutical compositions of the invention or mixtures thereof that produces a therapeutic response or desired effect in a subject.

The terms "therapy" or "therapeutic", a used herein, refer to the use of the antibody derivatives, nucleic acids, vectors, pharmaceutical compositions of the invention or mixtures thereof for either the treatment or prevention of a disease including, but not limited to, HIV and AIDS.

The term "treat" or "treatment", as used herein, refers to the administration of an antibody derivative, nucleic acid, vector, host cell or pharmaceutical composition of the invention for controlling the progression of a disease after its clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state and remission (both partial and total). The control of progression of the disease also involves an extension of survival compared with the expected survival if treatment was not applied. Within the context of the present invention, the terms "treat" and "treatment" refer specifically to stopping or slowing the infection and destruction of healthy CD4+ T cells in a HIV infected subject. It also refers to the stopping and slowing of the onset of symptoms of the acquired immunodeficiency disease such as extreme low CD4+ T cell count and repeated infections by opportunistic pathogens. Beneficial or desired clinical results include, but are not limited to, an increase in absolute naïve CD4+ T cell count (range 10-3520), an increase in the percentage of CD4+ T cell over total circulating immune cells (range 1-50%), or an increase in CD4+ T cell count as a percentage of normal CD4+ T cell count in an uninfected subject (range 1-161%). "Treatment" can also mean prolonging survival of the infected subject as compared to expected survival if the subject does not receive any HIV targeted treatment.

The term "vector", as used herein, refers to a nucleic acid molecule, linear or circular, that comprises a nucleic acid of the invention operably linked to additional segments that provide for its autonomous replication in a host cell or according to the expression cassette of the nucleic acid molecule.

2. Antibody Derivatives

In a first aspect, the present invention refers to antibody derivatives which comprise from the N- to C-terminus:
 (a) the D1 and D2 extracellular domains of a human CD4 receptor,
 (b) the Fc portion of a human IgG,
 (c) a moiety selected from the group consisting of (i) a linker polypeptide of sequence $(GGGGS)_n$ wherein $1 \leq n \leq 10$, (ii) a human CCR5 receptor sequence and (iii) combinations thereof and
 (d) a gp41-derived polypeptide.

The antibody derivatives of the invention are characterized for having increased antiviral and ADCC activities.

In one embodiment, the D1 domain of the antibody derivatives of the invention comprises amino acids 26-125 of the human CD4 receptor (i.e. UniProtKB database accession number P01730) or a functionally equivalent variant thereof. In another embodiment, the D2 domain of the antibody derivatives comprises amino acids 126-203 of the human CD4 receptor or a functionally equivalent variant thereof. Preferably, the D1 and D2 domains comprise sequences SEQ ID NO:1 and SEQ ID NO:2, respectively, or a functionally equivalent variant thereof.

In a further embodiment, the Fc portion of the human IgG comprises the Fc portion of an IgG1, IgG2, IgG3 or IgG4 isotype. Preferably, the IgG isotype is IgG1. More preferably, the Fc portion of the human IgG comprises G236A, S239D, A330L and I332E point mutations or a functionally equivalent variant thereof. The Fc portion of the human IgG1 comprising SEQ ID NO:4 or a functionally equivalent variant thereof, is most preferred.

In another embodiment, the moiety of the antibody derivatives of the invention is selected from the group consisting of (i) a linker polypeptide of sequence $(GGGGS)_n$ (SEQ ID NO:5) wherein $1 \leq n \leq 10$, (ii) a human CCR5 receptor sequence, (iii) a combination of (i) and (ii) and a functionally equivalent variant of (i), (ii) and (iii). In one version of this embodiment, the moiety comprises only the linker or the human CCR5 receptor sequence or a functionally equivalent variant thereof. In another version of this embodiment, the moiety comprises a combination of the linker and the human CCR5 receptor sequence or a functionally equivalent variant thereof. Preferably, the linker is attached to the C-terminus of the human CCR5 receptor sequence when a combination is employed. Preferably, the moiety comprises the linker only or a combination of the linker and the human CCR5 receptor sequence or a functionally equivalent variant thereof. Preferably, the human CCR5 receptor sequence comprises SEQ ID NO:6 or a functionally equivalent variant thereof.

In a further embodiment, the gp41-derived polypeptide comprises the T-20, T-4912, C34, T-2635 polypeptide, their combinations or a functionally equivalent variant thereof. Preferably, the gp41-derived polypeptide comprises the T-20 polypeptide or a functionally equivalent variant thereof. More preferably, the T-20 polypeptide comprises SEQ ID NO:7.

In an additional embodiment, the antibody derivatives of the invention comprise MOLECULE-5, MOLECULE-6, MOLECULE-7, MOLECULE-8, MOLECULE-10, MOLECULE-11 or a functionally equivalent variant thereof. Preferably, the antibody derivatives comprise MOLECULE-5, MOLECULE-7, MOLECULE-8 or a functionally equivalent variant thereof. More preferably, the antibody derivatives comprise MOLECULE-7. In one version of this embodiment, MOLECULE-5, MOLECULE-6, MOLECULE-7, MOLECULE-8, MOLECULE-10 and MOLECULE-11 comprise sequences SEQ ID NO:16, SEQ ID NO:17, SEQ ID NO:18, SEQ ID NO:19, SEQ ID NO:20 and SEQ ID NO:21, respectively, or a functionally equivalent variant thereof.

Preferably, the antibody derivatives of the invention comprise:
 (1) (a) the D1 and D2 extracellular domains of a human CD4 receptor, (b) the Fc portion of a human IgG1, (c) a moiety selected from the group consisting of (i) a linker polypeptide of sequence $(GGGGS)_n$ wherein $1 \leq n \leq 10$, (ii) a human CCR5 receptor sequence and (iii)

combinations thereof, and (d) a gp41-derived polypeptide selected from the group consisting of T-20, T-1249, C34 and T-2635, wherein the IgG1 is wild-type or contain G236A, S239D, A330L and I332E point mutations, (2) (a) the D1 and D2 extracellular domains of a human CD4 receptor, (b) the Fc portion of a human IgG2, (c) a moiety selected from the group consisting of (i) a linker polypeptide of sequence (GGGGS)$_n$ wherein 1≤n≤10, (ii) a human CCR5 receptor sequence and (iii) combinations thereof, and (d) a gp41-derived polypeptide selected from the group consisting of T-20, T-1249, C34 and T-2635, (3) (a) the D1 and D2 extracellular domains of a human CD4 receptor, (b) the Fc portion of a human IgG3, (c) a moiety selected from the group consisting of (i) a linker polypeptide of sequence (GGGGS)$_n$ wherein 1≤n≤10, (ii) a human CCR5 receptor sequence and (iii) combinations thereof, and (d) a gp41-derived polypeptide selected from the group consisting of T-20, T-1249, C34 and T-2635, and (4) (a) the D1 and D2 extracellular domains of a human CD4 receptor, (b) the Fc portion of a human IgG4, (c) a moiety selected from the group consisting of (i) a linker polypeptide of sequence (GGGGS)$_n$ wherein 1≤n≤10, (ii) a human CCR5 receptor sequence and (iii) combinations thereof, and (d) a gp41-derived polypeptide selected from the group consisting of T-20, T-1249, C34 and T-2635.

More preferably, the antibody derivatives of the invention comprise: (a) the D1 and D2 extracellular domains of a human CD4 receptor, (b) the Fc portion of a human IgG1 containing G236A, S239D, A330L and I332E point mutations, (c) a moiety selected from the group consisting of (i) a linker polypeptide of sequence (GGGGS)$_n$ wherein 1≤n≤10, (ii) a human CCR5 receptor sequence and (iii) combinations thereof, and (d) a gp41-derived polypeptide selected from the group consisting of T-20, T-1249, C34 and T-2635.

The antibody derivatives of the invention are useful for preventing (i.e. neutralizing) the attachment of molecules (e.g. HIV) to the human CD4 receptor in cells expressing said cluster in their surface (e.g. T-helper cells, monocytes, macrophages, dendritic cells). Preferably, the antibody derivatives of the invention are utilized for preventing the attachment of gp160 proteins located in the viral envelope of HIV to human CD4 receptors found in T-helper cells. The neutralizing capacity of the antibody derivatives of the invention may be characterized by an IC$_{50}$ of 10 ng/mL or lower, and preferably, by an IC$_{50}$ of less than 5 ng/mL, less than 2.5 ng/mL, less than 1.25 ng/mL, less than 0.625 ng/mL, less than 0.312 µg/mL, less than 0.156 ng/mL, less than 0.07 ng/mL or less than 0.035 ng/mL.

In an additional embodiment, the antibody derivatives of the invention can be chemically modified by covalent conjugation to a polymer, for example, to increase their circulating half-life. Methods of attaching polypeptides to polymers are known in the art. See U.S. Pat. Nos. 4,766,106, 4,179,337, 4,495,285 and 4,609,546. Preferably, the polymers are polyoxyethylated polyols and polyethylene glycol (PEG). PEG is a water soluble polymer that has the general formula: R(O—CH$_2$—CH$_2$)$_n$O—R where R can be hydrogen or a protective group such as an alkyl or alkanol group. Preferably, the protective group has between 1 and 8 carbons, more preferably it is methyl. Preferably, n is an integer between 1 and 1,000 and, more preferably between 2 and 500. PEG has a preferred average molecular weight between 1,000 and 40,000, more preferably between 2,000 and 20,000 and most preferably between 3,000 and 12,000.

In a further embodiment, the antibody derivatives of the invention are attached to a therapeutic agent to form an antibody drug conjugate (ADC). For instance, therapeutic agents used for the treatment of opportunistic diseases and conditions arising from or favored by the inception of AIDS such as, for example, Kaposi's sarcoma, may be treated with an ADC formed by an antibody derivative of the invention and interferon-α, a liposomal anthracycline (e.g. Doxil) or paclitaxel. Further ADCs effective for the treatment of other opportunistic diseases, such as viral and bacterial infections (e.g. shingles, pneumonia, tuberculosis), skin diseases and other types of cancer (e.g. lymphoma) associated to AIDS, may also be devised by combining an antibody derivative of the invention and an appropriate therapeutic agent.

3. Nucleic Acids, Vectors and Host Cells

In another aspect, the present invention relates to nucleic acids encoding for the antibody derivative of the invention, and to the expression cassettes and vectors comprising said nucleic acids.

Preferably, the nucleic acids are polynucleotides, including, but not limited to, deoxyribonucleotides (DNA) and ribonucleotides (RNA) linked by internucleotide phosphodiester bond linkages. In a preferred embodiment, the nucleic acids of the invention comprise the polynucleotides encoding for the D1 and D2 extracellular domains of the human CD4 receptor (SEQ ID NO:22, SEQ ID NO:23), the Fc portion of the human IgG1 (SEQ ID NO:24), the linker polypeptide (SEQ ID NO:26), the human CCR5 receptor (SEQ ID NO:27), and the T-20 polypeptide (SEQ ID NO:28) or their functionally equivalent variants. Preferably, the nucleic acids of the invention encode for MOLECULE-5 (SEQ ID NO:37), MOLECULE-6 (SEQ ID NO:38), MOLECULE-7 (SEQ ID NO:39), MOLECULE-8 (SEQ ID NO:40), MOLECULE-10 (SEQ ID NO:41), MOLECULE-11 (SEQ ID NO:42) or a functionally equivalent variant thereof. The functionally equivalent variants of the nucleic acids of the invention may be obtained by means of the insertion, deletion or substitution of one or several nucleotides with respect to their reference sequences. Preferably, the polynucleotides encoding for functionally equivalent variants of the nucleic acids of the invention are polynucleotides whose sequences allows them to hybridize in highly restrictive conditions with their nucleic acids of reference. Typical conditions of highly restrictive hybridization include incubation in 6×SSC (1×SSC: 0.15 M NaCl, 0.015 M sodium citrate) and 40% formamide at 42° C. during 14 hours, followed by one or several washing cycles using 0.5×SSC, 0.1% SDS at 60° C. Alternatively, highly restrictive conditions include those comprising a hybridization at a temperature of approximately 50°–55° C. in 6×SSC and a final washing at a temperature of 68° C. in 1-3×SSC. Moderate restrictive conditions comprise hybridization at a temperature of approximately 50° C. until around 65° C. in 0.2 or 0.3 M NaCl, followed by washing at approximately 50° C. until around 55° C. in 0.2×SSC, 0.1% SDS (sodium dodecyl sulphate). In one further embodiment, the nucleic acids of the invention are codon optimized.

In another embodiment, a variant of a nucleic acid having at least 80%, 85%, 90%, 95%, or 99% similarity to its reference nucleic acid is used instead, wherein said variant encodes an antibody derivative of the invention or a functionally equivalent variant thereof.

The nucleic acids of the invention may require to be cut with restriction enzymes in order to be ligated into a vector (e.g. 1, 2 or 3 terminal nucleotides may be removed). In an additional embodiment, the invention relates to said nucleic acids, wherein they have been cut at each end with a restriction enzyme.

In another embodiment, the present invention relates to an expression cassette comprising a nucleic acid of the invention, a promoter sequence and a 3'-UTR and, optionally, a selection marker.

In yet another embodiment, the present invention relates to a vector comprising a nucleic acid of the invention. In an additional aspect of this embodiment, the nucleic acid of the invention is contained in an expression cassette comprised by said vector. Suitable vectors according to the present invention include, but are not limited to, prokaryotic vectors, such as pUC18, pUC19, and Bluescript plasmids and derivatives thereof, like the mp18, mp19, pBR322, pMB9, ColE1, pCR1 and RP4 plasmids; phages and shuttle vectors, such as pSA3 and pAT28 vectors; expression vectors in yeasts, such as 2-micron plasmid type vectors; integration plasmids; YEP vectors; centromeric plasmids and analogues; expression vectors in insect cells, such as the vectors of the pAC series and of the pVL series; expression vectors in plants, such as vectors of the pIBI, pEarleyGate, pAVA, pCAMBIA, pGSA, pGWB, pMDC, pMY, pORE series and analogues; and expression vectors in superior eukaryotic cells either based on viral vectors (e.g. adenoviruses, adeno-associated viruses, retroviruses, lentiviruses) as well as non-viral vectors, such as the pSilencer 4.1-CMV (Ambion®, Life Technologies Corp., Carlsbad, Calif., US), pcDNA3, pcDNA 3.1, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d, and pTDT1 vectors. Preferably, the vector is a pcDNA3.1 vector. More preferably, the vector is pABT-5, pABT-7 and pABT-8.

In an additional embodiment, the viral vector is an AAV vector. AAV vectors encoding the antibody derivatives of the invention may be constructed according to molecular biology techniques well known in the art. See Brown T, "Gene Cloning" (Chapman & Hall, London, G B, 1995); Watson R, et al., "Recombinant DNA", 2nd Ed. (Scientific American Books, New York, N.Y., US, 1992); Alberts B, et al., "Molecular Biology of the Cell" (Garland Publishing Inc., New York, N.Y., US, 2008); Innis M, et al., Eds., "PCR Protocols. A Guide to Methods and Applications" (Academic Press Inc., San Diego, Calif., US, 1990); Erlich H, Ed., "PCR Technology. Principles and Applications for DNA Amplification" (Stockton Press, New York, N.Y., US, 1989); Sambrook J, et al., "Molecular Cloning. A Laboratory Manual" (Cold Spring Harbor Laboratory Press, Cold Spring Harbor, N.Y., US, 1989); Bishop T, et al., "Nucleic Acid and Protein Sequence. A Practical Approach" (IRL Press, Oxford, G B, 1987); Reznikoff W, Ed., "Maximizing Gene Expression" (Butterworths Publishers, Stoneham, Mass., US, 1987); Davis L, et al., "Basic Methods in Molecular Biology" (Elsevier Science Publishing Co., New York, N.Y., US, 1986), Schleef M, Ed., "Plasmid for Therapy and Vaccination" (Wiley-VCH Verlag GmbH, Weinheim, Del., 2001).

For instance, HEK-293 cells (expressing E1 genes), a helper plasmid providing adenovirus function, a helper plasmid providing AAV rep genes from serotype 2 and cap genes from the desired serotype (e.g. AAV8) and, finally, the backbone plasmid with ITRs and the construct of interest (e.g. MOLECULE-5, MOLECULE-7), may be employed. To generate an AAV vector expressing the antibody derivative of the invention, the cDNA of the antibody derivative may be cloned into an AAV backbone plasmid under the control of a ubiquitous (e.g. CAG) or a cell-specific promoter.

AAV vectors (viral vector particles) may be generated by helper virus-free transfection of HEK293 cells using three plasmids with modifications. See Matsushita T, et al., Gene Ther. 1998; 5:938-945 and Wright J, et al., Mol. Ther. 2005; 12:171-178. Cells may be cultured to 70% confluence in roller bottles (RB) (Corning Inc., Corning, N.Y., USA) in DMEM (Dulbeccos's Modified Eagle Medium) supplemented with 10% BFS (bovine fetal serum) and then co-transfected with: 1) a plasmid carrying the expression cassette flanked by the viral ITRs (described above); 2) a helper plasmid carrying the AAV rep2 and the correspondent cap (cap1 and cap9 genes; and 3) a plasmid carrying the adenovirus helper functions. Vectors may then be purified by two consecutives cesium chloride gradients using either a standard protocol or an optimized protocol as previously described. See Ayuso E, et al., Gene Ther. 2010; 17:503-510. Vectors may be further dialyzed against PBS, filtered, titred by qPCR (quantitative polymerase chain reaction) and stored at −80° C. until use.

In another embodiment, the present invention relates to a host cell comprising a nucleic acid, expression cassette or vector of the invention. Host cells to be used according to the present invention can be of any cell type, including both eukaryotic cells and prokaryotic cells. Preferably, the cells include prokaryotic cells, yeast cells or mammalian cells. More preferably, the host cells are HEK-293 and CHO cells.

4. Pharmaceutical Compositions

In a further aspect, the present invention refers to a pharmaceutical composition containing at least one of the antibody derivatives, nucleic acids, vectors or host cells of the invention (hereinafter referred singly or jointly as "active agent(s) of the invention") or a mixture thereof, formulated with a pharmaceutically acceptable carrier. Said pharmaceutical compositions are used for treating HIV or AIDS in a subject or preventing HIV infection in an uninfected subject. In one embodiment, the compositions include a mixture of multiple (e.g. two or more) antibody derivatives, nucleic acids, vectors or host cells of the invention.

In one embodiment of the invention, the composition comprises at least MOLECULE-3, MOLECULE-4, MOLECULE-5, MOLECULE-6, MOLECULE-7, MOLECULE-8, MOLECULE-10, MOLECULE-11 or the nucleic acids, vectors or host cells expressing said antibody derivatives or a mixture thereof. Preferably, the composition comprises at least MOLECULE-5, MOLECULE-7, MOLECULE-8 or the nucleic acids, vectors or host cells expressing said antibody derivatives or a mixture thereof. More preferably, the composition comprises at least MOLECULE-7 or the nucleic acids, vectors or host cells expressing said antibody derivative or a mixture thereof. The preparation of pharmaceutical compositions comprising the antibody derivatives of the invention is known in the art. See McNally E, et al., Eds., "Protein Formulation and Delivery" (Marcel Dekker, Inc., New York, N.Y., USA, 2000), Hovgaard L, et al., Eds., "Pharmaceutical Formulation Development of Peptides and Proteins", $2^{nd}$ Ed. (CRC Press, Boca Raton, Fla., USA, 2012) and Akers M, et al., Pharm Biotechnol. 2002; 14:47-127.

Preferably, the carrier is suitable for intravenous, intramuscular, subcutaneous, parenteral, spinal or epidermal administration (e.g. by injection or infusion). Depending on the route of administration, the active agent of the invention may be coated in a material to protect the agent from the action of conditions that may inactivate the agent.

In a further embodiment of the present invention, pharmaceutical compositions specifically suitable for gene therapy ("passive immunization") are provided. Said pharmaceutical compositions comprise at least one of the nucleic acids or vectors of the invention or their mixture and are prepared according to methods known in the art. See Andre S, et al., J. Virol, 1998, 72:1497-1503; Mulligan M, Webber J, AIDS 1999; 13(Suppl A):5105-S112; O'Hagan D, et al., J. Virol. 2001; 75:9037-9043 and Rainczuk A, et al., Infect. Immun. 2004; 72:5565-5573. The particular vector backbone into which the nucleic acids of the invention are inserted is not important as long as said nucleic acid is adequately expressed in a subject. Examples of suitable vectors include, but are not limited to, viruses and plasmids. Preferably, an AAV vector is used when a viral vector is employed. Preferably, a pcDNA3. L and pVAX1 (Invitrogen, Carlsbad, CA, USA); DNA sequences available at the Invitrogen website www.thermofisher.com/uk/en/home/brands/3nvitrogen, October 2015); pNGVL (National Gene Vector Laboratory, University of Michigan, MI, USA); and p414cyc (ATCC accession number 87380) and p414GALS (ATCC accession number 87344) is used when a plasmidic vector is employed. More preferably, a pcDNA3.1 plasmid is utilized as plasmidic vector. Most preferably, the plasmidic vector is pABT-5, pABT-7 and pABT-8.

The design and applications of passive immunization are known in the art. See Donnelly J, et al., Annu. Rev. Immunol. 1997; 15:617-648; Robinson H, Pertmer T, Adv. Virus Res. 2000; 55:1-74; Gurunathan S, et al., Annu. Rev. Immunol. 2000; 18:927-974 (2000) and Ulmer J, Curr. Opin. Drug Discov. Devel. 2001; 4:192-197. Briefly, passive immunization within the context of the present invention is configured to direct the in vivo expression of an antibody derivative in a subject. See Ulmer J, et al., Science 1993; 259: 1745-1749. Typically, the nucleic is cloned into a bacterial plasmid that is optimized for expression in eukaryotes and consists of the following: (i) an origin of replication for propagation in bacteria, usually an $E.$ $coli$ origin such as ColE1, (ii) an antibiotic resistance gene, usually kanamycin, for selection of the plasmid in bacteria, (iii) a strong promoter for optimal expression in mammalian cells like cytomegalovirus (CMV) or simian virus 40 (SV40), (iv) multiple cloning site downstream of the promoter for insertion of the gene of interest and (v) SV40 or bovine growth hormone (BGH) polyadenylation signal for stabilization of mRNA.

Still another object of the present invention is to deliver vectors utilizing non-pathogenic or attenuated bacterial strains harboring plasmids capable of expressing the antibody derivatives of the invention, such as, but not restricted to, *Escherichia* spp., *Salmonella* spp., *Shigella* spp., *Mycobacterium* spp. and *Listeria* spp.

The particular *Escherichia* strain employed is not critical to the present invention. Examples of *Escherichia* strains which can be employed in the present invention include *Escherichia coli* strains DH5a, HB 101, HS-4, 4608-58, 1184-68, 53638-C-17, 13-80, and 6-81, enterotoxigenic *E. coli*, enteropathogenic *E. coli* and enterohemorrhagic *E. coli*. See Sambrook, 1989, supra; Sansonetti P, et al., Ann. Microbiol. 1982; 132A:351-355); Evans D, et al., Infect. Immun. 1975; 12:656-667; Donnenberg S, et al., J. Infect. Dis. 1994; 169:831-838 and McKee M, O'Brien A, Infect. Immun. 1995; 63:2070-2074.

The particular *Salmonella* strain employed is not critical to the present invention. Examples of *Salmonella* strains that can be employed in the present invention include *S. typhi* (ATCC accession number 7251), *S. typhimurium* (ATCC accession number 13311), *S. galinarum* (ATCC accession number 9184), *S. enteriditis* (ATCC accession number 4931), *S. typhimurium* (ATCC accession number 6994), *S. typhi* aroC, aroD double mutant (Hone D, et al., Vaccine 1991; 9:810-816) and *S. typhimurium* aroA mutant (Mastroeni D, et al., Micro. Pathol. 1992; 13:477-491).

The particular *Shigella* strain employed is not critical to the present invention. Examples of *Shigella* strains that can be employed in the present invention include *S. flexneri* (ATCC accession number 29903), *S. flexneri* CVD1203 (ATCC accession number 55556), *S. flexneri* 15D (Sizemore D, et al., Vaccine 1997; 15:804-807; Sizemore D, et al., Science 1995, 270:299-302), *S. sonnei* (ATCC accession number 29930) and *S. dysenteriae* (ATCC accession number 13313).

The particular *Mycobacterium* strain employed is not critical to the present invention. Examples of *Mycobacterium* strains that could be employed in the present invention include *M. tuberculosis* CDC1551 strain (Griffith T, et al., Am. J. Respir. Crit. Care Med. 1995; 152:808-811), *M. tuberculosis* Beijing strain (van Soolingen D, et al., J. Clin. Microbiol. 1995; 33:3234-3238), *M. tuberculosis* H37Rv strain (ATCC accession number 25618), *M. tuberculosis* pantothenate auxotroph strain (Sambandamurthy V, Nat. Med. 2002; 8:1171-1174, *M. tuberculosis* rpoV mutant strain (Collins D, et al., Proc. Natl. Acad. Sci USA. 1995; 92: 8036, *M. tuberculosis* leucine auxotroph strain (Hondalus M, et al., Infect. Immun. 2000; 68(5):2888-2898), BCG Danish strain (ATCC accession number 35733), BCG Japanese strain (ATCC accession number 35737), BCG, Chicago strain (ATCC accession number 27289), BCG Copenhagen strain (ATCC No. 27290), BCG Pasteur strain (ATCC accession number 35734), BCG Glaxo strain (ATCC accession number 35741), BCG Connaught strain (ATCC accession number 35745) and BCG Montreal (ATCC accession number 35746).

The particular *Listeria* strain employed is not critical to the present invention. Examples of *Listeria monocytogenes* strains which can be employed in the present invention include, but are not restricted to, *L. monocytogenes* strain 10403 S (Stevens R, et al., J. Virol. 2004; 78:8210-8218), *L. ivanovii* and *L. seeligeri* strains (Haas A, et al., Biochim. Biophys. Acta. 1992; 1130:81-84) or mutant *L. monocytogenes* strains such as (i) actA plcB double mutant (Peters C, et al., FEMS Immunol. Med. Microbiol. 2003; 35:243-253 and Angelakopoulos H, et al., Infect. Immun. 2002; 70:3592-3601) or (ii) dal dat double mutant for alanine racemase gene and D-amino acid aminotransferase gene (Thompson R, et al., Infect. Immun. 1998; 66:3552-3561).

Methods for delivering vectors using bacterial vehicles are well known in the art. See U.S. Pat. Nos. 6,500,419, 5,877,159 and 5,824,538; Shata M, et al., Mol. Med. Today 2000; 6:66-71; Hone D, Shata M, J. Virol. 2001; 75:9665-9670; Shata M, et al., Vaccine 2001; 20:623-629; Rapp U and Kaufmann S, Int. Immunol. 2004, 16:597-605; Dietrich G, et al., Curr. Opin. Mol. Ther. 2003; 5:10-19 and Gentschev I, et al., J. Biotechnol. 2000; 83:19-26. The type of plasmid delivered by said bacterial vehicles for expressing the antibody derivatives of the invention is not critical.

In an additional embodiment, the use of an AAV vector for delivering the nucleic acids of the invention is also provided.

The pharmaceutical compositions of the present invention can be administered by a variety of methods known in the art. As will be appreciated by the skilled artisan, the route or mode of administration will vary depending upon the desired results. The active agents of the invention can be prepared with carriers that will protect the agent against rapid release, such as a controlled release formulation, including implants, transdermal patches and microencapsulated delivery systems. Biodegradable, biocompatible polymers can be used, such as ethylene vinyl acetate, polyanhydrides, polyglycolic acid, collagen, polyorthoesters and polylactic acid. Many methods for the preparation of such formulations are generally known to in the art. See Robinson J, et al., Eds., "Sustained and Controlled Release Drug Delivery Systems" (Marcel Dekker, Inc., New York, N.Y., USA, 1978).

To administer an active agent of the invention by certain routes of administration, it may be necessary to coat the agent with, or co-administer the agent with, a material to prevent its inactivation or to ensure its proper distribution in vivo. For example, the agent may be administered to a subject in an appropriate carrier (e.g. liposome) or a diluent. Pharmaceutically acceptable diluents include, but are not limited to, saline and aqueous buffer solutions. Liposomes include water-in-oil-in-water CGF emulsions as well as conventional liposomes. See Strejan G, et al., J. Neuroimmunol. 1984; 7:27-41. Many methods of manufacturing liposomes are known in the art. See U.S. Pat. Nos. 4,522, 811, 5,374,548 and 5,399,331. The liposomes may comprise one or more moieties which are selectively transported into specific cells or organs and thus enhance targeted drug delivery. Exemplary targeting moieties include folate or biotin, mannosides and surfactant protein A receptor. In one embodiment of the invention, the active agents of the invention are formulated in liposomes; in a more preferred embodiment, the liposomes include a targeting moiety. In a most preferred embodiment, the active agents in the liposomes are delivered by bolus injection.

Pharmaceutically acceptable carriers include sterile aqueous solutions or dispersions and sterile powders for the extemporaneous preparation of sterile injectable solutions or dispersions. The use of such media in the preparation of the pharmaceutical compositions of the invention is contemplated herein in so far as their use is not incompatible with the active agents of the invention. Supplementary active compounds can also be incorporated into the pharmaceutical compositions.

Pharmaceutical compositions are typically sterile and stable under the conditions of manufacture and storage. The composition can be formulated as a solution, microemulsion, liposome or other ordered structure suitable to active agent concentration. The carrier can be a solvent or dispersion medium containing, for example, water, ethanol, polyol (e.g. glycerol, propylene glycol, liquid polyethylene glycol) or suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, such as, for example, sugars, polyalcohols (e.g. mannitol, sorbitol) or sodium chloride in the composition. Prolonged absorption of the injectable compositions can be brought about by including in the composition compounds that delay absorption (e.g. monostearate salts, gelatin).

Sterile injectable solutions can be prepared by incorporating the active agent of the invention in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (i.e. lyophilization) that yield a powder of the active ingredient plus any additional desired ingredient from a previously sterile-filtered solution thereof.

Dosage regimens are adjusted to provide the optimum desired response (e.g. a therapeutic response). For example, a single bolus may be administered, several divided doses may be administered over time or the dose may be proportionally reduced or increased, as indicated by the exigencies of the therapeutic situation. For example, the antibody derivatives of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active agent calculated to produce the desired therapeutic effect in association with the required pharmaceutical carrier. The specification for the dosage unit forms of the invention are dictated by and directly dependent on the unique characteristics of the active agent and the particular therapeutic effect to be achieved.

Examples of pharmaceutically-acceptable antioxidants include, but are not limited to, water soluble antioxidants (e.g. ascorbic acid, cysteine hydrochloride, sodium bisulfate, sodium metabisulfite, sodium sulfite), oil-soluble antioxidants (e.g. ascorbyl palmitate, butylated hydroxyanisole (BHA), butylated hydroxytoluene (BHT), lecithin, propyl gallate, alpha-tocopherol) and metal chelating agents (e.g. citric acid, ethylenediamine tetraacetic acid (EDTA), sorbitol, tartaric acid, phosphoric acid). The formulations of the pharmaceutical compositions of the invention include those suitable for oral, nasal, topical (e.g. buccal and sublingual), rectal, vaginal or parenteral administration. The formulations may conveniently be presented in unit dosage form and may be prepared by any methods known in the art. The amount of active agent which can be combined with a carrier material to produce a single dosage form will vary depending upon the subject being treated and the particular mode of administration. The amount of active agent which can be combined with a carrier material to produce a single dosage form will generally be that amount of the composition which produces a therapeutic effect. Generally, this amount will range from about 0.001% to about 90% of active agent, preferably from about 0.005% to about 70% and, most preferably, from about 0.01% to about 30%.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active agent of the invention may be mixed under sterile conditions with a pharmaceutically acceptable carrier and with any preservatives, buffers or propellants which may be required.

The pharmaceutical compositions of the invention may also contain adjuvants such as preservatives, wetting agents, emulsifying agents and dispersing agents. Prevention of presence of microorganisms may be ensured both by sterilization procedures and by the inclusion of various antibacterial and antifungal agents (e.g. paraben, chlorobutanol, phenol sorbic acid). It may also be desirable to include isotonic agents (e.g. sugars, sodium chloride) into the compositions.

Actual dosage levels of the active agents in the pharmaceutical compositions of the present invention may be varied so as to achieve the desired therapeutic response in a subject. The selected dosage level will depend upon a variety of pharmacokinetic factors including the activity of the particular agent of the invention employed, its amount, the route of administration, the time of administration, the rate of excretion or expression of the particular active agent employed, the duration of the treatment, other drugs, compounds or materials used in combination with the particular pharmaceutical compositions employed, the age, sex, weight, condition, general health and prior medical history of the subject being treated and other similar factors known in the medical arts. A physician or veterinarian having ordinary skill in the art can readily determine and prescribe the therapeutically effective amount of the active agent(s) required. For example, the physician or veterinarian could start doses of the active agents of the invention employed in the pharmaceutical composition at levels lower than that required in order to achieve the desired therapeutic effect and gradually increase the dosage until the desired effect is achieved. In general, a suitable daily dose of a composition of the invention will be that amount of the active agent which is the lowest dose effective to produce a therapeutic effect. Such an effective dose will generally depend upon the factors described above. It is preferred that administration be parenteral, more preferably intravenous, intramuscular, intraperitoneal or subcutaneous. If desired, the effective daily dose of a pharmaceutical composition may be administered as two, three, four, five, six or more sub-doses applied separately at appropriate intervals throughout the day, optionally, in unit dosage forms. While it is possible for an active agent of the invention to be administered alone, it is preferable to administer said agent as a pharmaceutical composition.

The pharmaceutical compositions of the invention can be administered with medical devices known in the art. For example, in a preferred embodiment, the pharmaceutical composition of the invention can be administered with a needleless hypodermic injection device. See U.S. Pat. Nos. 5,399,163, 5,383,851, 5,312,335, 5,064,413, 4,941,880, 4,790,824 or U.S. Pat. No. 4,596,556. Examples of well-known implants and modules useful in the present invention include, but are not limited to, infusion pumps for dispensing medications at different rates (e.g. U.S. Pat. No. 4,447,233 (non-implantable, controlled rate), U.S. Pat. No. 4,447,224 (implantable, variable rate), U.S. Pat. No. 4,487,603 (implantable, controlled rate)), devices for administering medicaments through the skin (e.g. U.S. Pat. No. 4,486,194) and osmotic drug delivery systems (e.g. U.S. Pat. Nos. 4,439,196 and 4,475,196). Many other such implants, delivery systems and modules are known to those skilled in the art.

The pharmaceutical compositions of the invention must be sterile and fluid to the extent that the composition is deliverable by syringe. In addition to water, the carrier can be an isotonic buffered saline solution, ethanol, polyol (e.g. glycerol, propylene glycol, liquid polyetheylene glycol) and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols (e.g. mannitol, sorbitol) and sodium chloride in the composition. Long-term absorption of the injectable compositions can be brought about by including an agent which delays absorption (e.g. aluminum monostearate, gelatin) in the composition.

5. Methods of Treatment and Prevention

In another aspect, the invention is directed to a method for either treating or preventing HIV infection or AIDS in a subject which comprises the administration to said subject of at least one of the antibody derivatives, nucleic acids, vectors, host cells or pharmaceutical compositions of the invention, or a mixture thereof. The beneficial treatment or preventive effects of the active agents and pharmaceutical compositions of the invention in relation to HIV infection or AIDS symptoms include, for example, preventing or delaying initial infection of a subject exposed to HIV, reducing viral burden in a subject infected with HIV, prolonging the asymptomatic phase of HIV infection, maintaining low viral loads in HIV infected subjects whose virus levels have been lowered via anti-retroviral therapy (AT), increasing levels of CD4 T cells or lessening the decrease in CD4 T cells, both HIV-1 specific and non-specific, in drug naive subjects and in subjects treated with AT, increasing overall health or quality of life in a subject with AIDS and prolonging the life expectancy of a subject with AIDS. A physician or veterinarian can compare the effect of the treatment with the subject's condition prior to treatment, or with the expected condition of an untreated subject, to determine whether the treatment is effective in inhibiting AIDS. In a preferred embodiment, the active agents and pharmaceutical compositions of the invention are used for the prevention of HIV infection or AIDS. In another preferred embodiment, the active agents and pharmaceutical compositions of the invention are used for the treatment of HIV infection or AIDS.

The active agents and pharmaceutical compositions of the invention may be useful in the treatment of HIV infection or AIDS. While all subjects that can be afflicted with HIV or their equivalents can be treated in this manner (e.g. chimpanzees, macaques, baboons or humans), the active agents and pharmaceutical compositions of the invention are directed particularly to their therapeutic uses in humans. Often, more than one administration may be required to bring about the desired therapeutic effect; the exact protocol (dosage and frequency) can be established by standard clinical procedures.

The present invention further relates to reducing or eliminating the symptoms associated with HIV infection or AIDS. These include symptoms associated with the minor symptomatic phase of HIV infection, including, for example, shingles, skin rash and nail infections, mouth sores, recurrent nose and throat infection and weight loss. In addition, further symptoms associated with the major symptomatic phase of HIV infection, include, for instance, oral and vaginal thrush (*Candida*), persistent diarrhea, weight loss, persistent cough and reactivated tuberculosis or recurrent herpes infections, such as cold sores (herpes simplex). Other symptoms of full-blown AIDS which can be treated in accordance with the present invention include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii* pneumonia (PCP), herpes zoster (or shingles), nervous system problems, such as pains, numbness or "pins and needles" in the hands and feet, neurological abnormalities, Kaposi's sarcoma, lymphoma, tuberculosis or other similar opportunistic infections.

In another preferred embodiment, the active agents or pharmaceutical compositions of the invention are administered to an HIV-infected subject or a subject exposed to HIV in combination with at least one therapeutic agent. Preferably, the therapeutic agent is indicated commonly for the prevention or treatment of HIV or AIDS. Suitable therapeutic agents include, but are not limited to, drugs forming part of current antiretroviral therapy (AT) and highly active antiretroviral therapy (HAART) protocols such as non-nucleoside reverse transcriptase inhibitor (e.g. efavirenz, nevirapine, delavirdine, etravirine, rilpivirine), nucleoside analogue reverse transcriptase inhibitors (e.g. zidovudine, tenofovir, lamivudine, emtricitabine) and protease inhibitors (e.g. saquinavir, ritonavir, indinavir, nelfinavir, amprenavir), referred hereinafter independently or jointly as "HIV antiretroviral(s)". In one version of this embodiment, at least one active agent or pharmaceutical composition of the invention and at least one HIV antiretroviral are administered to the subject together at the same time. In another version, at least one active agent or pharmaceutical composition of the invention is administered before any HIV antiretroviral is applied to the subject. In yet another version, at least one active agent or pharmaceutical composition of the invention is administered after a HIV antiretroviral has been applied to the subject, such as, for example, after the interruption of an AT or HAART protocol.

Additionally, the antibody derivatives of the invention can be also administered with therapeutic agents that may induce the expression of HIV gp120 on the surface of latently infected cells, thus allowing their quick removal by NK cells. See Siliciano J, et al, J Allergy Clin Immunol. 2014; 134(1):12-19.

6. Neutralization and Detection Methods

In an additional aspect, the present invention relates to a method of inactivating HIV which comprises the step of contacting the virus with at least one antibody derivative of the invention. Preferably, the method is carried out over a sample containing HIV or suspected of containing HIV. The method may be conducted under conditions that favor the coupling of the antibody derivative to HIV as described in the art. See Lu L, et al., Retrovirology 2012; 9(104), 1-14.

In a further aspect, the present invention relates to a method of detecting a molecule or a fragment thereof (e.g. HIV, gp120) that attaches to the D1 and D2 domains of the human CD4 receptor in a sample which comprises the steps of (a) contacting the sample with an antibody derivative of the invention and (b) determining whether the antibody derivative specifically binds to a molecule in the sample. The sample may be a biological sample including, but not limited to, blood, serum, urine, tissue or other biological material from non-infected, infected or potentially infected subjects (e.g. subjects sustaining periodic or intermittent HIV exposure). The sample may also be non-biological (e.g. obtained from water, beverages). Preferably, the molecule is HIV and, more preferably, the gp120 viral envelope protein of HIV.

In a preferred embodiment of this aspect, the present invention relates to a method of detecting HIV in a sample which comprises the steps of (a) contacting the sample with an antibody derivative of the invention and (b) determining whether the antibody derivative specifically binds to a HIV molecule in the sample. Preferably, the sample is a plasma sample or a serum sample.

A sample may be first manipulated to make it more suitable for the method of detection. In a preferred embodiment, the contact between the sample and the antibody derivative is prolonged (i.e. an incubation under conditions suitable for the stability of the sample and the antibody derivative). The conditions during the contacting step can be determined in a routine manner by the skilled artisan. Suitable buffers that can be used in the contacting step include physiological buffers that do not interfere with the assay to be performed. For example, a Tris or a triethanolamine (TEA) buffer can be employed. The pH of the buffer (and resulting lysis reagent including the buffer solution) can range from about 2.0 to about 10.0, optionally from about 4.0 to about 9.0, preferably from about 7.0 to about 8.5 and even more preferably from about 7.5 to about 8.0, or, about 7.0, about 7.5, about 8.0, or about 8.5. Exemplary "contacting" conditions may comprise incubation for 15 minutes to 4 hours (e.g. 1 hr at 4° C., 37° C. or at room temperature). However, these may be varied as appropriate according to, for example, the nature of the interacting binding partners. The sample may optionally be subjected to gentle rocking, mixing or rotation. In addition, other appropriate reagents such as blocking agents to reduce non-specific binding may be added. For example, 1-4% BSA or other suitable blocking agent (e.g. milk) may be used. The contacting conditions can be varied and adapted depending on the aim of the detection method. For example, if the incubation temperature is, for example, room temperature or 37° C., this may increase the possibility of identifying binders which are stable under these conditions (e.g. stable under conditions found in the human body).

Preferably, the antibody derivatives of the invention are contacted with the sample under conditions which allow the formation of a complex between the antibody derivative and a molecule or fragment thereof present in the sample. The formation of a complex indicating, for example, the presence of HIV in the sample is then detected and measured by suitable means. These means of detection and measurement depend on the nature of the binding partners and include, but are not limited to, homogeneous and heterogeneous binding assays such as, for example, radio-immunoassays (RIA), ELISA, immunofluorescence, immunohistochemistry, flow cytometry (e.g. FACS), BIACORE and Western blot analyses. Preferred assay techniques, especially for large-scale analysis of subject sera and blood and blood-derived products, are flow cytometry, ELISA and Western blot techniques.

In a preferred embodiment, the measuring is performed by flow cytometry (e.g. FACS). As used herein, the term "flow cytometry" refers to an assay in which the proportion of a material in a sample is determined by labeling the material (e.g. by binding a labeled antibody to the material), causing a fluid stream containing the material to pass through a beam of light, separating the light emitted from the sample into constituent wavelengths by a series of filters and mirrors and detecting the light. Flow cytometry permits sensitive detection and rapid quantification of some features of single cells, such as relative size complexity and endogenous fluorescence, as well as the quantitative analysis of any cellular compound that can be labeled with a fluorochrome. See Melamed M, et al., "Flow Cytometry and Cell Sorting", 2nd Ed. (Wiley-Liss, New York, N.Y., USA, 1990). One of the main advantages of flow cytometry is the rapid quantification of analytes on a large number of particles or cells. Generally, the fluorochromes selected for use as detectable markers are selected based on their ability to fluoresce when excited by light with the wavelength used by the laser. When the fluorochrome is excited by the laser beam, it emits light which is then assessed by the photomultiplier tubes of the flow cytometer. This technique is capable of analyzing 10,000 cells/particles within 1 to 2 minutes. Flow cytometers have filters to detect the emittance from various fluorochromes which fluoresce at different wavelengths and allow for four or more different fluorochromes to be used as detectable markers, which means currently at least 4 different molecules may be detected simultaneously. These methods and apparatus for analyzing sample are commercially available and are well known in the art (e.g. FACSCalibur Flow Cytometer; BD Biosciences Corp., Franklin Lakes, N.J., USA).

In a preferred embodiment, said measuring comprises the analysis of the sample, preferably by flow cytometry using a reporter capable of binding to the antibody derivative, preferably, to the Fc region of said antibody derivative. Preferably, the reporter comprises a detectable moiety and, more preferably, it is a Fc-specific secondary antibody coupled to a detectable moiety.

Useful detectable moieties include fluorophores. By "fluorophore" (or "fluorochrome" or "chromophore") it is understood a fluorescent compound that can re-emit light upon light excitation. Fluorophores that can be used include biological (e.g. proteins) and chemical fluorophores. Exemplary biological fluorophores comprise T-sapphire, Cerulean, mCFPm, CyPet, EGFP, PA-EGFP, Emerald, EYFP, Venus, mCitrine, mKO, mOrange, DSRed, JRed, mStrawberry, mCherry, PA-mCherry, mRuby, Tomato, mPlum, mKate, mKatushka, Kaede, Halotag, and superecliptic fluorine. Exemplary chemical fluorophores comprise Alexafluor, Rhodamine, BODIPY, Tetramethylrhodamine, Cyanin dyes, Fluorescein, Quantum dots, IR dyes, FM dyes, ATTO dye. A secondary antibody can also be labeled with enzymes that are useful for detection, such as, for example, horseradish peroxidase, β-galactosidase, luciferase, alkaline phosphatase or glucose oxidase. When an antibody is labeled with a detectable enzyme, it can be detected by adding additional reagents that the enzyme uses to catalyze a reaction product that can be discerned. For example, when the agent horseradish peroxidase is present, the addition of hydrogen peroxide and diaminobenzidine leads to a colored reaction product, which is visually detectable. An antibody may also be labeled with biotin and detected through indirect measurement of avidin or streptavidin binding. It should be noted that the avidin itself can be labeled with an enzyme or a fluorescent label.

Preferably, the Fc secondary antibody employed is specific for the species from which the primary antibody is derived (e.g. human). In one embodiment, said Fc-specific secondary antibody is selected from the group consisting of IgA (e.g. IgA1, IgA2), IgD, IgE, IgG (e.g. IgG1, IgG2, IgG3, IgG4) and IgM. Preferably, the secondary antibody is IgG and, more preferably, IgG1. Said Fc-specific secondary antibody can be any vertebrate antibody, preferably any mammal antibody and, more preferably, any non-human antibody (e.g. a rabbit, mouse, rat, goat, horse, sheep or donkey antibody).

For use as reagents in the aforementioned assays, the antibody derivatives of the invention may be conveniently bonded to the inside surface of microtiter wells. The antibody derivatives of the invention may be directly bonded to the microtiter well. However, maximum binding of the antibody derivatives to the wells might be accomplished by pre-treating the wells with polylysine prior to the addition of the antibody derivatives. Furthermore, the antibody derivatives of the invention may be covalently attached to the wells by means known in the art. Generally, the antibody derivatives of the invention are used between 0.01 to 100 µg/mL for coating, although higher as well as lower amounts may also be used. Samples are then added to the wells coated with the antibody derivatives of the invention.

7. Kits

In a further aspect, the present invention refers to kits comprising at least one of the antibody derivatives, nucleic acids, vectors, host cells, pharmaceutical compositions or combinations of the invention or mixtures thereof. The components of the kits of the invention may be optionally packed in suitable containers and be labeled for the detection, inactivation, diagnosis, prevention or treatment of HIV or AIDS or their related conditions. The components of the kits may be stored in unit or multi-dose containers as an aqueous, preferably sterile, solution or as a lyophilized, preferably sterile, formulation for reconstitution. The containers may be formed from a variety of materials such as glass or plastic and may have a sterile access port (e.g. the container may be an intravenous solution bag or a vial having a stopper pierceable by a hypodermic injection needle). The kits may further comprise more containers comprising a pharmaceutically acceptable carrier. They may further include other materials desirable from a commercial and user standpoint, including, but not limited to, buffers, diluents, filters, needles, syringes, culture medium for one or more of the suitable host cells or other active agents. The kits can contain instructions customarily included in commercial packages of diagnostic and therapeutic products that contain information, for example, about the indications, usage, dosage, manufacture, administration, contraindications or warnings concerning the use of such diagnostic and therapeutic products.

All publications mentioned herein are incorporated in their entirety by reference. Having now generally described the invention, the same will be more readily understood through reference to the following examples, which are provided by way of illustration and are not intended to be limiting of the present invention, unless specified.

General Procedures

1. Construction of CD4-huIgG Derivatives

The two extracellular domains of human CD4 molecule (D1 and D2) were joined to the Fc portion of the human IgG1, which include the hinge, CH2 and CH3 domains, to yield a CD4-IgG1 molecule. Based on the CD4-IgG1 scaffold, antibody derivatives were designed with the following characteristics:

(a) Mutations in positions G236A/S239D/A330L/I332E of the Fc chain to increase ADCC mediated responses. See Bournazos S, et al., Cell 2014; 158:1243-1253.

(b) Addition of the N-terminal extracellular sequence of human CCR5 at the C-terminus of the Fc chain (MDYQVSSPIYDINYYTSEPCQKINVKQIA) (SEQ ID NO:6)

(c) Addition of the T-20 sequence at the C-terminus of the Fc chain (YTSLIHSLIEESQNQQEKKNEQELLELDKASLWNWF) (SEQ ID NO:7)

(d) Sequential addition of the CCR5 sequence (MDYQVSSPIYDINYYTSEPCQKINVKQIA) (SEQ ID NO:6) and the T-20 sequence (YTSLIHSLIEESQNQQEKKNEQELLELDKASLWNWF) (SEQ ID NO:7) with a variable number of a flexible link (GGGGS) (SEQ ID NO:5).

All the polynucleotides expressing the antibody derivatives of the invention were synthetized using the GeneArt process and the pcDNA3.1 and pcDNA3.4 expression plasmids.

Plasmids were reconstituted with 10 mM Tris buffer pH8 at 0.5 μg/μL. One Shot TOP10 chemically competent *E. coli* (Life Technologies Corp., Carlsbad, Calif., USA) were transformed using 1 μL of plasmid and following the manufactured instruction. In brief, 1 μL of plasmid was added to a vial of bacteria and incubated on ice for 15 minutes. After that, the tube was incubated at 42° C. for 30 seconds and immediately left on ice for two minutes. Bacteria were resupended in 250 μL of SOC medium (Life Technologies Corp., Carlsbad, Calif., US) and incubated for 1 hour at 37° C. and 225 rpm in an Innova 4000 incubator shaker (New Brunswick Scientific Co., Inc., Enfield, Conn., USA). After that, 100 μL of a 1/100 dilution of the cell culture were spread onto ampicillin selection (100 μg/mL) LB-Agar plates. Plates were incubated at 37° C. from 16-24 hours into a Heraeus incubator (Thermo Fisher Scientific, Waltham, Mass., USA). One colony was isolated and inoculated into 5 mL of ampicillin (100 μg/mL) selection LB medium and incubated for 8 hours at 37° C. and 225 rpm in an Innova 4000 incubator shaker (New Brunswick Scientific Co., Inc., Enfield, Conn., USA). After that, 500 mL of ampicillin (100 μg/mL) selection LB medium was inoculated with 500 μL of the former described culture and incubated at 37° C. and 225 rpm for 16 hours as described previously. Bacteria were harvested by centrifugation at 3000×g for 45 minutes at room temperature in an Eppendorf centrifuge 5810R (Thermo Fisher Scientific, Waltham, Mass., USA) and plasmids were isolated using the Qiagen Plasmid Maxi Kit (Qiagen NV, Venlo, NL) and following the manufacturer's instructions. Purified plasmids were quantified by spectrophotometry using a nanodrop 1000 instrument (Thermo Fisher Scientific, Waltham, Mass., USA).

2. Protein Production, Quantification, and Purification

HEK-293 cells were transfected with the plasmids encoding for the different antibody derivatives of the invention using Calphos transfection kit (Clontech®, Takara Bio Inc., Otsu, JP) following the manufacturer's instructions. After 48 hours, the supernatant was collected, clarified by filtration through a 0.45 μm filter (EMD Millipore, Merck KGaA, Darmstadt, DE) and stored at −20° C. until use.

Antibody derivatives were quantified by ELISA. In brief, Maxisorp 96-F plates (Nunc, Thermo Fisher Scientific, Waltham, Mass., USA) were incubated overnight at 4° C. with 100 μL/well of a F(ab)2 goat anti-human IgG (Fc-specific) antibody (Jackson ImmunoResearch Labs, Inc., West Grove, Pa., USA) at 1 μg/mL in PBS. After blocking with PBS/10% FBS/0.05% tween20 and washing, serial dilutions of culture supernatant (containing the recombinant protein) in a blocking buffer were added to the plate (100 μL/well) and incubated overnight at 4° C. As standard, 0.1 μg/mL, 0.05 μg/mL and 0.025 μg/mL dilutions of the purified eCD4-Ig protein, were used. The plates were washed again and a secondary antibody HRP-F(ab)2 Goat anti-human IgG (Fc-specific) (Jackson ImmunoResearch Labs, Inc., West Grove, Pa., USA) at 1/10000 dilution in blocking buffer was added (100 μL/well) and incubated at room temperature for one hour. Plates were washed and the bound antibodies were detected using OPD substrate and the reaction stopped adding 4N $H_2SO_4$. The product was measured at 492 nm in an ELISA plate reader.

Proteins were purified using protein A sepharose (GE Healthcare, Inc., Stamford, Conn., USA) column. Proteins were produced by transient transfection using serum free medium, as indicated above. Supernatants were harvested, centrifuged at 3000×g for 10 minutes and filtered at 0.45 μm to remove cell debris. Clarified supernatant was added to previously washed protein A sepharose beads and incubated overnight at 4° C. with end to end rotation. Protein A was washed with Tris buffer saline (TBS) and the bound protein eluted with 4M $MgCl_2$. Alternatively, proteins were purified using CaptureSelect FcXL Affinity Matrix (Thermo Fisher Scientific, Waltham, Mass., USA) columns and eluted with glycine buffer pH=3.5. Purified proteins were dialyzed against PBS, concentrated by ultrafiltration, quantified by ELISA or spectrophotometry and stored at −80° C. until use.

3. Neutralization Assays

HIV-1 isolates NL4-3, BaL, AC10, SVBP6, SVBP8, SVBP11, SVBP12, SVBP14, SVBP15, SVBP17, SVBP18 and SVBP19 were generated as pseudoviruses using Env expression plasmids and the pSG3 vector. See Sanchez-Palomino S, et al., Vaccine 2011; 29:5250-5259. Cell-free virus neutralization by the antibody derivatives was tested by a standard TZM-bl based assay. See Li, 2005, supra. Briefly, in a 96-well culture plate, 100 of previously diluted antibody derivatives were preincubated with 50 μL of pseudovirus stock, using 200 $TCID_{50}$ (tissue culture infectious doses) at 37° C. for one hour. Then, 100 containing 10,000 TZM-bl luciferase-reporter target cells per well were added. Plates were cultured at 37° C. and 5% $CO_2$ for 48 hours. Serial dilutions of the antibody derivatives were tested, from 1000 to 0.1 ng/mL. TZM-bl reporter cells were treated with dextran (Sigma-Aldrich, Saint Louis, Mo., USA) to enhance infectivity. A luciferase substrate, Britelite Plus (PerkinElmer, Inc., Waltham, Mass., USA), was used for the readout. Non-linear fit of neutralization data was calculated using normalized values fitted to a one site inhibition curve with variable Hill slope. All statistical analyses and non-linear fitting were performed using the GraphPad Prism v5.0 software.

4. ADCC Assays

To evaluate the ability of the different antibody derivatives to activate NK mediated destruction of HIV infected cells by NK Cells, an ADCC assay was conducted according to Alpert M, et al., J. Virol. 2012, 86:12039-12052. Briefly, the NK cell line KHYG-1 CD16+ was employed as the source of effector cells and the CEM.NKR.CCR5+ Luc cell line was utilized as the source of target cells. Five days prior to the assay, the target cells were infected with a highly infectious BaL isolate stock and cultured in R10 medium (RPMI supplemented with 10% fetal calf serum) at 37° C. To set up the assay, $10^4$ target cells (>40% of them productively infected) were cultured with $10^5$ effector cells in R10 medium supplemented with 10 U/ml of recombinant IL-2 in the presence of different concentrations of the antibody derivatives or antibody-based molecules in a total volume of 200 μL in U bottom 96 well plates. After 8 hours of incubation at 37° C., cells were resuspended and 150 μL of cells suspension was mixed with 50 μL of luciferase substrate, Britelite Plus (PerkinElmer, Inc., Waltham, Mass., USA). Luciferase units were used for the readout. Since target cells express luciferase upon HIV infection, the reduction of luciferase activity is a direct measure of antibody- and NK mediated-cell killing.

Example 1

Design of Engineered CD4 IgG Fusion Proteins

Figure 1:
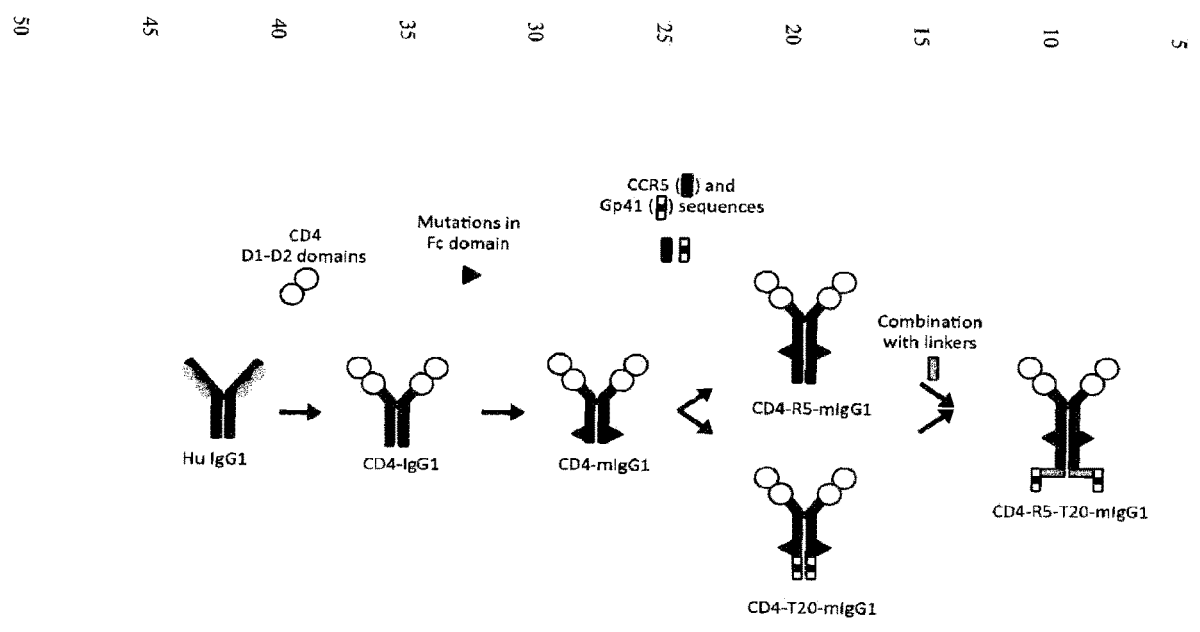

A huCD4-murine IgG fusion protein was prepared as previously reported. This fusion protein has been used in the past for the identification of anti-CD4 binding site antibodies. See Carrillo J, et al., PLOS One 2015; 10(3):0120648; FIG. 1. However, since CD4-IgG1 molecules are known to have limited therapeutic potential, several changes were introduced to the sequence of the CD4-IgG1 protein to increase its antiviral and ADCC activities. See Jacobson J, et al., Antimicrob Agents Chemother. 2004; 48(2):423-429.

First, the Fc region of human IgG1 was mutated in positions G236A, S239D, A330L and I332E, as described in the art, to increase ADCC mediated responses. See Bournazos, 2014, supra. Further modifications, aimed at increasing the interaction with HIV Env, included the addition of a 29 amino acid sequence corresponding to the N-terminal extracellular region of CCR5 (SEQ ID NO:6) or the addition of a T-20 (SEQ ID NO:7) sequence at the C-terminal end of the Fc chain. See Gardner, 2015, supra. It was reasoned that the addition of a peptide capable of binding to gp41 and blocking the prefusion events of HIV entry could have a synergistic effect on antiviral activity. Therefore, an antibody derivative containing both the CCR5 (SEQ ID NO:6) and T-20 (SEQ ID NO:7) sequences was designed. See FIGS. 1 and 2.

Figure 3:
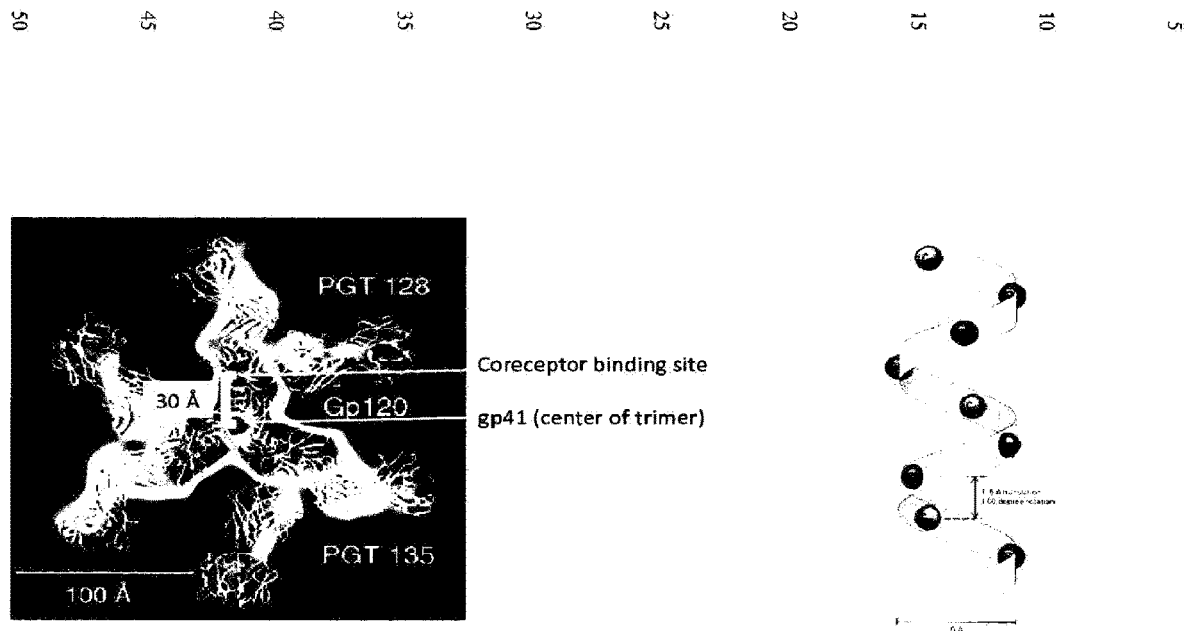
FIG. 3. Schematic representation of the rationale for determining the length of the linker polypeptide in MOLECULE-5. Assuming that (i) a distance of 30 Å between the coreceptor binding site of gp120 and the T-20 target region (gp41 in the center of the trimer), and (ii) the linker would adopt an alpha helix structure having a peptide bond distance of 1.5 Å, a linker of at least 20 residues was considered to be necessary for allowing the simultaneous interaction of the CCR5 and T-20 sequences with their respective targets. Taking into account the considerations above, a flexible linker (GGGGS)$_n$ (SEQ ID NO:5), where n=4, was included between the CCR5 and T-20 sequences.

It was further reasoned that synergy would occur if the CCR5 and T-20 sequences were able to interact simultaneously with their respective target regions. Therefore, a linker spanning from the coreceptor binding site to gp41 was proposed. See FIG. 3.

For comparison purposes, an eCD4-IgG1 fusion protein was also prepared as described previously (MOLECULE-1). At present, the eCD4-IgG1 fusion protein is the most potent anti-HIV engineered antibody known in the art. See Gardner, 2015, supra. In order to provide a better comparison basis, the Fc chain of MOLECULE-1 was further mutated as in the antibody derivatives of the invention (i.e. in positions G236A, S239D, A330L and I332E) to yield the eCD4-mIgG1 fusion protein (MOLECULE-2).

Example 2

Antiviral Activity of First Generation Antibody Derivatives

A standard neutralization assay was conducted to evaluate the antiviral activity of the antibody derivatives of the invention using three different viruses: (i) a HIV-1 strain NL4-3, a X4-monotropic laboratory isolate, (ii) a HIV-1 strain BaL, a R5-monotropic laboratory isolate and (iii) a HIV-1 strain AC10 isolate, a tier 2-type virus particularly difficult to neutralize. In addition, a deeper characterization of neutralizing activity was performed using a well-known panel of HIV subtype B viruses. See Li, 2005, supra.

Briefly, in a 96-well culture plate, 100 µL of previously diluted plasma samples were preincubated with 50 µL of pseudovirus stock, using 200 $TCID_{50}$ at 37° C. for one hour. Then, 100 µL containing 10,000 TZM-bl luciferase-reporter target cells per well were added. Plates were cultured at 37° C. and 5% $CO_2$ for 48 hours. Serial dilutions of the antibody derivatives were tested, from 1000 to 0.1 ng/mL. TZM-bl reporter cells were treated with dextran (Sigma-Aldrich, Saint Louis, Mo., USA) to enhance infectivity. A luciferase substrate, Britelite Plus (PerkinElmer, Inc., Waltham, Mass., USA), was used for the readout. Non-linear fit of neutralization data was calculated using normalized values fitted to a one site inhibition curve with variable Hill slope. All statistical analyses and non-linear fitting were performed using the GraphPad Prism v5.0 software.

Figure 4A:
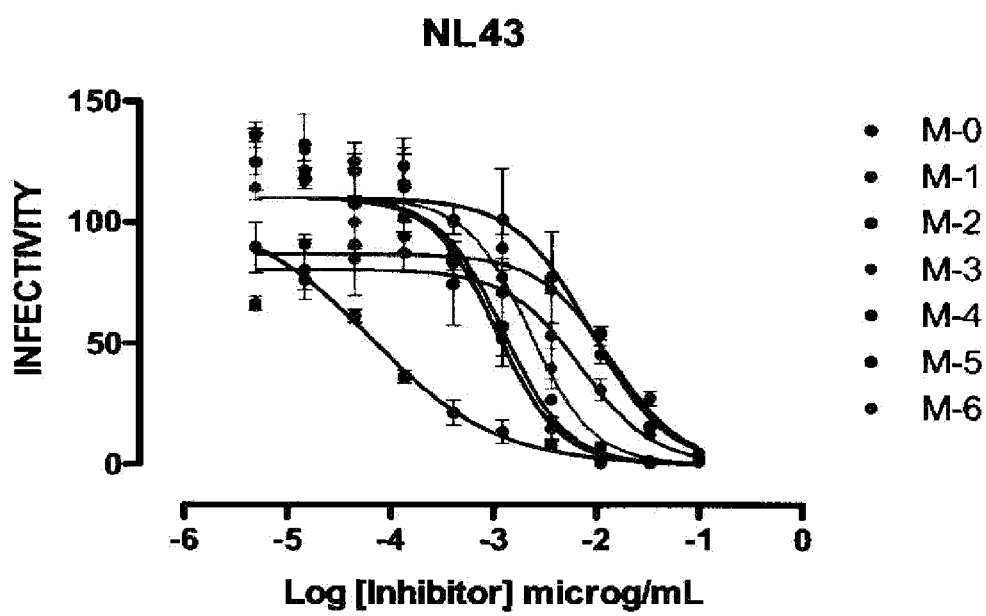
FIG. 4. Neutralization capacity of the first generation antibody derivatives MOLECULES-0-6, (a) neutralization of HIV NL4-3 isolate, (b) neutralization of HIV BaL isolate and (c) neutralization of HIV AC10 isolate.

All molecules tested were effective in blocking the infectivity of the NL4-3 and BaL isolates. For NL4-3 neutralization, the CCR5-containing MOLECULE-4 showed an $IC_{50}$ values of 7.1 ng/mL, while the T-20-containing MOLECULE-3 was more potent, showing an $IC_{50}$ value of 2.2 ng/mL. A lower value was observed for the reference molecule eCD4-IgG (MOLECULE-1, $IC_{50}$ value: 1.2 ng/mL) and its Fc mutated derivative MOLECULE-2 ($IC_{50}$=1.1 ng/mL). The most potent compound was the antibody derivative containing the CCR5 and T-20 sequences (MOLECULE-5), which showed and $IC_{50}$ value of 0.06 ng/mL. This data suggested that the combination of the CCR5 and T-20 sequences with a flexible linker conferred an improved antiviral potency. See FIG. 4(a); Table 1. A lower neutralizing activity was observed for MOLECULE-0 and MOLECULE-6, which contained only CD4 sequences.

Figure 4B:
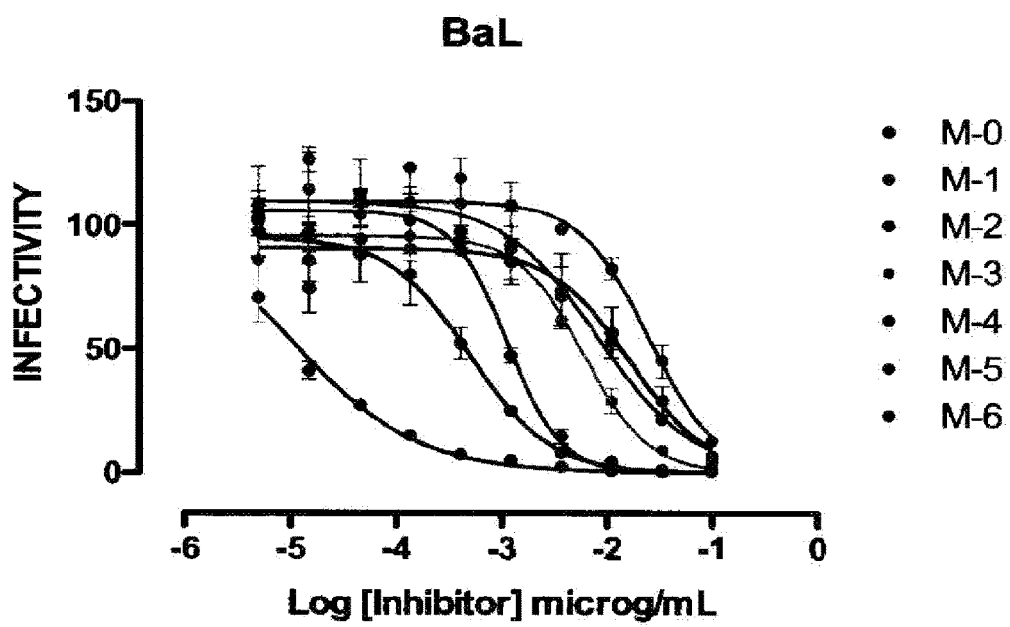

Similar results were observed with the BaL isolate. The rank of antiviral activity in the BaL neutralization assay was MOLECULE-4<MOLECULE-3<MOLECULE-1 (eCD4-IgG)<MOLECULE-2 (eCD4-mIgG1)<MOLECULE-5. Again, MOLECULE-5 showed the highest potency with an $IC_{50}$ value of 0.01 ng/mL, a 100-fold more potent than the eCD4-IgG1 protein. See FIG. 4(b); Table 1. Again, lower neutralizing activity was observed for MOLECULE-0 and MOLECULE-6, which contained only CD4 sequences.

Figure 4C:
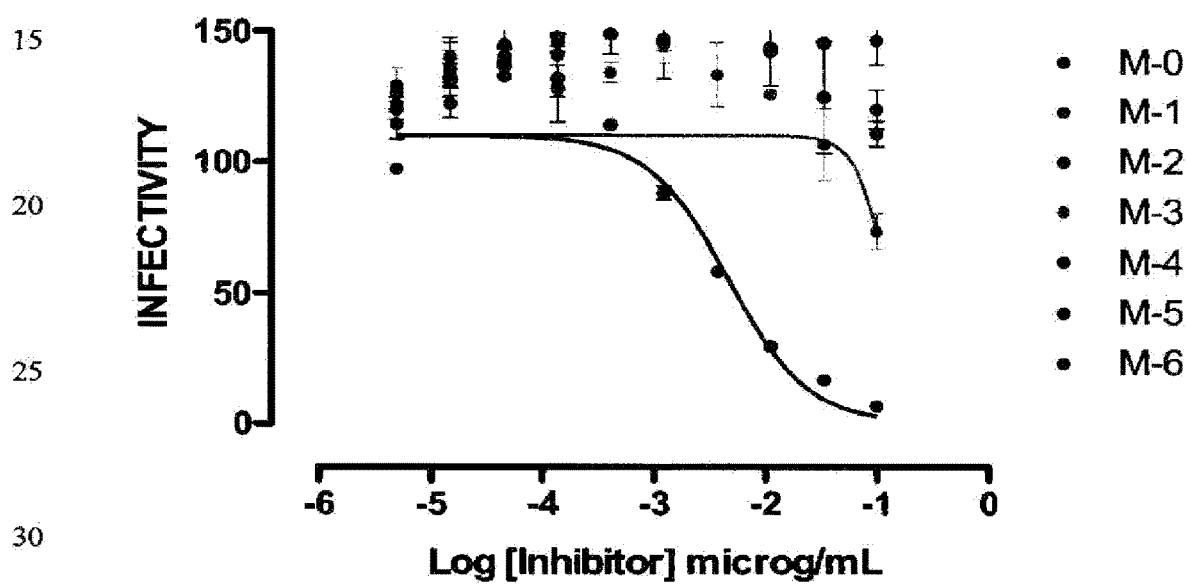
Figure 5:
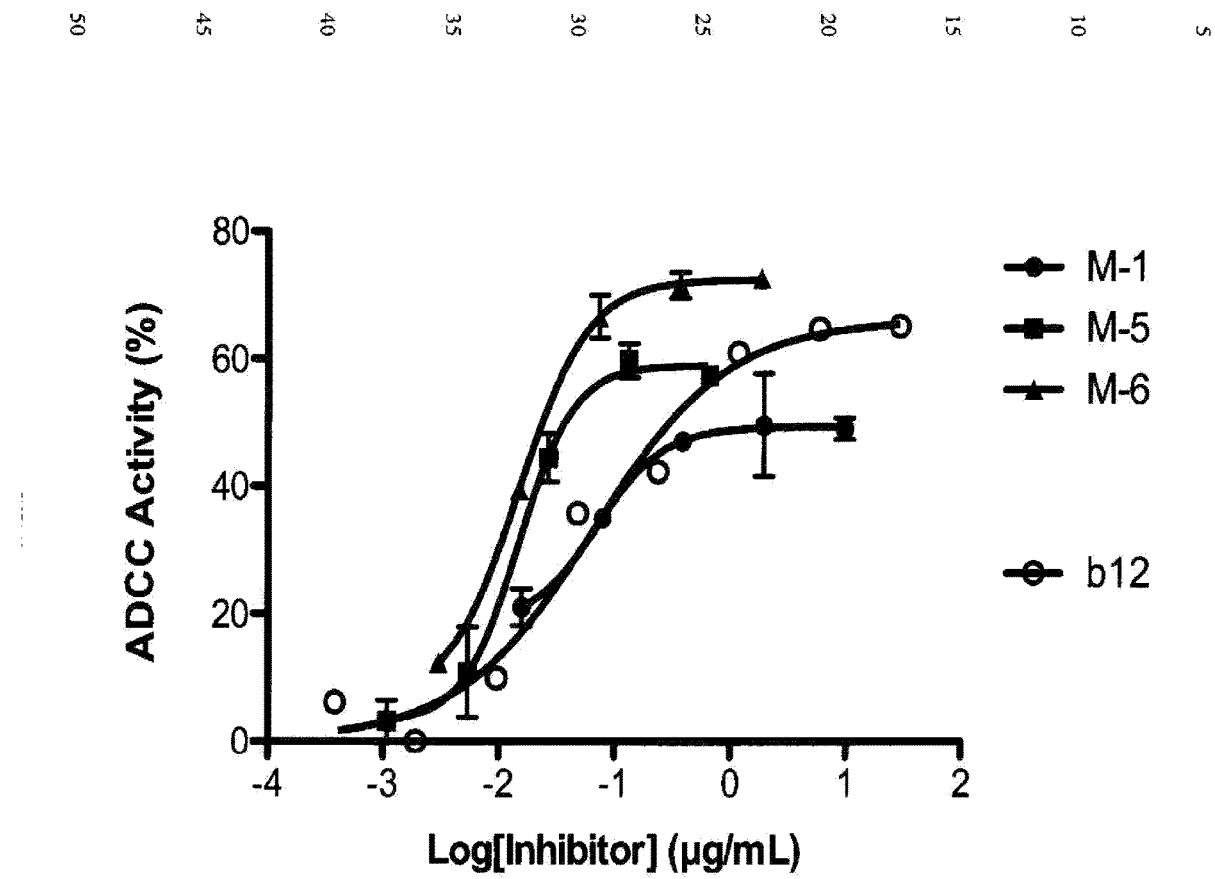
FIG. 5. ADCC activity of selected first generation antibody derivatives MOLECULE-1, MOLECULE-5 and MOLECULE-6. The antibody IgGb12 was included in the assay as a control.
Figure 6:
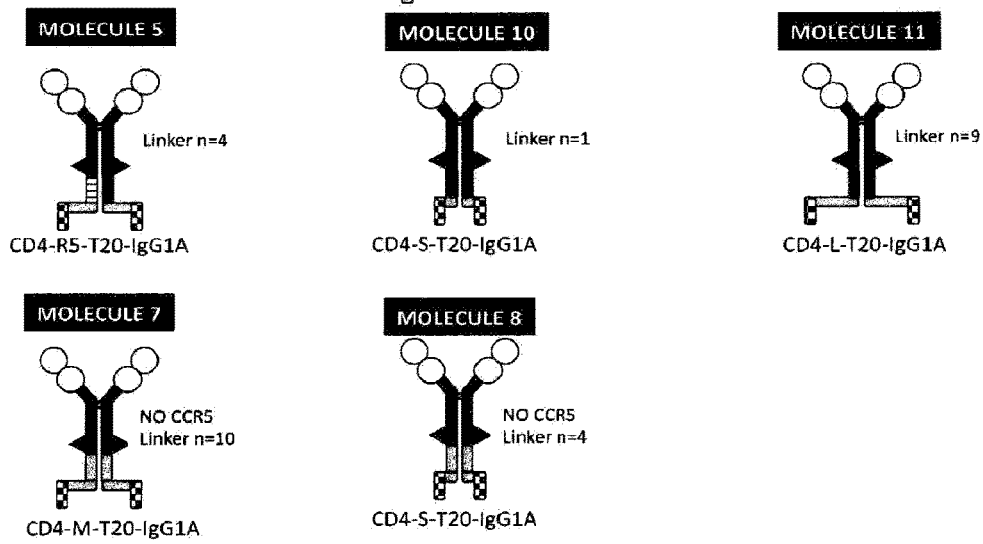
FIG. 6. Schematic representation of the second generation antibody derivatives MOLECULES-7-11. CCR5=SEQ ID NO: 6; T20=SEQ ID NO: 7, GGGGS=SEQ ID NO: 5.
Figure 7A:
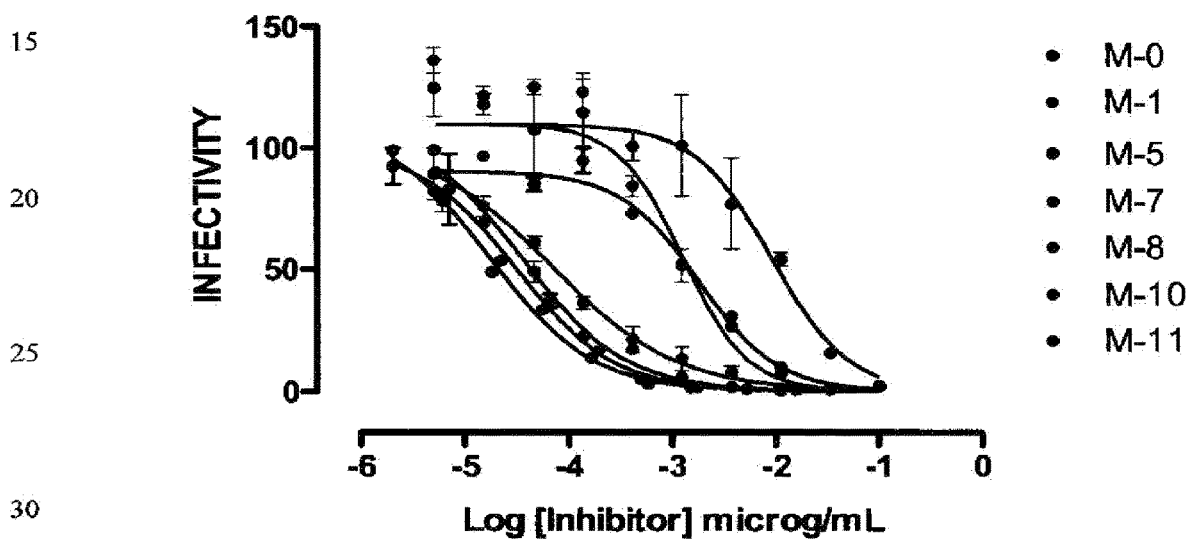
FIG. 7. Neutralization capacity of the second generation antibody derivatives MOLECULES-7-8 and MOLECULES-10-11 against a panel of NL4-3, BaL and AC10 HIV isolates. MOLECULE-0, MOLECULE-1 and MOLECULE-5 were included in the analysis as references, (a) neutralization of HIV NL4-3 isolate, (b) neutralization of HIV BaL isolate and (c) neutralization of HIV AC10 isolate.
Figure 7B:
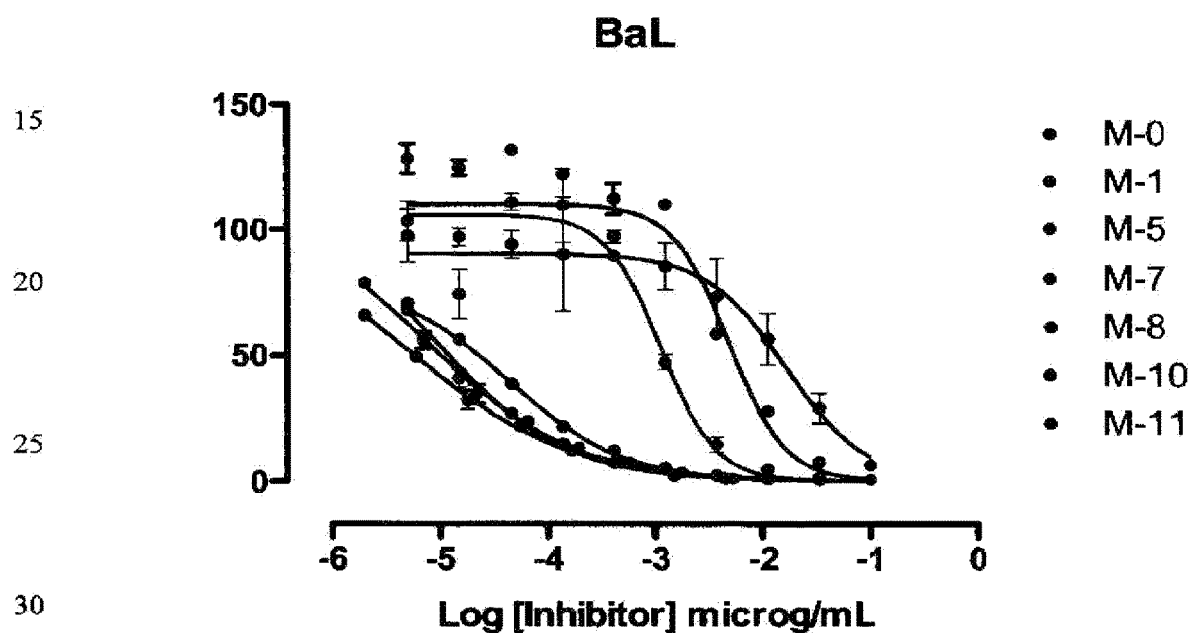
Figure 7C:
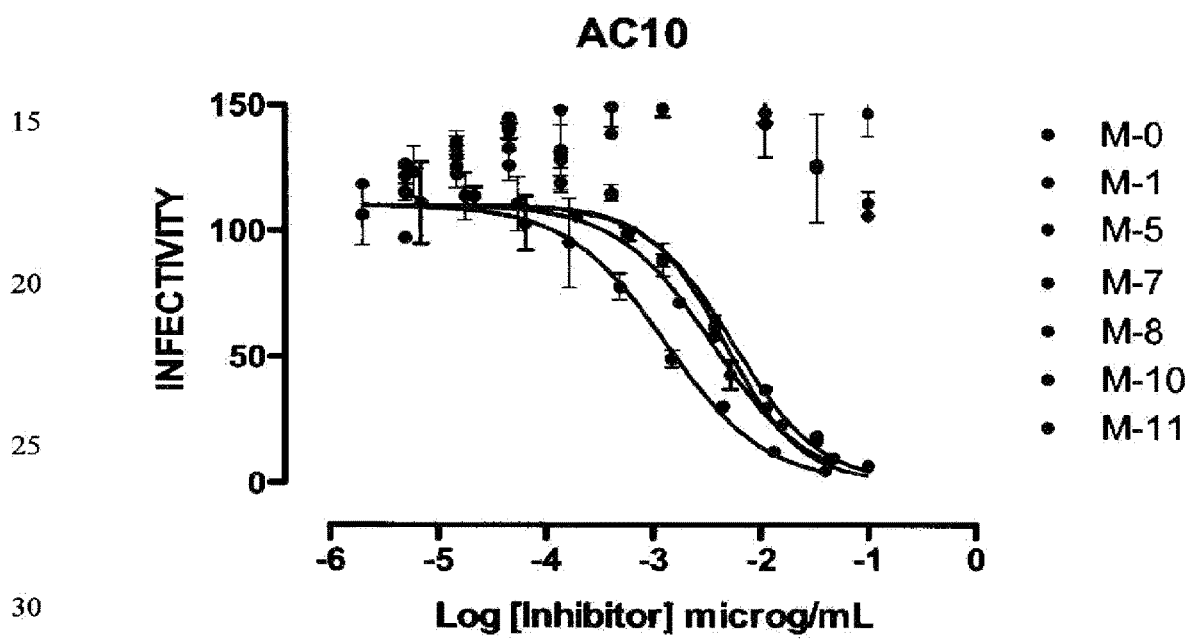
Figure 8:
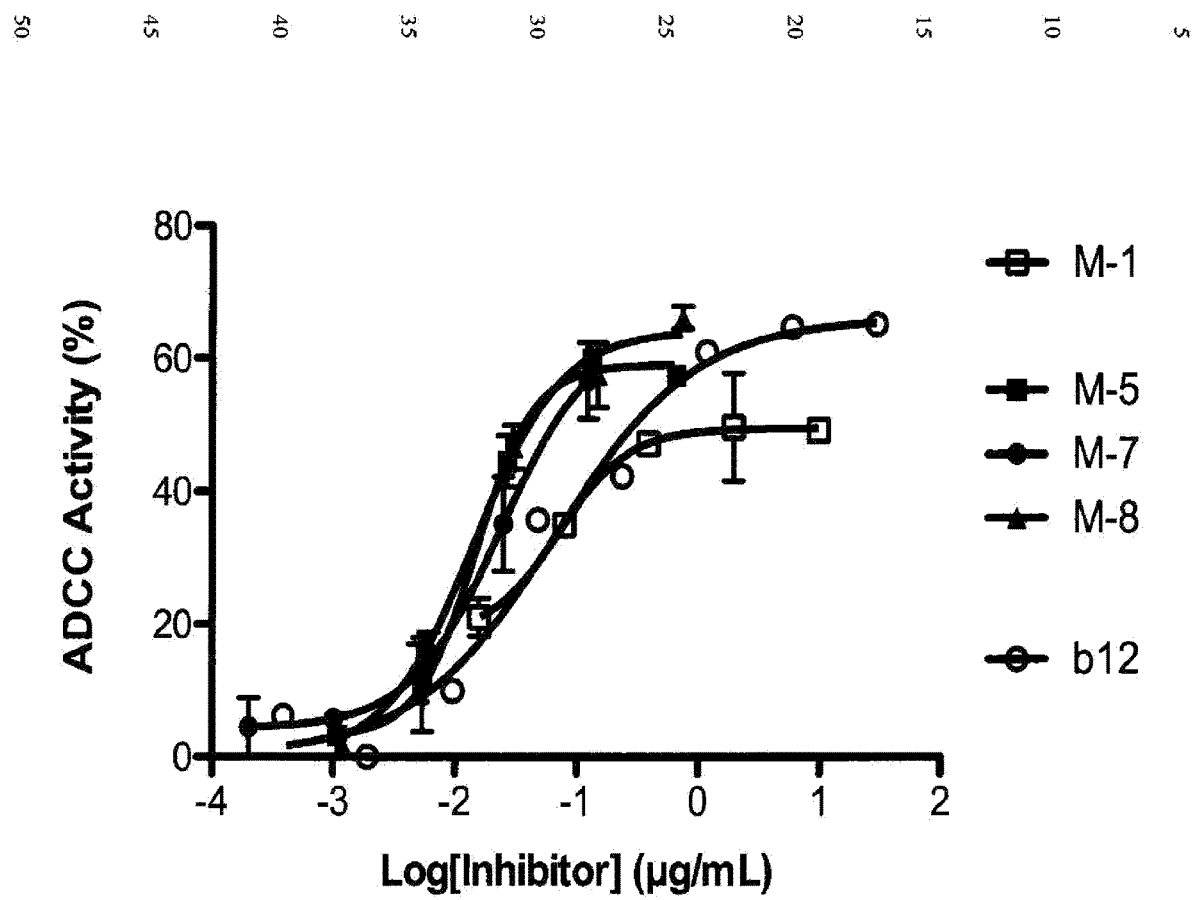
FIG. 8. ADCC activity of selected second generation antibody derivatives MOLECULE-5, MOLECULE-7 and MOLECULE-8. The antibody IgGb12 and MOLECULE-1 were included in the analysis as controls.

Surprisingly, only MOLECULE-5 showed any antiviral activity against the AC10 isolate; the rest of the antibody derivatives were ineffective in the range of concentrations tested. See FIG. 4(c); Table 1.

TABLE 1

| Antibody derivative | $IC_{50}$ (ng/mL) | | | Description |
|---|---|---|---|---|
| | NL4-3 | BAL | AC10 | |
| MOLECULE-0 | 8.9 | 16.4 | >100 | CD4-IgG1 |
| MOLECULE-1 | 1.2 | 1.1 | >100 | eCD4-IgG1 (Gardner, 2015, supra) |
| MOLECULE-2 | 1.1 | 0.5 | >100 | eCD4-mIgG1 |
| MOLECULE-3 | 2.2 | 6.1 | >100 | CD4-mIgG1-T20 |
| MOLECULE-4 | 7.1 | 8.2 | >100 | CD4-mIgG1-CCR5 |
| MOLECULE-5 | 0.06 | 0.009 | 4.7 | CD4-mIgG1-CCR5-5L-T20 |
| MOLECULE-6 | 14.0 | 24.6 | >100 | CD4-mIgG1 |
| Ratio MOLECULE-5/MOLECULE-1 | ×20 | ×100 | >100 | |

Example 3

Antibody-Dependent Cellular Cytotoxicity (ADCC) Activity of First Generation Antibody Derivatives An additional feature of the antibody derivatives of the invention is their ability to activate NK cells and mediate ADCC. This mechanism is important for the efficient and quick removal of HIV infected cells and contributes to the protection of uninfected subject to HIV exposure and acquisition. See Euler Z, et al., AIDS Res Hum Retroviruses 2015; 31(1):13-24.

Figure 10:
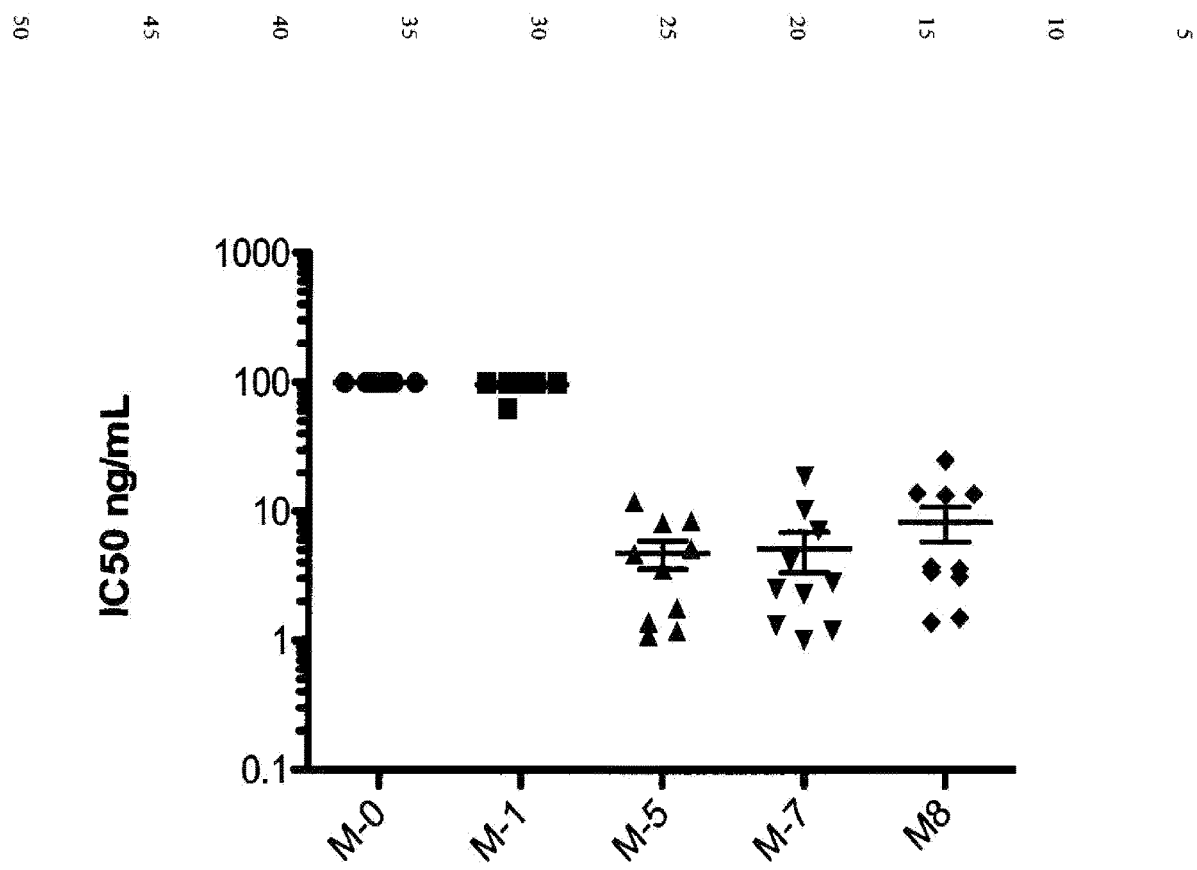
FIG. 10. Summary of $IC_{50}$ values of selected molecules against a panel of HIV isolates.

The ADCC activity of the antibody derivatives of the invention was evaluated using a test previously reported in the art. See Alpert M, et al., J. Virol. 2012, 86:12039-12052. In this assay, the killing capacity of NK cells is measured by the reduction of luciferase expression in a reporter cell line infected with HIV. The ability of the antibody derivative containing the CCR5 and T-20 sequences (MOLECULE-5) to induce ADCC was compared to a CD4-IgG1 fusion protein (i.e. MOLECULE-6, containing a mutated Fc fragment) and the eCD4-IgG1 fusion protein (MOLECULE-1). The analysis of dose response curves against cells infected with the HIV BaL isolate showed that $IC_{50}$ values for MOLECULE-1 and IgGb12 were 71.4 and 66.2 ng/mL, respectively, while molecules containing mutated Fc residues showed lower $IC_{50}$ values. MOLECULE-6 and MOLECULE-5 destroyed HIV infected cells with an $IC_{50}$ value of 15.0 and 14.9 ng/mL, respectively. See FIG. 5. These data suggest that the addition of mutations in the Fc region of antibodies may significantly enhance their protective capacity.

Example 4

Optimization of the Length of the Linker and Analysis of the Role of the CCR5 Sequence Although MOLECULE-5 showed considerably higher antiviral (+10,000%) and ADCC (500%) activities than the reference eCD4-IgG1 fusion protein (MOLECULE-1), further modifications to the original design of the antibody derivatives of the invention were proposed in order to enhance their activities. The purposes of these modifications were: (i) to optimize the length of the linker and (ii) to evaluate if the inclusion of the CCR5 sequence contributed significantly to the antiviral and ADCC activities of the antibody derivatives. A new collection of antibody derivatives was prepared according to the protocols above. These antibody derivatives displayed different linker lengths and included or not the CCR5 sequence. See FIG. 6.

Example 5

Antiviral Activity of Second Generation Antibody Derivatives

A standard neutralization assay was conducted to evaluate the antiviral activity of the modified antibody derivatives as described in Example 2.

All molecules tested were effective in blocking the infectivity of the NL4-3 and BaL isolates. For NL4-3 neutralization, the MOLECULE-5, MOLECULE-7 and MOLECULE-8 showed the highest potency with similar $IC_{50}$ values of 0.06, 0.017 and 0.031 ng/mL, respectively. MOLECULE-10 showed the lowest potency with an $IC_{50}$ of 1.8 ng/mL, while MOLECULE-11 showed intermediate activity with an $IC_{50}$ of 0.35 ng/mL. The $IC_{50}$ values for reference compounds MOLECULE-1 (eCD4-IgG1) and MOLECULE-0 (CD4-IgG1) were 1.2 and 8.9 ng/mL, respectively. Noteworthy, MOLECULE-5, MOLECULE-7 and MOLECULE-8 were more potent than MOLECULE-1. For instance, MOLECULE-7 was 1000% more potent than MOLECULE-1 for NL4-3 virus. See FIG. 7(*a*); Table 2.

Similar results were observed for the BaL isolate. The rank of antiviral activity was MOLECULE-7<MOLECULE-8<MOLECULE-5<MOLECULE-11<MOLECULE-1 (eCD4-IgG1)<MOLECULE-10. Again, the MOLECULE-7 showed the highest potency with an $IC_{50}$ value of 0.005 ng/mL, 20,000% more potent than the MOLECULE-1 (eCD4-IgG1) reference protein. See FIG. 7(*b*); Table 2.

Importantly, only the modified antibody derivatives according to the invention (i.e. MOLECULE-7, MOLECULE-5, MOLECULE-11 and MOLECULE-8) showed antiviral activity against the AC10 isolate. MOLECULE-7 exhibited the highest antiviral activity with an $IC_{50}$ value of 1.3 ng/mL, while MOLECULE-8 and MOLECULE-5 exhibited two/three-fold lower potency; a potency that was still much higher than MOLECULE-1 (eCD4-IgG1, which showed an $IC_{50>100}$ ng/mL). See FIG. 7(*c*); Table 2.

The data above suggests, surprisingly, that the CCR5 sequence might not be necessary for antiviral activity since both MOLECULE-5 and MOLECULE-7 show similar antiviral activity. The CCR5 sequence might be acting as a spacer sequence rather than offering a benefit in antiviral activity. This could be consistent with the lower affinity of interaction of the CCR5 N-terminal region with gp120 as compared to the affinity of CD4 for gp120 or the T-20 polypeptide for gp41. In addition, these results indicate also that either (a) the linker length by itself or (b) in combination with the mutations introduced to the Fc region has an effect over the antiviral activity of the antibody derivatives of the invention. This property would be suggested by a comparison of the $IC_{50}$ values of MOLECULE-5 and MOLECULE-8 with MOLECULE-1 for all three isolates, which shows that a mutated protein with a linker but without a CCR5 sequence (MOLECULE-8) has a comparable potency to a mutated protein with a linker and a CCR5 sequence (MOLECULE-5) and a much higher potency than a non-mutated protein without a linker (MOLECULE-1). See FIG. 7(*a*)-(*c*); Table 2.

TABLE 2

| Antibody derivative | $IC_{50}$ (ng/mL) NL4-3 | BAL | AC10 | Description |
|---|---|---|---|---|
| MOLECULE-0 | 8.9 | 16.4 | >100 | CD4-IgG1 |
| MOLECULE-1 | 1.2 | 1.1 | >100 | eCD4-IgG1 (Gardner, 2015, supra) |
| MOLECULE-5 | 0.06 | 0.009 | 4.7 | CD4-mIgG1-CCR5-5L-T20 |
| MOLECULE-7 | 0.017 | 0.005 | 1.3 | CD4-mIgG1-10L-T20 |
| MOLECULE-8 | 0.031 | 0.007 | 3.6 | CD4-mIgG1-4L-T20 |
| MOLECULE-10 | 1.8 | 4.8 | >100 | CD4-mIgG1-CCR5-1L-T20 |
| MOLECULE-11 | 0.035 | 0.043 | 5.6 | CD4-mIgG1-CCR5-9L-T20 |
| Ratio MOLECULE-7/MOLECULE-1 | ×70 | ×200 | >60 | |

Example 6

Antibody-Dependent Cellular Cytotoxicity (ADCC) Activity of Second Generation Antibody Derivatives The ADCC activity of the modified antibody derivatives was evaluated according to the protocol described in Example 3.

The ability of MOLECULE-5, MOLECULE-7 and MOLECULE-8 to induce ADCC activity was compared to eCD4-IgG1 (MOLECULE-1) and the neutralizing antibody IgGb12. The analysis of dose response curves against cells infected with the HIV BaL isolate showed that MOLECULE-5, MOLECULE-7 and MOLECULE-8 had a similar potency, with $IC_{50}$ values of 14.9, 23.8 and 14.3 ng/mL, respectively. On the other hand, reference molecules MOLECULE-1 and IgGb12 showed $IC_{50}$ values of 71.4 and 66.2 ng/mL, respectively, which demonstrated that they are less potent than MOLECULE-5, MOLECULE-7 and MOLECULE-8. See FIG. 8.

Again, these results suggest that the mutations introduced to the Fc region of the antibody derivatives enhance ADCC activity. MOLECULE-5 and MOLECULE-8 are 500% more potent than MOLECULE-1, while MOLECULE-7 is 300% more potent than MOLECULE-1.

To further characterize the increased antiviral or neutralizing ADCC activity of the antibody derivatives, MOLECULE-5, MOLECULE-7 and MOLECULE-8 were analyzed against a well-known panel of HIV subtype B viruses. See Li, 2005, supra. MOLECULE 0 and MOLECULE-1 were used again for comparative purposes. In summary, MOLECULE-0 showed low antiviral activity and was unable to neutralize primary isolates at 100 ng/mL. MOLECULE-1 showed slightly higher activity, but only one virus of the panel was neutralized below 100 ng/mL. See FIG. 9. In contrast, MOLECULE-5, MOLECULE-7 and MOLECULE-8 were able to block all primary isolates with $IC_{50}$ values ranging from 1 to 25 ng/mL. See FIG. 10.

Example 7

Antiviral Activity of Antibody Derivatives in Combination with Antiretroviral Drugs A standard neutralization assay was conducted to evaluate the antiviral activity of MOLECULE-5 against the HIV isolate NL4-3 in the presence of different concentrations of the following antiretroviral drugs: 3TC/lamivudine, efavirenz (EFV) and raltegravir (RAL), as described in Example 2. $IC_{50}$ values for MOLECULE-5 were determined (concentration range: 0.02 to 0.00001 µg/mL) in the presence of the following concentrations of antiretroviral drugs:

3TC—40, 8, 1.6, 0.32, 0.064, 0.013, 0.0026 and 0.0005 µM;

EFV—0.1, 0.02, 0.004, 0.0008, 0.0002, 0.00003, 0.000006 and 0.000001 µM; and

RAL—0.05, 0.01, 0.002, 0.0004, 0.00008, 0.00002, 0.000003 and 0.0000006 µM.

Figure 11A:
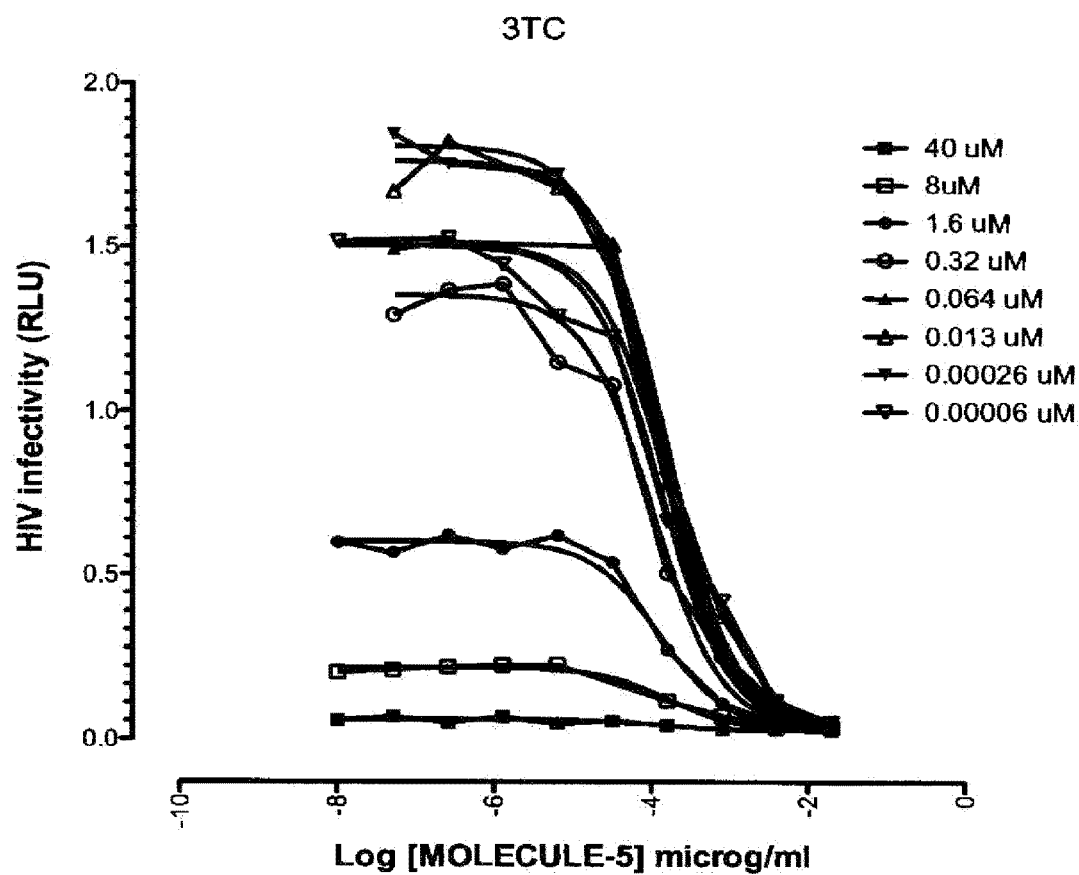
FIG. 11. Antiviral potency of MOLECULE-5 in the presence of the indicated concentrations of antiretroviral drugs, (a) 3TC, (b) efavirenz and (c) raltegravir.
Figure 11B:
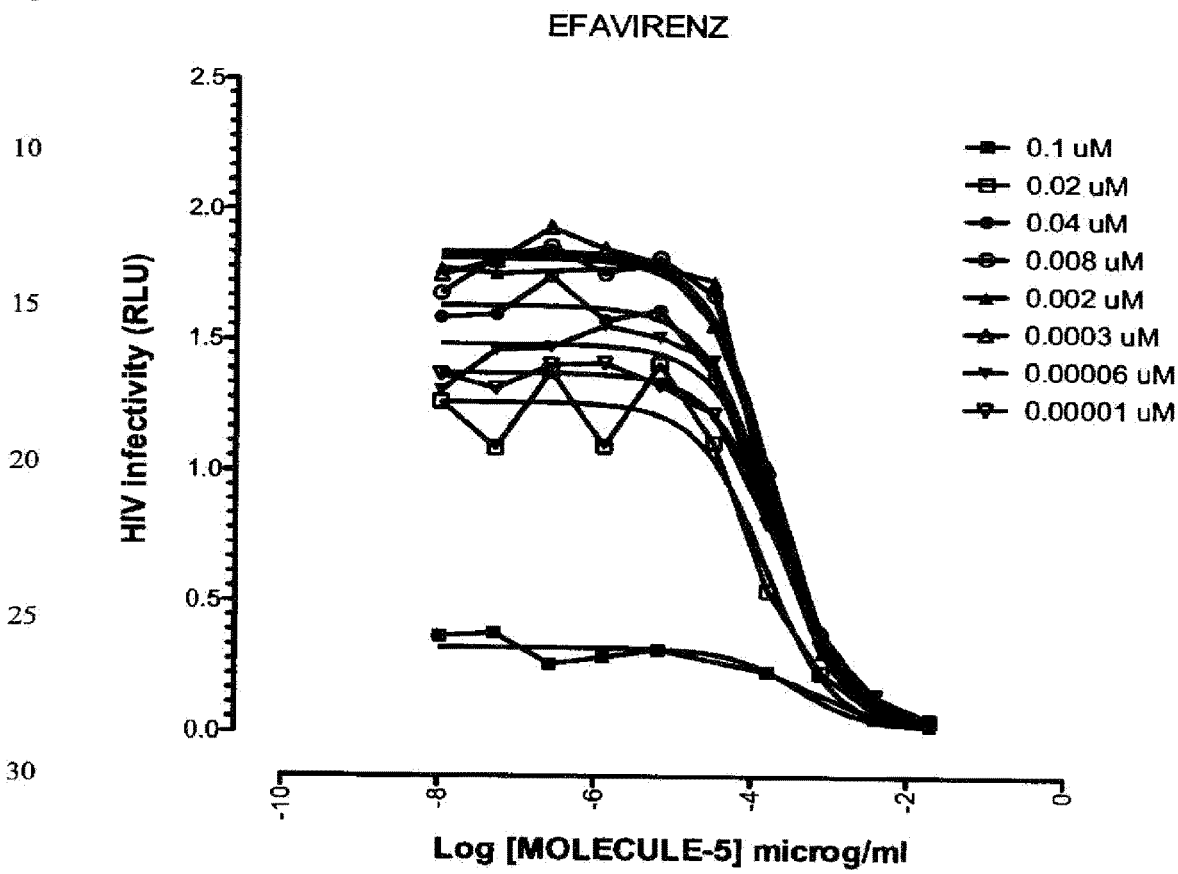
Figure 11C:
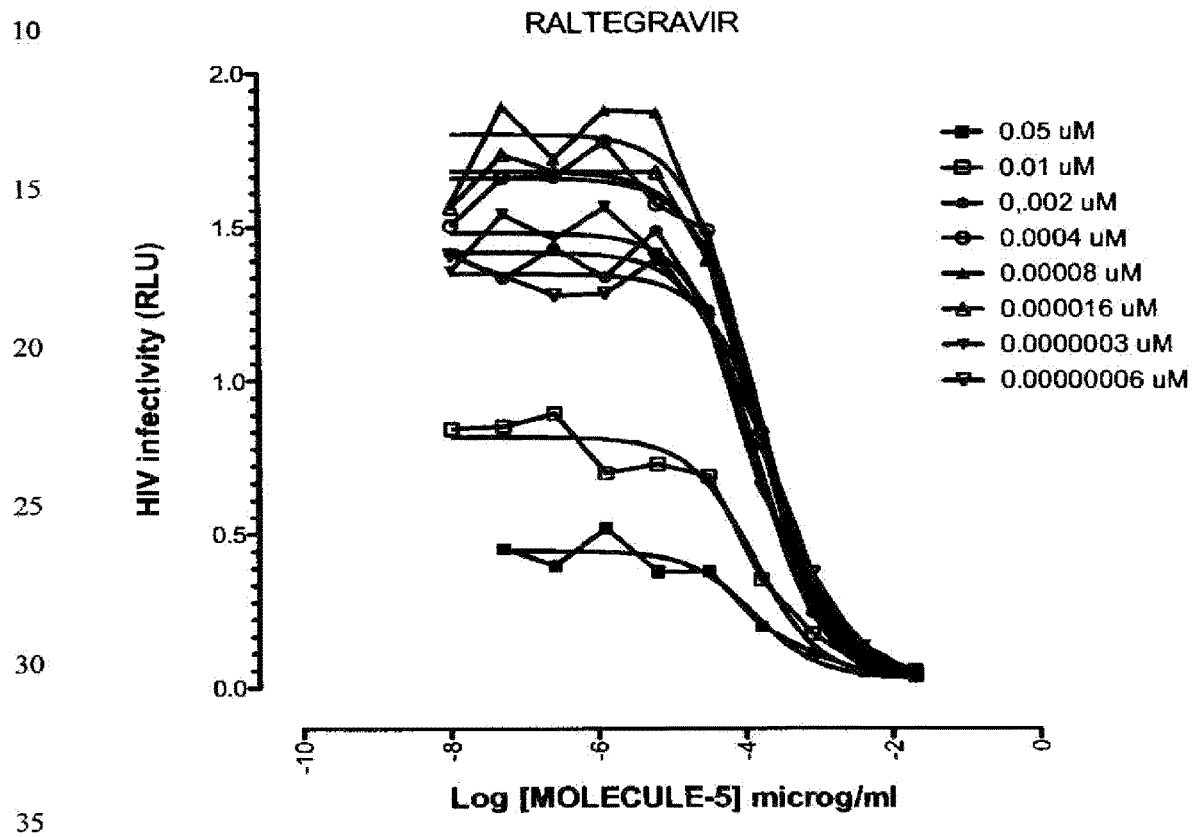

MOLECULE-5 was effective blocking HIV infectivity in all cases with $IC_{50}$ in the high pg/mL range (104 pg/mL was the lowest value detected while 257 pg/mL was the highest). See FIG. 11(a)-(c).

Example 8

Viral Inactivation Activity of Antibody Derivatives

To evaluate the irreversible inactivation of HIV induced by antibody derivatives, a highly infectious HIV BaL viral stock was incubated in DMEM culture medium with serial dilutions (concentration range: 0.7 µg/mL to 0.7 pg/mL) of MOLECULE-5 or the C34 derivative of MOLECULE-7 (concentration range: 1 µg/mL to 1 pg/mL). After 1 hour of incubation at 37° C., samples were diluted with DMEM and viruses and soluble proteins were separated by the addition of LentiX Concentrator reagent (Takara/Clontech Laboratories, Inc., Mountain View, Calif., USA). The mixture was incubated for 30 min at 4° C. and was subsequently centrifuged at 1,500×g for 45 minutes at 4° C. Supernatants were removed and viral pellets were re-suspended in DMEM. The infectivity of the treated viruses was analyzed by titration in TZM-bl cells. See Li M, et al., J. Virol. 2005; 79:10108-10125. The $TCID_{50}$ value was calculated for each preparation to assess the remaining infectivity of treated viruses.

Figure 12:
FIG. 12. Irreversible inactivation of HIV infectivity (BaL isolate) by MOLECULE-5 and by the C34 derivative of MOLECULE-7.

Both tested molecules were effective in irreversibly inactivating the infectivity of the BaL viral stock with $IC_{50}$ values of 0.055 and 0.044 µg/mL for MOLECULE-5 and for the C34 derivative of the MOLECULE-7, respectively. Remarkably, no viral infectivity was detected at concentrations higher than 0.1 µg/mL of both proteins; therefore, a reduction of more than five logs in viral infectivity titer was achieved. See FIG. 12.

Example 9

Antiviral Activity of Antibody Derivatives Displaying Different Gp41 Peptides

Silent mutations were introduced in the full sequence of MOLECULE-5 and MOLECULE-7 to allow for excision of the T20 sequence (SEQ ID NO:28). This sequence was replaced by the following sequences: T1249 (SEQ ID NO:29), C34 (SEQ ID NO:30) and T2635 (SEQ ID NO:31).

Figure 13:
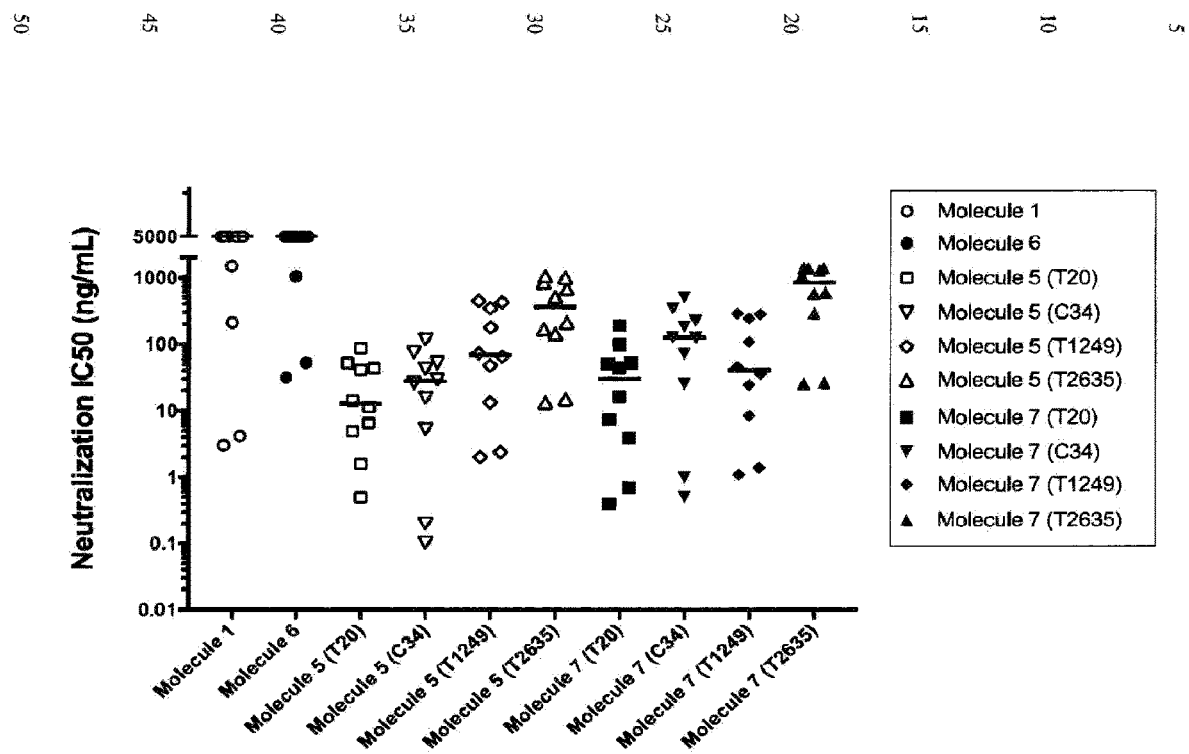
FIG. 13. Summary of $IC_{50}$ values of MOLECULE-5 and MOLECULE-7 derivatives displaying different gp41 polypeptides in the C-term of the protein against a SEQ ID NO:5 is the amino acid sequence of the linker polypeptide.
SEQ ID NO:6 is the amino acid sequence of the N-terminal region of the human CCR5 receptor.
SEQ ID NO:7 is the amino acid sequence of the T-20 polypeptide.
SEQ ID NO:8 is the amino acid sequence of the T-1249 polypeptide.
SEQ ID NO:9 is the amino acid sequence of the C34 polypeptide.
SEQ ID NO:10 is the amino acid sequence of the T-2635 polypeptide.
SEQ ID NO:11 is the amino acid sequence of MOLECULE-O.
SEQ ID NO:12 is the amino acid sequence of MOLECULE-1.
SEQ ID NO:13 is the amino acid sequence of MOLECULE-2.
SEQ ID NO:14 is the amino acid sequence of MOLECULE-3.
SEQ ID NO:15 is the amino acid sequence of MOLECULE-4.
SEQ ID NO:16 is the amino acid sequence of MOLECULE-5.
SEQ ID NO:17 is the amino acid sequence of MOLECULE-6.
SEQ ID NO:18 is the amino acid sequence of MOLECULE-7.
SEQ ID NO:19 is the amino acid sequence of MOLECULE-8.
SEQ ID NO:20 is the amino acid sequence of MOLECULE-10.
SEQ ID NO:21 is the amino acid sequence of MOLECULE-11.
SEQ ID NO:22 is the nucleotide sequence of the D1 domain of the human CD4 receptor.
SEQ ID NO:23 is the nucleotide sequence of the D2 domain of the human CD4 receptor.
SEQ ID NO:24 is the nucleotide sequence of the Fc portion of the human IgG1.
SEQ ID NO:25 is the nucleotide sequence of the Fc portion of the human IgG1 with G236A, S239D, A330L and I332E point mutations.
SEQ ID NO:26 is the nucleotide sequence of the linker polypeptide.
SEQ ID NO:27 is the nucleotide sequence of the 5' terminal region of the human CCR5 receptor.
SEQ ID NO:28 is the nucleotide sequence of the T-20 polypeptide.
SEQ ID NO:29 is the nucleotide sequence of the T-1249 polypeptide.
SEQ ID NO:30 is the nucleotide sequence of the C34 polypeptide.
SEQ ID NO:31 is the nucleotide sequence of the T-2635 polypeptide.
SEQ ID NO:32 is the nucleotide sequence of MOLECULE-O.
SEQ ID NO:33 is the nucleotide sequence of MOLECULE-1.
SEQ ID NO:34 is the nucleotide sequence of MOLECULE-2.
SEQ ID NO:35 is the nucleotide sequence of MOLECULE-3.
SEQ ID NO:36 is the nucleotide sequence of MOLECULE-4.
SEQ ID NO:37 is the nucleotide sequence of MOLECULE-5.
SEQ ID NO:38 is the nucleotide sequence of MOLECULE-6.
SEQ ID NO:39 is the nucleotide sequence of MOLECULE-7.
SEQ ID NO:40 is the nucleotide sequence of MOLECULE-8.
SEQ ID NO:41 is the nucleotide sequence of MOLECULE-10.
SEQ ID NO:42 is the nucleotide sequence of MOLECULE-11.
SEQ ID NO:43 represents amino acids 443-457 of MOLECULE-1.

Molecules were produced by transient transfection of HEK-293T cells as described above and a standard neutralization assay was conducted to evaluate the antiviral activity of these new MOLECULE-5 and MOLECULE-7 derivatives against a panel of HIV SVBP subtype B isolates, including laboratory adapted and primary isolates. See FIG. 13.

All MOLECULE-5 and MOLECULE-7 derivatives MOLECULE-5-T-1249, MOLECULE-5-C34, MOLECULE-5-T-2635, MOLECULE-7-T-1249, MOLECULE-7-C34 and MOLECULE-7-T-2635 were effective blocking HIV infectivity in all cases with $IC_{50}$ in the pg/mL or ng/mL range, showing higher potency and coverage than control molecules MOLECULE-1 or MOLECULE-6. See FIG. 13.

Example 10

Antiviral Activity of Antibody Derivatives Displaying Different Human IgG Sequences KpnI and NheI restriction sites were introduced in the full sequence of the C34 derivatives of MOLECULE-5 and MOLECULE-7 to allow for the excision of the Fc portion of the human IgG with the G236A, S239D, A330L and I332E point mutations (SEQ ID:25). This sequence was replaced by a wild type human IgG1 (SEQ ID NO:24), human IgG2, human IgG3 and human IgG4 sequence.

Molecules were produced by transient transfection of HEK-293T cells as described above and a standard neutralization assay was conducted to evaluate the antiviral activity against NL4-3 and BaL viruses (for new MOLECULE-5 derivatives) and against a panel of HIV SVBP subtype B isolates, including laboratory adapted and primary hard to neutralize isolates for new MOLECULE-7 derivatives.

Figure 14:
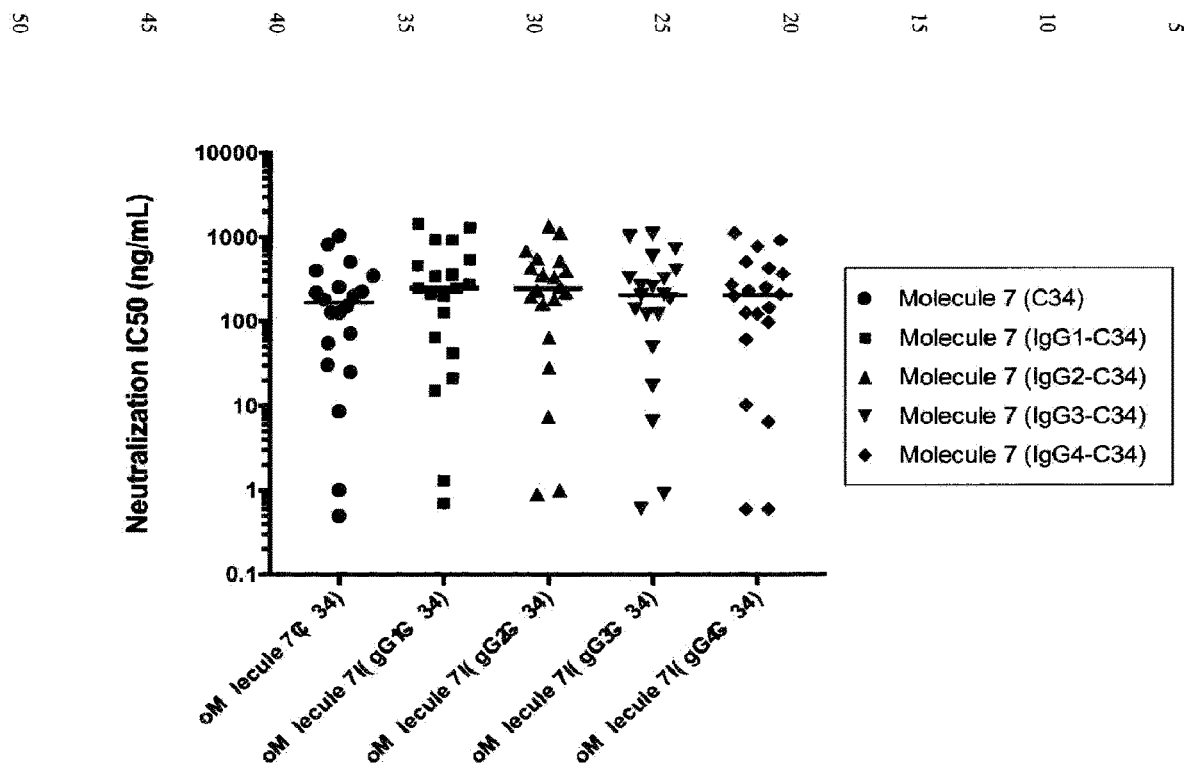

All MOLECULE-5 derivatives MOLECULE-5-IgG1, MOLECULE-5-IgG2, MOLECULE-5-IgG3 and MOLECULE-5-IgG4, were similarly effective blocking HIV infectivity in all cases with $IC_{50}$ in the pg/mL or ng/mL range, showing similar potency. See Table 3. All MOLECULE-7 derivatives MOLECULE-7-IgG1, MOLECULE-7-IgG2, MOLECULE-7-IgG3 and MOLECULE-7-IgG4, were similarly effective blocking HIV infectivity in all cases with $IC_{50}$ in the pg/mL or ng/mL range, showing similar potency and coverage. See FIG. 14.

TABLE 3

| Antibody derivative | $IC_{50}$ (ng/mL) | | Description |
| --- | --- | --- | --- |
| | NL4-3 | BAL | |
| MOLECULE-5 | 0.4 | 0.4 | CD4-mIgG1-CCR5-5L-T20 |
| MOLECULE-5 (C34) | 1.2 | 1.2 | CD4-mIgG1-CCR5-5L-C34 |
| MOLECULE-5 (IgG1-C34) | 0.9 | 1.3 | CD4-IgG1-CCR5-5L-C34 |
| MOLECULE-5 (IgG2-C34) | 0.8 | 1.1 | CD4-IgG2-CCR5-5L-C34 |
| MOLECULE-5 (IgG3-C34) | 0.8 | 0.8 | CD4-IgG3-CCR5-5L-C34 |
| MOLECULE-5 (IgG4-C34) | 0.8 | 0.8 | CD4-IgG4-CCR5-5L-C34 |

Example 11

AAV Mediated Expression of Antibody Derivatives In Vivo

NSG mice (Jackson Laboratory, Bar Harbor, Me., USA) were maintained by brother-sister mating under specific pathogen-free (SPF) conditions.

To induce stable expression of antibody derivatives in these animals, sequences coding for MOLECULE-5 (SEQ ID NO:37), MOLECULE-6 (SEQ ID NO:38), MOLECULE-7 (SEQ ID NO:39) and MOLECULE-8 (SEQ ID NO:40) were cloned into AAV8 expressing plasmids (CBATEG, Universitat Autonoma de Barcelona, Barcelona, ES). $1\times10^{11}$ viral particles were diluted into 40 μL of 100 mM sodium citrate, 10 mM Tris, pH 8 buffer and injected into the gastrocnemius muscle of eight weeks old mice. At the same time, mice were humanized by intraperitoneal injection of 10 million of PBMCs isolated from healthy individuals. After two weeks, mice were infected by intraperitoneal injection of 10000 $TCDI_{50}$ of NL4-3 HIV viral isolate. Blood samples were collected weekly and the CD4+ and CD8+ T cells count was analyzed by flow cytometry using Perfect Count beads (Cytognos SL, Salamanca ES) in combination with the following antibodies: anti-human CD45-V450, CD3-APC/Cy7, CD4-APC, CD8-V500, CD14-PerCP/Cy5.5, CD56-PE, CD16-Fitc and anti-mouse CD45 PE/Cy7. Samples were analyzed using a LSR II flow cytometer (BD Biosciences Corp., Franklin Lakes, N.J., USA). Samples were also assayed for antibody derivative levels using the above described ELISA approach. After 3 weeks from infection, mice were sacrificed and blood and tissue samples were collected. Samples were analyzed by flow cytometry and viral load and total HIV DNA were determined by qPCR.

Figure 15A:
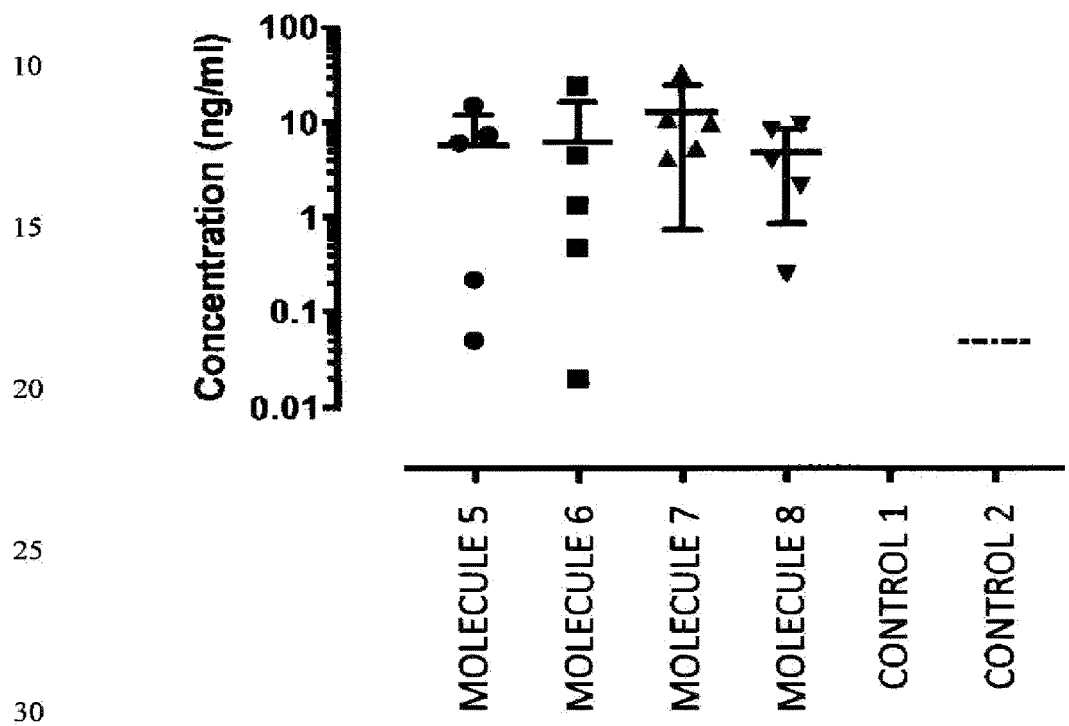
Figure 15B:
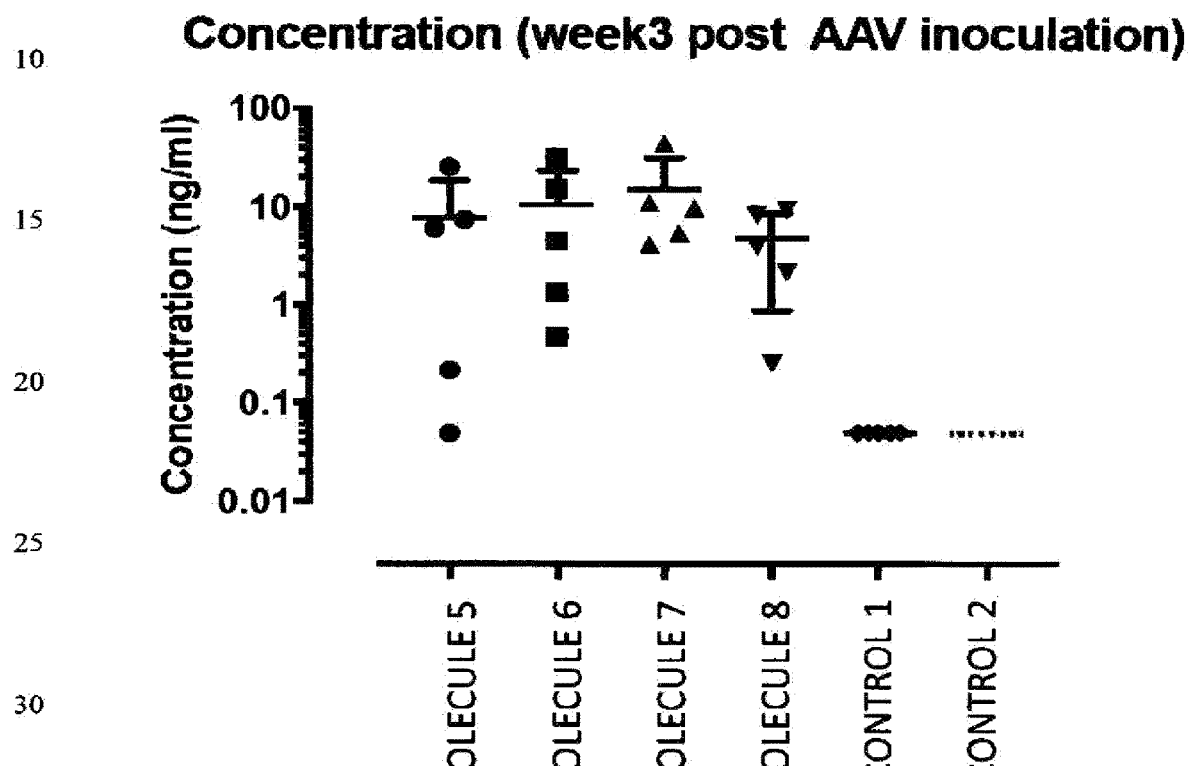

Detectable levels of antibody derivatives were found in most of treated animals 2 and 3 weeks after AAV treatment, as compared to untreated groups. Furthermore, the expression level was stable in all animals. See FIGS. 15(a) and 15(b).

Example 12

Passive Immunization Protocol with Plasmidic Vectors

NSG mice (Jackson Laboratory, Bar Harbor, Me., USA) were maintained by brother-sister mating under specific pathogen-free (SPF) conditions.

The plasmids pABT-5, pABT-7 and pABT-8 were produced in endotoxin free conditions using EndoFree Plasmid Kits (Qiagen NV, Venlo, NL). For transient expression of antibody derivatives in vivo, plasmids were administered to NGS mice by intramuscular or intravenous injections. After plasmid administration, blood samples were collected weekly and were assayed for antibody derivative levels using the above described ELISA approach. After 4 weeks from plasmid administration, mice were sacrificed and blood and tissue samples were collected and analyzed for antibody derivative levels and for anti-idiotype antibodies.

Example 13

In Vivo Activity of MOLECULE-5

Figure 16:
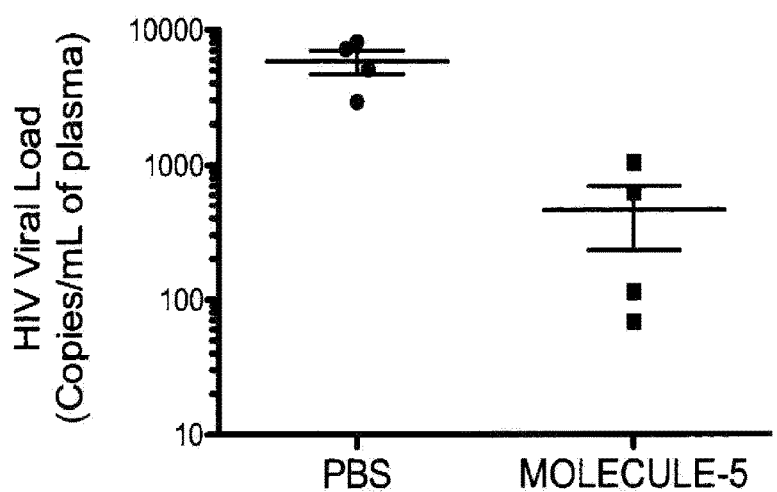

MOLECULE-5 was produced in large volume culture of HEK-293T cells by transient transfection. The recombinant protein was purified after loading supernatants in CaptureSelect FcXL Affinity Matrix (Thermo Fisher Scientific, Waltham, Mass., USA) columns and eluting bound protein with glycine buffer pH=3.5. After pH neutralization, dialysis and concentration, a highly pure stock of 5 mg/mL was obtained. NSG immunodeficient mice were humanized by intraperitoneal injection of 10 million of PBMCs isolated from healthy individuals. After two weeks, mice were infected by intravenous injection of 10,000 $TCID_{50}$ of NL4-3 HIV viral isolate. Mice were treated 24 hours before and 24 hours after infection with 0.5 mg of purified MOLECULE-5 in 200 or with the same volume of PBS by intraperitoneal injection. Blood samples were collected one week after infection by maxillary vein puncture and processed to obtain plasma samples, that were assayed for the levels of viremia using the Abbott Real Time HIV-1 (Abbott Laboratories, Abbott Park, Ill., USA). Animals treated with MOLECULE-5 showed significantly lower levels of viremia than untreated animals one week after infection. See FIG. 16.

Example 13

Detection of HIV Env Glycoproteins

To assess the ability of the antibody derivatives of the invention to identify HIV proteins in sample, MOLT cells chronically infected with the HIV isolates NL4-3 or BaL were incubated with increasing amounts of MOLECULE-5. Antibodies bound to these cells were revealed with a mouse anti human IgG antibody coupled with the fluorochrome Phycoerythrin (PE/Jackson ImmunoResearch Laboratories, Inc., West Grove, Pa., USA) and analyzed by flow cytometry in a LSRII flow cytometer (BD Biosciences Corp., Franklin Lakes, N.J., USA).

Figure 17:
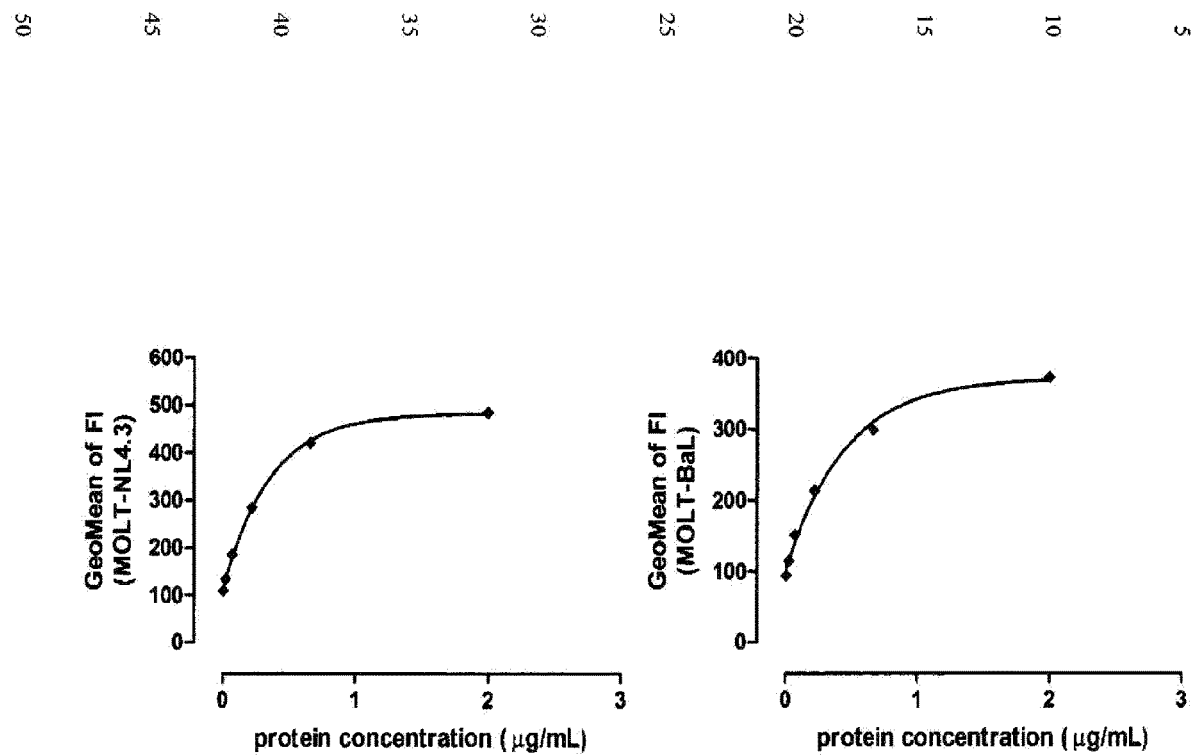
Figure 18:
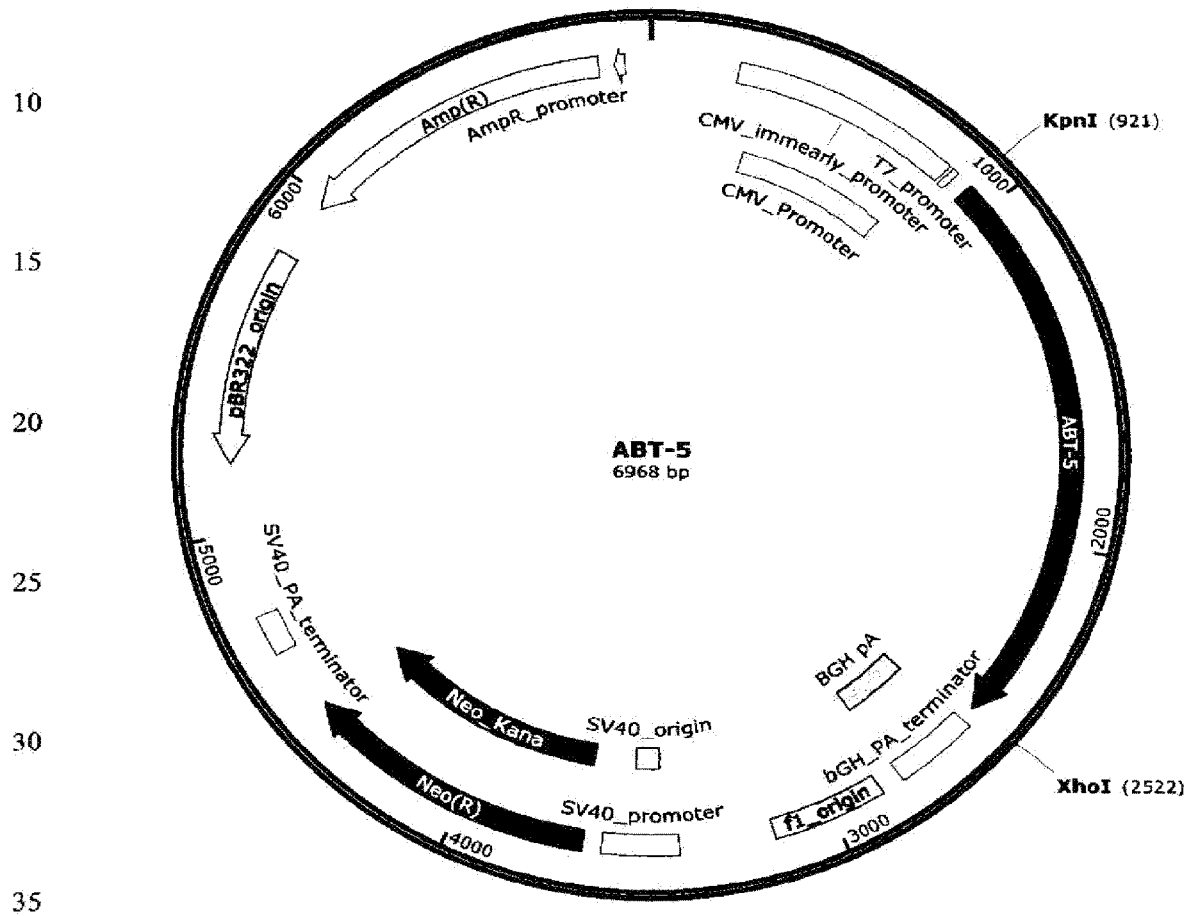
Figure 19:
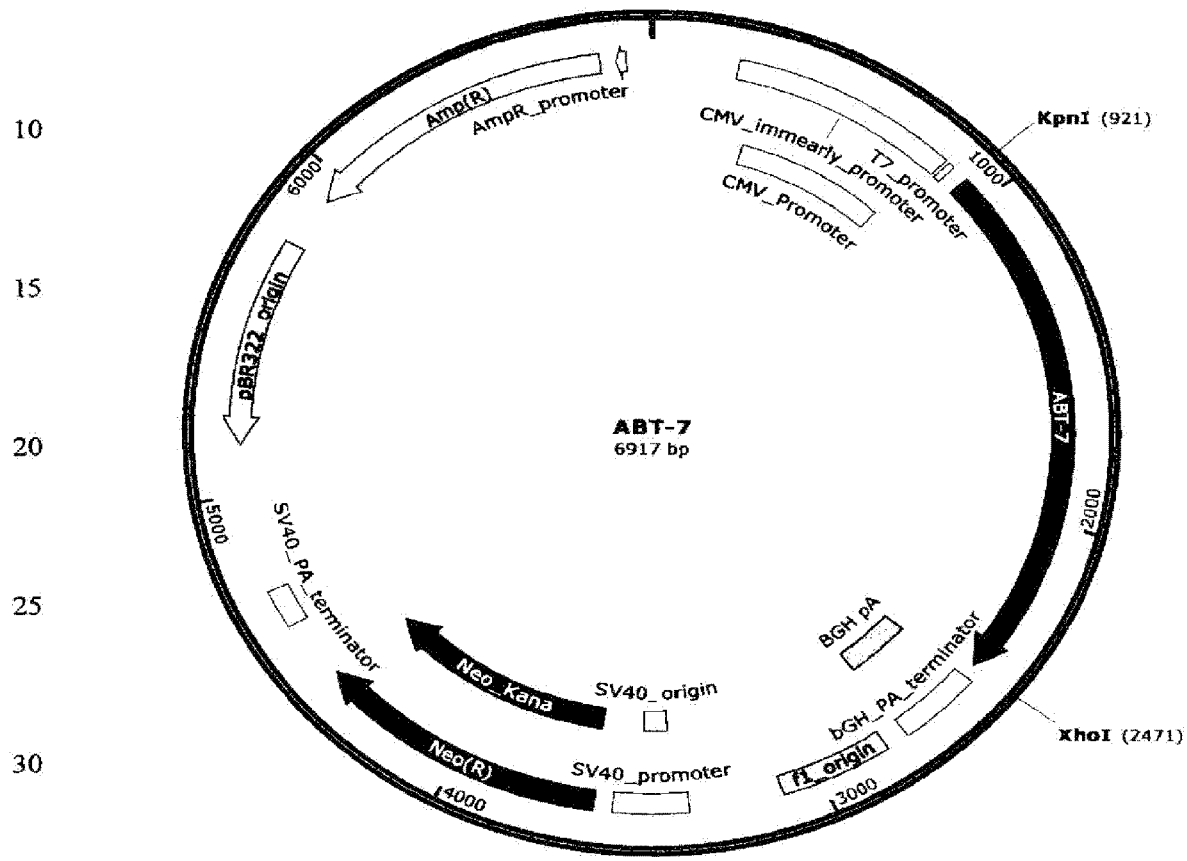
Figure 20:
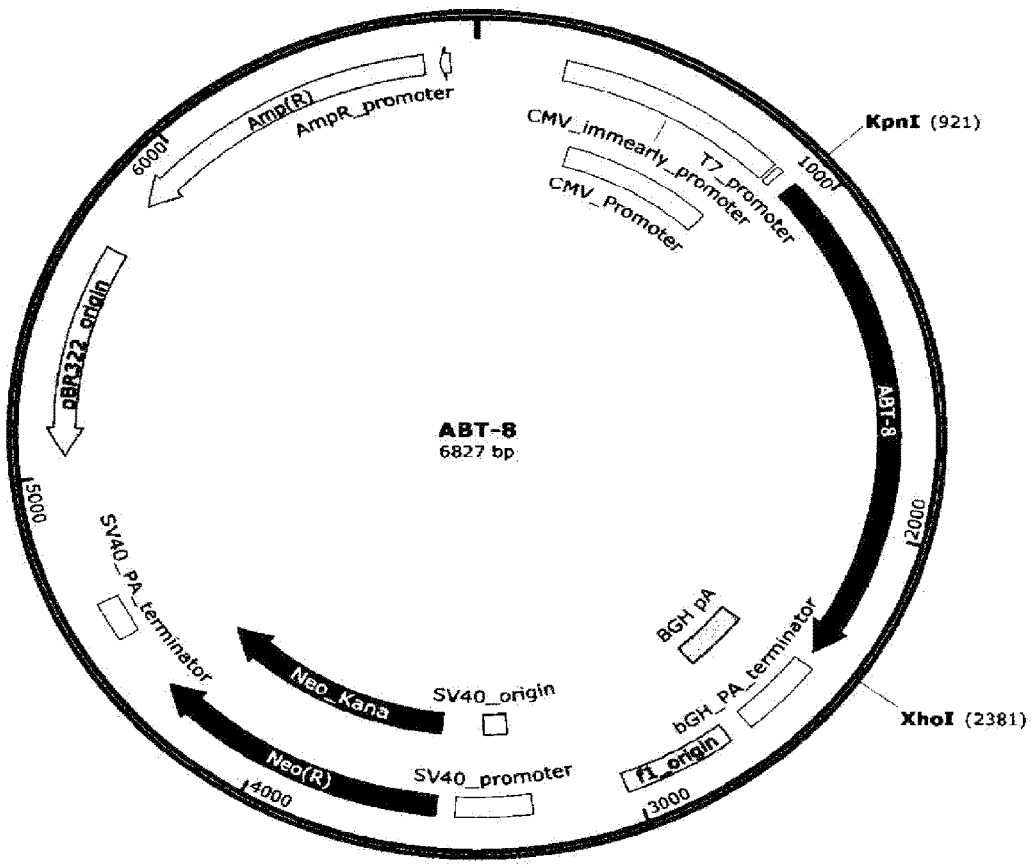

MOLECULE-5 showed a high affinity saturable binding to both HIV infected cells. See FIG. 17.

---

The invention claimed is:

1. An antibody derivative comprising from N- to C-terminus:
   (a) a human CD4 sequence comprising SEQ ID NO:1 and SEQ ID NO:2 or a sequence having at least 96% identity thereto,
   (b) the Fc portion of a human IgG,
   (c) a moiety consisting of a linker polypeptide of sequence (GGGGS)$_n$ wherein n=10, and
   (d) a gp41-derived polypeptide comprising a sequence selected from the group consisting of SEQ ID NO:7, SEQ ID NO:8, SEQ ID NO:9 and SEQ ID NO:10 or a sequence having at least 96% identity thereto.

2. The antibody derivative according to claim 1, wherein the Fc portion of the human IgG comprises IgG1.

3. The antibody derivative according to claim 2, wherein the Fc portion of the human IgG or IgG1 comprises G236A, S239D, A330L and I332E point mutations.

4. The antibody derivative according to claim 1, wherein the gp41-derived polypeptide comprises SEQ ID NO:7.

5. A pharmaceutical composition comprising a therapeutically effective amount of the antibody derivative according to claim 1.

6. A medicament comprising the antibody derivative according to claim 1.

7. A combination comprising the antibody derivative according to claim 1, and at least one therapeutic agent.

8. The combination according to claim 7, wherein the therapeutic agent is an HIV antiretroviral.

9. A kit comprising the antibody derivative according to claim 1, and instructional materials for use.

10. An isolated nucleic acid, wherein the isolated nucleic acid encodes the antibody derivative according to claim 1.

11. The isolated nucleic acid according to claim 10, wherein the isolated nucleic acid is codon optimized.

12. An expression vector comprising the isolated nucleic acid according to claim 10.

13. A host cell comprising the antibody derivative according to claim 1.

14. A method for preparing the antibody derivative according to claim 1 comprising: (a) culturing a host cell comprising a nucleic acid encoding the antibody derivative, (b) expressing the antibody derivative from the nucleic acid, and (c) recovering the antibody derivative from the host cell culture.

15. A method of treatment of HIV infection or AIDS, the method comprising: administering the antibody derivative according to claim 1 to a subject in need thereof.

16. A method of prevention of HIV infection or AIDS, the method comprising: administering the antibody derivative according to claim 1 to a subject in need thereof.

17. A method of inactivating HIV, the method comprising: contacting the virus with the antibody derivative according to claim 1.

18. A method of inducing the expression of gp120 in a HIV-infected cell, the method comprising: contacting the infected cell with the antibody derivative according to claim 1.

19. A method of detecting HIV in a sample, the method comprising: (a) contacting the sample with the antibody derivative according to claim 1, and (b) determining whether the antibody derivative specifically binds to a molecule of the sample.

\* \* \* \* \*

SEQUENCE LISTING

```
<160> NUMBER OF SEQ ID NOS: 42

<210> SEQ ID NO 1
<211> LENGTH: 100
<212> TYPE: PRT
<213> ORGANISM: Homo sapiens
<220> FEATURE:
<221> NAME/KEY: PEPTIDE
<222> LOCATION: (1)..(100)
<223> OTHER INFORMATION: D1 domain of human CD4 receptor (aa)

<400> SEQUENCE: 1
```

```
Lys Val Val Leu Gly Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu
            100
```

<210> SEQ ID NO 2
<211> LENGTH: 78
<212> TYPE: PRT
<213> ORGANISM: Homo sapiens
<220> FEATURE:
<221> NAME/KEY: PEPTIDE
<222> LOCATION: (1)..(78)
<223> OTHER INFORMATION: D2 domain of human CD4 receptor (aa)

<400> SEQUENCE: 2

```
Thr Ala Asn Ser Asp Thr His Leu Leu Gln Gly Gln Ser Leu Thr Leu
1               5                   10                  15

Thr Leu Glu Ser Pro Pro Gly Ser Ser Pro Ser Val Gln Cys Arg Ser
            20                  25                  30

Pro Arg Gly Lys Asn Ile Gln Gly Gly Lys Thr Leu Ser Val Ser Gln
            35                  40                  45

Leu Glu Leu Gln Asp Ser Gly Thr Trp Thr Cys Thr Val Leu Gln Asn
    50                  55                  60

Gln Lys Lys Val Glu Phe Lys Ile Asp Ile Val Val Leu Ala
65                  70                  75
```

<210> SEQ ID NO 3
<211> LENGTH: 232
<212> TYPE: PRT
<213> ORGANISM: Homo sapiens
<220> FEATURE:
<221> NAME/KEY: PEPTIDE
<222> LOCATION: (1)..(232)
<223> OTHER INFORMATION: Fc portion of the human IgG1 (aa)

<400> SEQUENCE: 3

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 4
<211> LENGTH: 232
<212> TYPE: PRT
<213> ORGANISM: Artificial Sequence
<220> FEATURE:
<223> OTHER INFORMATION: Fc portion of the human IgG1 with G236A, S293D,
      A330L and I332E point mutations (aa)
<220> FEATURE:
<221> NAME/KEY: PEPTIDE
<222> LOCATION: (1)..(232)
<223> OTHER INFORMATION: Fc portion of the human IgG1 with G236A, S239D,
      A330L and I332E point mutations (aa)

<400> SEQUENCE: 4

Glu Pro Lys Ser Cys Asp Lys Thr His Thr Cys Pro Pro Cys Pro Ala
1               5                   10                  15

Pro Glu Leu Leu Ala Gly Pro Asp Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Leu Pro Glu Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 5
<211> LENGTH: 5
<212> TYPE: PRT
<213> ORGANISM: Artificial Sequence
<220> FEATURE:
<223> OTHER INFORMATION: Linker polypeptide (aa)
<220> FEATURE:
<221> NAME/KEY: PEPTIDE
<222> LOCATION: (1)..(5)
<223> OTHER INFORMATION: Linker polypeptide (aa)

<400> SEQUENCE: 5

Gly Gly Gly Gly Ser
1               5

<210> SEQ ID NO 6
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: N-terminal region of the human CCR5 receptor
      (aa)

<400> SEQUENCE: 6

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala
            20                  25

<210> SEQ ID NO 7
<211> LENGTH: 36
<212> TYPE: PRT
<213> ORGANISM: Human immunodeficiency virus
<220> FEATURE:
<221> NAME/KEY: PEPTIDE
<222> LOCATION: (1)..(36)
<223> OTHER INFORMATION: T-20 polypeptide (aa)

<400> SEQUENCE: 7

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 8
<211> LENGTH: 39
<212> TYPE: PRT
<213> ORGANISM: Human immunodeficiency virus
<220> FEATURE:
<221> NAME/KEY: PEPTIDE
<222> LOCATION: (1)..(39)
<223> OTHER INFORMATION: T-1249 polypeptide (aa)

<400> SEQUENCE: 8

Trp Gln Glu Trp Glu Gln Lys Ile Thr Ala Leu Leu Glu Gln Ala Gln
```

```
                1               5                  10                  15

Ile Gln Gln Glu Lys Asn Glu Tyr Glu Leu Gln Lys Leu Asp Lys Trp
                20                  25                  30

Ala Ser Leu Trp Glu Trp Phe
        35

<210> SEQ ID NO 9
<211> LENGTH: 34
<212> TYPE: PRT
<213> ORGANISM: Human immunodeficiency virus
<220> FEATURE:
<221> NAME/KEY: PEPTIDE
<222> LOCATION: (1)..(34)
<223> OTHER INFORMATION: C34 polypeptide (aa)

<400> SEQUENCE: 9

Trp Met Glu Trp Asp Arg Glu Ile Asn Asn Tyr Thr Ser Leu Ile His
1               5                  10                  15

Ser Leu Ile Glu Glu Ser Gln Asn Gln Gln Glu Lys Asn Glu Gln Glu
                20                  25                  30

Leu Leu

<210> SEQ ID NO 10
<211> LENGTH: 38
<212> TYPE: PRT
<213> ORGANISM: Human immunodeficiency virus
<220> FEATURE:
<221> NAME/KEY: PEPTIDE
<222> LOCATION: (1)..(38)
<223> OTHER INFORMATION: T-2635 polypeptide (aa)

<400> SEQUENCE: 10

Thr Thr Trp Glu Ala Trp Asp Arg Ala Ile Ala Glu Tyr Ala Ala Arg
1               5                  10                  15

Ile Glu Ala Leu Ile Arg Ala Ala Gln Glu Gln Gln Glu Lys Asn Glu
                20                  25                  30

Ala Ala Leu Arg Glu Leu
        35

<210> SEQ ID NO 11
<211> LENGTH: 404
<212> TYPE: PRT
<213> ORGANISM: Artificial Sequence
<220> FEATURE:
<223> OTHER INFORMATION: Fusion protein MOLECULE-0 (aa)
<220> FEATURE:
<221> NAME/KEY: PEPTIDE
<222> LOCATION: (1)..(404)
<223> OTHER INFORMATION: Fusion protein MOLECULE-0 (aa)

<400> SEQUENCE: 11

Lys Lys Gly Asp Thr Val Glu Leu Thr Cys Thr Ala Ser Gln Lys Lys
1               5                  10                  15

Ser Ile Gln Phe His Trp Lys Asn Ser Asn Gln Ile Lys Ile Leu Gly
                20                  25                  30

Asn Gln Gly Ser Phe Leu Thr Lys Gly Pro Ser Lys Leu Asn Asp Arg
        35                  40                  45

Ala Asp Ser Arg Arg Ser Leu Trp Asp Gln Gly Asn Phe Pro Leu Ile
    50                  55                  60

Ile Lys Asn Leu Lys Ile Glu Asp Ser Asp Thr Tyr Ile Cys Glu Val
65                  70                  75                  80

Glu Asp Gln Lys Glu Glu Val Gln Leu Leu Val Phe Gly Leu Thr Ala
```

```
                        85                  90                  95
Asn Ser Asp Thr His Leu Leu Gln Gly Gln Ser Leu Thr Leu Thr Leu
                100                 105                 110

Glu Ser Pro Pro Gly Ser Ser Pro Ser Val Gln Cys Arg Ser Pro Arg
            115                 120                 125

Gly Lys Asn Ile Gln Gly Gly Lys Thr Leu Ser Val Ser Gln Leu Glu
        130                 135                 140

Leu Gln Asp Ser Gly Thr Trp Thr Cys Thr Val Leu Gln Asn Gln Lys
145                 150                 155                 160

Lys Val Glu Phe Lys Ile Asp Ile Val Val Leu Ala Glu Pro Lys Ser
                165                 170                 175

Cys Asp Lys Thr His Thr Cys Pro Pro Cys Pro Ala Pro Glu Leu Leu
                180                 185                 190

Gly Gly Pro Ser Val Phe Leu Phe Pro Pro Lys Pro Lys Asp Thr Leu
            195                 200                 205

Met Ile Ser Arg Thr Pro Glu Val Thr Cys Val Val Val Asp Val Ser
        210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
                260                 265                 270

Gly Lys Glu Tyr Lys Cys Lys Val Ser Asn Lys Ala Leu Pro Ala Pro
            275                 280                 285

Ile Glu Lys Thr Ile Ser Lys Ala Lys Gly Gln Pro Arg Glu Pro Gln
        290                 295                 300

Val Tyr Thr Leu Pro Pro Ser Arg Asp Glu Leu Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
                340                 345                 350

Pro Val Leu Asp Ser Asp Gly Ser Phe Phe Leu Tyr Ser Lys Leu Thr
            355                 360                 365

Val Asp Lys Ser Arg Trp Gln Gln Gly Asn Val Phe Ser Cys Ser Val
        370                 375                 380

Met His Glu Ala Leu His Asn His Tyr Thr Gln Lys Ser Leu Ser Leu
385                 390                 395                 400

Ser Pro Gly Lys

<210> SEQ ID NO 12
<211> LENGTH: 457
<212> TYPE: PRT
<213> ORGANISM: Artificial Sequence
<220> FEATURE:
<223> OTHER INFORMATION: Fusion protein MOLECULE-1 (aa)
<220> FEATURE:
<221> NAME/KEY: PEPTIDE
<222> LOCATION: (1)..(457)
<223> OTHER INFORMATION: Fusion protein MOLECULE-1 (aa)

<400> SEQUENCE: 12

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
```

```
                      20                  25                  30
Gly Asp Thr Val Glu Leu Thr Cys Thr Ala Ser Gln Lys Lys Ser Ile
             35                  40                  45
Gln Phe His Trp Lys Asn Ser Asn Gln Ile Lys Ile Leu Gly Asn Gln
 50                  55                  60
Gly Ser Phe Leu Thr Lys Gly Pro Ser Lys Leu Asn Asp Arg Ala Asp
 65                  70                  75                  80
Ser Arg Arg Ser Leu Trp Asp Gln Gly Asn Phe Pro Leu Ile Ile Lys
                 85                  90                  95
Asn Leu Lys Ile Glu Asp Ser Asp Thr Tyr Ile Cys Glu Val Glu Asp
             100                 105                 110
Gln Lys Glu Glu Val Gln Leu Leu Val Phe Gly Leu Thr Ala Asn Ser
         115                 120                 125
Asp Thr His Leu Leu Gln Gly Gln Ser Leu Thr Leu Thr Leu Glu Ser
         130                 135                 140
Pro Pro Gly Ser Ser Pro Ser Val Gln Cys Arg Ser Pro Arg Gly Lys
145                 150                 155                 160
Asn Ile Gln Gly Gly Lys Thr Leu Ser Val Ser Gln Leu Glu Leu Gln
                 165                 170                 175
Asp Ser Gly Thr Trp Thr Cys Thr Val Leu Gln Asn Gln Lys Lys Val
             180                 185                 190
Glu Phe Lys Ile Asp Ile Val Val Leu Ala Ala Ala Asp Pro Glu Pro
         195                 200                 205
Lys Ser Cys Asp Lys Thr His Thr Cys Pro Pro Cys Pro Ala Pro Glu
         210                 215                 220
Leu Leu Gly Gly Pro Ser Val Phe Leu Phe Pro Pro Lys Pro Lys Asp
225                 230                 235                 240
Thr Leu Met Ile Ser Arg Thr Pro Glu Val Thr Cys Val Val Val Asp
                 245                 250                 255
Val Ser His Glu Asp Pro Glu Val Lys Phe Asn Trp Tyr Val Asp Gly
             260                 265                 270
Val Glu Val His Asn Ala Lys Thr Lys Pro Arg Glu Glu Gln Tyr Asn
         275                 280                 285
Ser Thr Tyr Arg Val Val Ser Val Leu Thr Val Leu His Gln Asp Trp
         290                 295                 300
Leu Asn Gly Lys Glu Tyr Lys Cys Lys Val Ser Asn Lys Ala Leu Pro
305                 310                 315                 320
Ala Pro Ile Glu Lys Thr Ile Ser Lys Ala Lys Gly Gln Pro Arg Glu
                 325                 330                 335
Pro Gln Val Tyr Thr Leu Pro Pro Ser Arg Asp Glu Leu Thr Lys Asn
             340                 345                 350
Gln Val Ser Leu Thr Cys Leu Val Lys Gly Phe Tyr Pro Ser Asp Ile
         355                 360                 365
Ala Val Glu Trp Glu Ser Asn Gly Gln Pro Glu Asn Asn Tyr Lys Thr
         370                 375                 380
Thr Pro Pro Val Leu Asp Ser Asp Gly Ser Phe Phe Leu Tyr Ser Lys
385                 390                 395                 400
Leu Thr Val Asp Lys Ser Arg Trp Gln Gln Gly Asn Val Phe Ser Cys
                 405                 410                 415
Ser Val Met His Glu Ala Leu His Asn His Tyr Thr Gln Lys Ser Leu
             420                 425                 430
Ser Leu Ser Pro Gly Lys Gly Gly Gly Gly Asp Tyr Ala Asp Tyr
         435                 440                 445
```

```
Asp Gly Gly Tyr Tyr Tyr Asp Met Asp
    450                 455

<210> SEQ ID NO 13
<211> LENGTH: 457
<212> TYPE: PRT
<213> ORGANISM: Artificial Sequence
<220> FEATURE:
<223> OTHER INFORMATION: Fusion protein MOLECULE-2 (aa)
<220> FEATURE:
<221> NAME/KEY: PEPTIDE
<222> LOCATION: (1)..(457)
<223> OTHER INFORMATION: Fusion protein MOLECULE-2 (aa)

<400> SEQUENCE: 13

Met Pro Met Gly Ser Leu Gln Pro Leu Ala Thr Leu Tyr Leu Leu Gly
1               5                   10                  15

Met Leu Val Ala Ser Val Leu Ala Lys Lys Val Val Leu Gly Lys Lys
            20                  25                  30

Gly Asp Thr Val Glu Leu Thr Cys Thr Ala Ser Gln Lys Lys Ser Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Ala Asp
65                  70                  75                  80

Ser Arg Arg Ser Leu Trp Asp Gln Gly Asn Phe Pro Leu Ile Ile Lys
                85                  90                  95

Asn Leu Lys Ile Glu Asp Ser Asp Thr Tyr Ile Cys Glu Val Glu Asp
            100                 105                 110

Gln Lys Glu Glu Val Gln Leu Leu Val Phe Gly Leu Thr Ala Asn Ser
        115                 120                 125

Asp Thr His Leu Leu Gln Gly Gln Ser Leu Thr Leu Thr Leu Glu Ser
    130                 135                 140

Pro Pro Gly Ser Ser Pro Ser Val Gln Cys Arg Ser Pro Arg Gly Lys
145                 150                 155                 160

Asn Ile Gln Gly Gly Lys Thr Leu Ser Val Ser Gln Leu Glu Leu Gln
                165                 170                 175

Asp Ser Gly Thr Trp Thr Cys Thr Val Leu Gln Asn Gln Lys Lys Val
            180                 185                 190

Glu Phe Lys Ile Asp Ile Val Val Leu Ala Ala Ala Asp Pro Glu Pro
        195                 200                 205

Lys Ser Cys Asp Lys Thr His Thr Cys Pro Pro Cys Pro Ala Pro Glu
210                 215                 220

Leu Leu Ala Gly Pro Asp Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Lys Phe Asn Trp Tyr Val Asp Gly
            260                 265                 270

Val Glu Val His Asn Ala Lys Thr Lys Pro Arg Glu Glu Gln Tyr Asn
        275                 280                 285

Ser Thr Tyr Arg Val Val Ser Val Leu Thr Val Leu His Gln Asp Trp
    290                 295                 300

Leu Asn Gly Lys Glu Tyr Lys Cys Lys Val Ser Asn Lys Ala Leu Pro
305                 310                 315                 320

Leu Pro Glu Glu Lys Thr Ile Ser Lys Ala Lys Gly Gln Pro Arg Glu
```

```
                    325                 330                 335
Pro Gln Val Tyr Thr Leu Pro Pro Ser Arg Asp Glu Leu Thr Lys Asn
            340                 345                 350
Gln Val Ser Leu Thr Cys Leu Val Lys Gly Phe Tyr Pro Ser Asp Ile
            355                 360                 365
Ala Val Glu Trp Glu Ser Asn Gly Gln Pro Glu Asn Asn Tyr Lys Thr
            370                 375                 380
Thr Pro Pro Val Leu Asp Ser Asp Gly Ser Phe Phe Leu Tyr Ser Lys
385                 390                 395                 400
Leu Thr Val Asp Lys Ser Arg Trp Gln Gln Gly Asn Val Phe Ser Cys
                405                 410                 415
Ser Val Met His Glu Ala Leu His Asn His Tyr Thr Gln Lys Ser Leu
                420                 425                 430
Ser Leu Ser Pro Gly Lys Gly Gly Gly Gly Asp Tyr Ala Asp Tyr
            435                 440                 445
Asp Gly Gly Tyr Tyr Tyr Asp Met Asp
        450                 455

<210> SEQ ID NO 14
<211> LENGTH: 478
<212> TYPE: PRT
<213> ORGANISM: Artificial Sequence
<220> FEATURE:
<223> OTHER INFORMATION: Fusion protein MOLECULE-3
<220> FEATURE:
<221> NAME/KEY: PEPTIDE
<222> LOCATION: (1)..(478)
<223> OTHER INFORMATION: Fusion protein MOLECULE-3 (aa)

<400> SEQUENCE: 14

Met Asn Arg Gly Val Pro Phe Arg His Leu Leu Leu Val Leu Gln Leu
1               5                   10                  15
Ala Leu Leu Pro Ala Ala Thr Gln Gly Lys Lys Val Val Leu Gly Lys
                20                  25                  30
Lys Gly Asp Thr Val Glu Leu Thr Cys Thr Ala Ser Gln Lys Lys Ser
            35                  40                  45
Ile Gln Phe His Trp Lys Asn Ser Asn Gln Ile Lys Ile Leu Gly Asn
        50                  55                  60
Gln Gly Ser Phe Leu Thr Lys Gly Pro Ser Lys Leu Asn Asp Arg Ala
65                  70                  75                  80
Asp Ser Arg Arg Ser Leu Trp Asp Gln Gly Asn Phe Pro Leu Ile Ile
                85                  90                  95
Lys Asn Leu Lys Ile Glu Asp Ser Asp Thr Tyr Ile Cys Glu Val Glu
                100                 105                 110
Asp Gln Lys Glu Glu Val Gln Leu Leu Val Phe Gly Leu Thr Ala Asn
            115                 120                 125
Ser Asp Thr His Leu Leu Gln Gly Gln Ser Leu Thr Leu Thr Leu Glu
        130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Glu Pro Lys Ser Cys
        195                 200                 205
```

```
Asp Lys Thr His Thr Cys Pro Pro Cys Pro Ala Pro Glu Leu Leu Ala
    210                 215                 220

Gly Pro Asp Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
290                 295                 300

Lys Glu Tyr Lys Cys Lys Val Ser Asn Lys Ala Leu Pro Leu Pro Glu
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys Gly Gly Gly Gly Ala Ala Ala Tyr Thr Ser Leu Ile His
        435                 440                 445

Ser Leu Ile Glu Glu Ser Gln Asn Gln Gln Glu Lys Asn Glu Gln Glu
        450                 455                 460

Leu Leu Glu Leu Asp Lys Trp Ala Ser Leu Trp Asn Trp Phe
465                 470                 475

<210> SEQ ID NO 15
<211> LENGTH: 468
<212> TYPE: PRT
<213> ORGANISM: Artificial Sequence
<220> FEATURE:
<223> OTHER INFORMATION: Fusion protein MOLECULE-4 (aa)
<220> FEATURE:
<221> NAME/KEY: PEPTIDE
<222> LOCATION: (1)..(468)
<223> OTHER INFORMATION: Fusion protein MOLECULE-4 (aa)

<400> SEQUENCE: 15

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80
```

```
Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Glu Pro Lys Ser Cys
        195                 200                 205

Asp Lys Thr His Thr Cys Pro Pro Cys Pro Ala Pro Glu Leu Leu Ala
    210                 215                 220

Gly Pro Asp Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Leu Pro Glu
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys Gly Gly Gly Gly Asp Tyr Gln Val Ser Ser Pro Ile Tyr
        435                 440                 445

Asp Ile Asn Tyr Tyr Thr Ser Glu Pro Cys Gln Lys Ile Asn Val Lys
    450                 455                 460

Gln Ile Ala Ala
465

<210> SEQ ID NO 16
<211> LENGTH: 529
```

```
<212> TYPE: PRT
<213> ORGANISM: Artificial Sequence
<220> FEATURE:
<223> OTHER INFORMATION: Fusion protein MOLECULE-5 (aa)
<220> FEATURE:
<221> NAME/KEY: PEPTIDE
<222> LOCATION: (1)..(529)
<223> OTHER INFORMATION: Fusion protein MOLECULE-5 (aa)

<400> SEQUENCE: 16

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Glu Pro Lys Ser Cys
            195                 200                 205

Asp Lys Thr His Thr Cys Pro Pro Cys Pro Ala Pro Glu Leu Leu Ala
        210                 215                 220

Gly Pro Asp Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Leu Pro Glu
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365
```

-continued

```
Trp Glu Ser Asn Gly Gln Pro Glu Asn Asn Tyr Lys Thr Thr Pro Pro
        370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys Gly Gly Gly Asp Tyr Gln Val Ser Ser Pro Ile Tyr
        435                 440                 445

Asp Ile Asn Tyr Tyr Thr Ser Glu Pro Cys Gln Lys Ile Asn Val Lys
    450                 455                 460

Gln Ile Ala Ala Gly Gly Gly Ser Gly Gly Gly Ser Gly Gly
465                 470                 475                 480

Gly Gly Ser Gly Gly Gly Ser Gly Gly Gly Ser Tyr Thr Ser
                485                 490                 495

Leu Ile His Ser Leu Ile Glu Glu Ser Gln Asn Gln Gln Glu Lys Asn
            500                 505                 510

Glu Gln Glu Leu Leu Glu Leu Asp Lys Trp Ala Ser Leu Trp Asn Trp
        515                 520                 525

Phe
```

```
<210> SEQ ID NO 17
<211> LENGTH: 435
<212> TYPE: PRT
<213> ORGANISM: Artificial Sequence
<220> FEATURE:
<223> OTHER INFORMATION: Fusion protein MOLECULE-6 (aa)
<220> FEATURE:
<221> NAME/KEY: PEPTIDE
<222> LOCATION: (1)..(435)
<223> OTHER INFORMATION: Fusion protein MOLECULE-6 (aa)

<400> SEQUENCE: 17
```

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175
```

```
Gln Asp Ser Gly Thr Trp Thr Cys Thr Val Leu Gln Asn Gln Lys Lys
                180                 185                 190

Val Glu Phe Lys Ile Asp Ile Val Val Leu Ala Glu Pro Lys Ser Cys
            195                 200                 205

Asp Lys Thr His Thr Cys Pro Pro Cys Pro Ala Pro Glu Leu Leu Ala
        210                 215                 220

Gly Pro Asp Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Leu Pro Glu
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys
        435

<210> SEQ ID NO 18
<211> LENGTH: 513
<212> TYPE: PRT
<213> ORGANISM: Artificial Sequence
<220> FEATURE:
<223> OTHER INFORMATION: Fusion protein MOLECULE-7 (aa)
<220> FEATURE:
<221> NAME/KEY: PEPTIDE
<222> LOCATION: (1)..(513)
<223> OTHER INFORMATION: Fusion protein MOLECULE-7 (aa)

<400> SEQUENCE: 18

Met Trp Leu Gln Ser Leu Leu Leu Leu Gly Thr Val Ala Cys Ser Ile
1               5                   10                  15

Ser Lys Lys Val Val Leu Gly Lys Lys Gly Asp Thr Val Glu Leu Thr
            20                  25                  30

Cys Thr Ala Ser Gln Lys Lys Ser Ile Gln Phe His Trp Lys Asn Ser
        35                  40                  45

Asn Gln Ile Lys Ile Leu Gly Asn Gln Gly Ser Phe Leu Thr Lys Gly
    50                  55                  60

Pro Ser Lys Leu Asn Asp Arg Ala Asp Ser Arg Arg Ser Leu Trp Asp
```

```
                65                  70                  75                  80
        Gln Gly Asn Phe Pro Leu Ile Ile Lys Asn Leu Lys Ile Glu Asp Ser
                        85                  90                  95

Asp Thr Tyr Ile Cys Glu Val Glu Asp Gln Lys Glu Glu Val Gln Leu
                        100                 105                 110

Leu Val Phe Gly Leu Thr Ala Asn Ser Asp Thr His Leu Leu Gln Gly
                        115                 120                 125

Gln Ser Leu Thr Leu Thr Leu Glu Ser Pro Pro Gly Ser Ser Pro Ser
                        130                 135                 140

Val Gln Cys Arg Ser Pro Arg Gly Lys Asn Ile Gln Gly Gly Lys Thr
        145                 150                 155                 160

Leu Ser Val Ser Gln Leu Glu Leu Gln Asp Ser Gly Thr Trp Thr Cys
                        165                 170                 175

Thr Val Leu Gln Asn Gln Lys Lys Val Glu Phe Lys Ile Asp Ile Val
                        180                 185                 190

Val Leu Ala Glu Pro Lys Ser Cys Asp Lys Thr His Thr Cys Pro Pro
                        195                 200                 205

Cys Pro Ala Pro Glu Leu Leu Ala Gly Pro Asp Val Phe Leu Phe Pro
        210                 215                 220

Pro Lys Pro Lys Asp Thr Leu Met Ile Ser Arg Thr Pro Glu Val Thr
        225                 230                 235                 240

Cys Val Val Val Asp Val Ser His Glu Asp Pro Glu Val Lys Phe Asn
                        245                 250                 255

Trp Tyr Val Asp Gly Val Glu Val His Asn Ala Lys Thr Lys Pro Arg
                        260                 265                 270

Glu Glu Gln Tyr Asn Ser Thr Tyr Arg Val Val Ser Val Leu Thr Val
                        275                 280                 285

Leu His Gln Asp Trp Leu Asn Gly Lys Glu Tyr Lys Cys Lys Val Ser
                        290                 295                 300

Asn Lys Ala Leu Pro Leu Pro Glu Glu Lys Thr Ile Ser Lys Ala Lys
        305                 310                 315                 320

Gly Gln Pro Arg Glu Pro Gln Val Tyr Thr Leu Pro Pro Ser Arg Asp
                        325                 330                 335

Glu Leu Thr Lys Asn Gln Val Ser Leu Thr Cys Leu Val Lys Gly Phe
                        340                 345                 350

Tyr Pro Ser Asp Ile Ala Val Glu Trp Glu Ser Asn Gly Gln Pro Glu
                        355                 360                 365

Asn Asn Tyr Lys Thr Thr Pro Pro Val Leu Asp Ser Asp Gly Ser Phe
                        370                 375                 380

Phe Leu Tyr Ser Lys Leu Thr Val Asp Lys Ser Arg Trp Gln Gln Gly
        385                 390                 395                 400

Asn Val Phe Ser Cys Ser Val Met His Glu Ala Leu His Asn His Tyr
                        405                 410                 415

Thr Gln Lys Ser Leu Ser Leu Ser Pro Gly Lys Gly Gly Gly Gly Ser
                        420                 425                 430

Gly Gly Gly Gly Ser Gly Gly Gly Gly Ser Gly Gly Gly Gly Ser Gly
                        435                 440                 445

Gly Gly Gly Ser Gly Gly Gly Gly Ser Gly Gly Gly Gly Ser Gly Gly
        450                 455                 460

Gly Gly Ser Gly Gly Gly Gly Ser Gly Gly Gly Gly Ser Tyr Thr Ser
        465                 470                 475                 480

Leu Ile His Ser Leu Ile Glu Glu Ser Gln Asn Gln Gln Glu Lys Asn
                        485                 490                 495
```

```
Glu Gln Glu Leu Leu Glu Leu Asp Lys Trp Ala Ser Leu Trp Asn Trp
            500                 505                 510

Phe

<210> SEQ ID NO 19
<211> LENGTH: 483
<212> TYPE: PRT
<213> ORGANISM: Artificial Sequence
<220> FEATURE:
<223> OTHER INFORMATION: Fusion protein MOLECULE-8 (aa)
<220> FEATURE:
<221> NAME/KEY: PEPTIDE
<222> LOCATION: (1)..(483)
<223> OTHER INFORMATION: Fusion protein MOLECULE-8 (aa)

<400> SEQUENCE: 19

Met Trp Leu Gln Ser Leu Leu Leu Gly Thr Val Ala Cys Ser Ile
1               5                   10                  15

Ser Lys Lys Val Val Leu Gly Lys Lys Gly Asp Thr Val Glu Leu Thr
                20                  25                  30

Cys Thr Ala Ser Gln Lys Lys Ser Ile Gln Phe His Trp Lys Asn Ser
            35                  40                  45

Asn Gln Ile Lys Ile Leu Gly Asn Gln Gly Ser Phe Leu Thr Lys Gly
        50                  55                  60

Pro Ser Lys Leu Asn Asp Arg Ala Asp Ser Arg Arg Ser Leu Trp Asp
65                  70                  75                  80

Gln Gly Asn Phe Pro Leu Ile Ile Lys Asn Leu Lys Ile Glu Asp Ser
                85                  90                  95

Asp Thr Tyr Ile Cys Glu Val Glu Asp Gln Lys Glu Glu Val Gln Leu
            100                 105                 110

Leu Val Phe Gly Leu Thr Ala Asn Ser Asp Thr His Leu Leu Gln Gly
        115                 120                 125

Gln Ser Leu Thr Leu Thr Leu Glu Ser Pro Pro Gly Ser Ser Pro Ser
    130                 135                 140

Val Gln Cys Arg Ser Pro Arg Gly Lys Asn Ile Gln Gly Gly Lys Thr
145                 150                 155                 160

Leu Ser Val Ser Gln Leu Glu Leu Gln Asp Ser Gly Thr Trp Thr Cys
                165                 170                 175

Thr Val Leu Gln Asn Gln Lys Lys Val Glu Phe Lys Ile Asp Ile Val
            180                 185                 190

Val Leu Ala Glu Pro Lys Ser Cys Asp Lys Thr His Thr Cys Pro Pro
        195                 200                 205

Cys Pro Ala Pro Glu Leu Leu Ala Gly Pro Asp Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
    290                 295                 300

Asn Lys Ala Leu Pro Leu Pro Glu Glu Lys Thr Ile Ser Lys Ala Lys
305                 310                 315                 320
```

```
Gly Gln Pro Arg Glu Pro Gln Val Tyr Thr Leu Pro Pro Ser Arg Asp
                325                 330                 335

Glu Leu Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
    370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys Gly Gly Gly Gly Ser
            420                 425                 430

Gly Gly Gly Gly Ser Gly Gly Gly Ser Gly Gly Gly Gly Ser Tyr
        435                 440                 445

Thr Ser Leu Ile His Ser Leu Ile Glu Glu Ser Gln Asn Gln Gln Glu
    450                 455                 460

Lys Asn Glu Gln Glu Leu Leu Glu Leu Asp Lys Trp Ala Ser Leu Trp
465                 470                 475                 480

Asn Trp Phe

<210> SEQ ID NO 20
<211> LENGTH: 509
<212> TYPE: PRT
<213> ORGANISM: Artificial Sequence
<220> FEATURE:
<223> OTHER INFORMATION: Fusion protein MOLECULE-10 (aa)
<220> FEATURE:
<221> NAME/KEY: PEPTIDE
<222> LOCATION: (1)..(509)
<223> OTHER INFORMATION: Fusion protein MOLECULE-10 (aa)

<400> SEQUENCE: 20

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175
```

```
Gln Asp Ser Gly Thr Trp Thr Cys Thr Val Leu Gln Asn Gln Lys Lys
            180                 185                 190

Val Glu Phe Lys Ile Asp Ile Val Val Leu Ala Glu Pro Lys Ser Cys
        195                 200                 205

Asp Lys Thr His Thr Cys Pro Pro Cys Pro Ala Pro Glu Leu Leu Ala
    210                 215                 220

Gly Pro Asp Val Phe Leu Phe Pro Pro Lys Pro Lys Asp Thr Leu Met
225                 230                 235                 240

Ile Ser Arg Thr Pro Glu Val Thr Cys Val Val Val Asp Val Ser His
                245                 250                 255

Glu Asp Pro Glu Val Lys Phe Asn Trp Tyr Val Asp Gly Val Glu Val
            260                 265                 270

His Asn Ala Lys Thr Lys Pro Arg Glu Glu Gln Tyr Asn Ser Thr Tyr
        275                 280                 285

Arg Val Val Ser Val Leu Thr Val Leu His Gln Asp Trp Leu Asn Gly
    290                 295                 300

Lys Glu Tyr Lys Cys Lys Val Ser Asn Lys Ala Leu Pro Leu Pro Glu
305                 310                 315                 320

Glu Lys Thr Ile Ser Lys Ala Lys Gly Gln Pro Arg Glu Pro Gln Val
                325                 330                 335

Tyr Thr Leu Pro Pro Ser Arg Asp Glu Leu Thr Lys Asn Gln Val Ser
            340                 345                 350

Leu Thr Cys Leu Val Lys Gly Phe Tyr Pro Ser Asp Ile Ala Val Glu
        355                 360                 365

Trp Glu Ser Asn Gly Gln Pro Glu Asn Asn Tyr Lys Thr Thr Pro Pro
    370                 375                 380

Val Leu Asp Ser Asp Gly Ser Phe Phe Leu Tyr Ser Lys Leu Thr Val
385                 390                 395                 400

Asp Lys Ser Arg Trp Gln Gln Gly Asn Val Phe Ser Cys Ser Val Met
                405                 410                 415

His Glu Ala Leu His Asn His Tyr Thr Gln Lys Ser Leu Ser Leu Ser
            420                 425                 430

Pro Gly Lys Gly Gly Gly Asp Tyr Gln Val Ser Ser Pro Ile Tyr
        435                 440                 445

Asp Ile Asn Tyr Tyr Thr Ser Glu Pro Cys Gln Lys Ile Asn Val Lys
    450                 455                 460

Gln Ile Ala Ala Gly Gly Gly Ser Tyr Thr Ser Leu Ile His Ser
465                 470                 475                 480

Leu Ile Glu Glu Ser Gln Asn Gln Gln Glu Lys Asn Glu Gln Glu Leu
                485                 490                 495

Leu Glu Leu Asp Lys Trp Ala Ser Leu Trp Asn Trp Phe
            500                 505

<210> SEQ ID NO 21
<211> LENGTH: 541
<212> TYPE: PRT
<213> ORGANISM: Artificial Sequence
<220> FEATURE:
<223> OTHER INFORMATION: Fusion protein MOLECULE-11 (aa)
<220> FEATURE:
<221> NAME/KEY: PEPTIDE
<222> LOCATION: (1)..(541)
<223> OTHER INFORMATION: Fusion protein MOLECULE-11 (aa)

<400> SEQUENCE: 21

Met Trp Leu Gln Ser Leu Leu Leu Leu Gly Thr Val Ala Cys Ser Ile
```

```
1               5                   10                  15
Ser Lys Lys Val Val Leu Gly Lys Lys Gly Asp Thr Val Glu Leu Thr
                20                  25                  30

Cys Thr Ala Ser Gln Lys Lys Ser Ile Gln Phe His Trp Lys Asn Ser
                35                  40                  45

Asn Gln Ile Lys Ile Leu Gly Asn Gln Gly Ser Phe Leu Thr Lys Gly
                50                  55                  60

Pro Ser Lys Leu Asn Asp Arg Ala Asp Ser Arg Arg Ser Leu Trp Asp
65                  70                  75                  80

Gln Gly Asn Phe Pro Leu Ile Ile Lys Asn Leu Lys Ile Glu Asp Ser
                85                  90                  95

Asp Thr Tyr Ile Cys Glu Val Glu Asp Gln Lys Glu Val Gln Leu
                100                 105                 110

Leu Val Phe Gly Leu Thr Ala Asn Ser Asp Thr His Leu Leu Gln Gly
                115                 120                 125

Gln Ser Leu Thr Leu Thr Leu Glu Ser Pro Pro Gly Ser Ser Pro Ser
                130                 135                 140

Val Gln Cys Arg Ser Pro Arg Gly Lys Asn Ile Gln Gly Gly Lys Thr
145                 150                 155                 160

Leu Ser Val Ser Gln Leu Glu Leu Gln Asp Ser Gly Thr Trp Thr Cys
                165                 170                 175

Thr Val Leu Gln Asn Gln Lys Lys Val Glu Phe Lys Ile Asp Ile Val
                180                 185                 190

Val Leu Ala Glu Pro Lys Ser Cys Asp Lys Thr His Thr Cys Pro Pro
                195                 200                 205

Cys Pro Ala Pro Glu Leu Leu Ala Gly Pro Asp Val Phe Leu Phe Pro
210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr Val
                275                 280                 285

Leu His Gln Asp Trp Leu Asn Gly Lys Glu Tyr Lys Cys Lys Val Ser
                290                 295                 300

Asn Lys Ala Leu Pro Leu Pro Glu Glu Lys Thr Ile Ser Lys Ala Lys
305                 310                 315                 320

Gly Gln Pro Arg Glu Pro Gln Val Tyr Thr Leu Pro Pro Ser Arg Asp
                325                 330                 335

Glu Leu Thr Lys Asn Gln Val Ser Leu Thr Cys Leu Val Lys Gly Phe
                340                 345                 350

Tyr Pro Ser Asp Ile Ala Val Glu Trp Glu Ser Asn Gly Gln Pro Glu
                355                 360                 365

Asn Asn Tyr Lys Thr Thr Pro Pro Val Leu Asp Ser Asp Gly Ser Phe
                370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys Gly Gly Gly Gly Asp
                420                 425                 430
```

```
Tyr Gln Val Ser Ser Pro Ile Tyr Asp Ile Asn Tyr Tyr Thr Ser Glu
        435                 440                 445

Pro Cys Gln Lys Ile Asn Val Lys Gln Ile Ala Ala Gly Gly Gly Gly
    450                 455                 460

Ser Gly Gly Gly Ser Gly Gly Gly Ser Gly Gly Gly Ser
465                 470                 475                 480

Gly Gly Gly Gly Ser Gly Gly Gly Ser Gly Gly Gly Ser Gly
                485                 490                 495

Gly Gly Gly Ser Gly Gly Gly Ser Tyr Thr Ser Leu Ile His Ser
                500                 505                 510

Leu Ile Glu Glu Ser Gln Asn Gln Gln Glu Lys Asn Glu Gln Glu Leu
        515                 520                 525

Leu Glu Leu Asp Lys Trp Ala Ser Leu Trp Asn Trp Phe
    530                 535                 540

<210> SEQ ID NO 22
<211> LENGTH: 300
<212> TYPE: DNA
<213> ORGANISM: Homo sapiens
<220> FEATURE:
<221> NAME/KEY: gene
<222> LOCATION: (1)..(300)
<223> OTHER INFORMATION: D1 domain of human CD4 receptor (nt)

<400> SEQUENCE: 22
aagaaagtgg tgctgggcaa aaagggcgac accgtggaac tgacctgcac cgccagccag      60
aagaagtcca tccagttcca ctggaagaac agcaaccaga tcaagatcct gggcaaccag     120
ggcagcttcc tgaccaaggg ccccagcaag ctgaacgaca gagccgactc tcggcggagc     180
ctgtgggacc agggcaattt ccccactgat catcaagaacc tgaagatcga ggacagcgac     240
acctacatct gcgaggtgga agatcagaaa gaagaggtgc agctgctggt gttcggcctg     300

<210> SEQ ID NO 23
<211> LENGTH: 234
<212> TYPE: DNA
<213> ORGANISM: Homo sapiens
<220> FEATURE:
<221> NAME/KEY: gene
<222> LOCATION: (1)..(234)
<223> OTHER INFORMATION: D2 domain of human CD4 receptor (nt)

<400> SEQUENCE: 23
accgccaact ccgacaccca tctgctgcag ggccagagcc tgaccctgac actggaaagc      60
cctccaggca gctcccccag cgtgcagtgt agaagccctc ggggcaagaa catccagggc     120
ggcaagacac tgagcgtgtc ccagctggaa ctgcaggaca cgggcacatg gacctgtacc     180
gtgctgcaga accagaaaaa ggtggaattc aagatcgaca tcgtggtgct ggcc           234

<210> SEQ ID NO 24
<211> LENGTH: 696
<212> TYPE: DNA
<213> ORGANISM: Homo sapiens
<220> FEATURE:
<221> NAME/KEY: gene
<222> LOCATION: (1)..(696)
<223> OTHER INFORMATION: Fc portion of human IgG1

<400> SEQUENCE: 24
gagcccaaga gctgcgacaa gacccacacc tgtcccccct tgtcctgccc tgaactgctg      60
ggcggaccta gcgtgttcct gttccccccca aagcccaagg acaccctgat gatctcccgg     120
```

```
acccccgaag tgacctgcgt ggtggtggat gtgtcccacg aggaccctga agtgaagttc    180
aattggtacg tggacggcgt ggaagtgcac aacgccaaga ccaagcccag agaggaacag    240
tacaacagca cctaccgggt ggtgtccgtg ctgaccgtgc tgcaccagga ctggctgaac    300
ggcaaagagt acaagtgcaa ggtgtccaac aaggccctgc ctgcccccat cgagaaaacc    360
atcagcaagg ccaagggcca gccccgcgaa ccccaggtgt acacactgcc ccctagcagg    420
gacgagctga ccaagaacca ggtgtccctg acctgtctcg tgaagggctt ttaccccctcc   480 gatatcgccg tggaatggga gagcaacggc cagcccgaga caactacaa gaccaccccc     540 cctgtgctgg actccgacgg ctcattcttc ctgtacagca aactgaccgt ggacaagagc    600
cggtggcagc agggcaacgt gttcagctgc agcgtgatgc acgaggccct gcacaaccac    660
tacacccaga gtccctgtc cctgagccct ggcaaa                               696

<210> SEQ ID NO 25
<211> LENGTH: 696
<212> TYPE: DNA
<213> ORGANISM: Artificial Sequence
<220> FEATURE:
<223> OTHER INFORMATION: Fc portion of the human IgG1 with G236A, S293D,
      A330L and I332E point mutations (nt)
<220> FEATURE:
<221> NAME/KEY: gene
<222> LOCATION: (1)..(696)
<223> OTHER INFORMATION: Fc portion of the human IgG1 with G236A, S239D,
      A330L and I332E point mutations (nt)

<400> SEQUENCE: 25
gagcccaaga gctgcgacaa gacccacacc tgtcccccctt gtcctgcccc tgaactgctg    60
gccggacccg acgtgttcct gttcccccca aagcccaagg acaccctgat gatctcccgg    120
acccccgaag tgacctgcgt ggtggtggat gtgtcccacg aggaccctga agtgaagttc    180
aattggtacg tggacggcgt ggaagtgcac aacgccaaga ccaagcccag agaggaacag    240
tacaacagca cctaccgggt ggtgtccgtg ctgacagtgc tgcaccagga ctggctgaac    300
ggcaaagagt acaagtgcaa ggtgtccaac aaggccctgc ctctgcccga ggaaaagacc    360
atcagcaagg cccagggcca gcccagggaa ccccaggtgt acacactgcc ccccagcaga    420
gatgagctga ccaagaacca ggtgtccctg acctgtctcg tgaagggctt ttaccccctcc    480 gatatcgccg tggaatggga gagcaacggc cagcccgaga caactacaa gaccaccccc     540 cctgtgctgg actccgacgg ctcattcttc ctgtactcca agctgaccgt ggacaagagc    600
agatggcagc agggcaacgt gttcagctgc tccgtgatgc acgaggccct gcacaaccac    660
tacacccaga gtccctgag cctgagccca ggcaaa                               696

<210> SEQ ID NO 26
<211> LENGTH: 15
<212> TYPE: DNA
<213> ORGANISM: Artificial Sequence
<220> FEATURE:
<223> OTHER INFORMATION: Linker polypeptide (nt)
<220> FEATURE:
<221> NAME/KEY: gene
<222> LOCATION: (1)..(15)
<223> OTHER INFORMATION: Linker polypeptide (nt)

<400> SEQUENCE: 26
ggcggagggg gatct                                                      15

<210> SEQ ID NO 27
```

```
<211> LENGTH: 87
<212> TYPE: DNA
<213> ORGANISM: Homo sapiens
<220> FEATURE:
<221> NAME/KEY: gene
<222> LOCATION: (1)..(87)
<223> OTHER INFORMATION: 5' terminal region of the human CCR5 receptor
      (nt)

<400> SEQUENCE: 27
gattatcagg tgtccagccc catctacgac atcaactact acaccagcga gccctgccag    60
aaaatcaacg tgaagcagat cgccgct                                        87

<210> SEQ ID NO 28
<211> LENGTH: 108
<212> TYPE: DNA
<213> ORGANISM: Human immunodeficiency virus
<220> FEATURE:
<221> NAME/KEY: gene
<222> LOCATION: (1)..(108)
<223> OTHER INFORMATION: T-20 polypeptide (nt)

<400> SEQUENCE: 28
tacacaagcc tgatccacag cctgatcgag gaaagccaga accagcagga aaagaacgag    60
caggaactgc tggaactgga caagtgggcc agcctgtgga attggttc                108

<210> SEQ ID NO 29
<211> LENGTH: 117
<212> TYPE: DNA
<213> ORGANISM: Human immunodeficiency virus
<220> FEATURE:
<221> NAME/KEY: gene
<222> LOCATION: (1)..(117)
<223> OTHER INFORMATION: T-1249 polypeptide (nt)

<400> SEQUENCE: 29
tggcaggaat gggaacagaa aattaccgcg ctgctggaac aggcgcagat tcagcaggaa    60
aaaaacgaat atgaactgca gaaactggat aaatgggcga gcctgtggga atggttt     117

<210> SEQ ID NO 30
<211> LENGTH: 102
<212> TYPE: DNA
<213> ORGANISM: Human immunodeficiency virus
<220> FEATURE:
<221> NAME/KEY: gene
<222> LOCATION: (1)..(102)
<223> OTHER INFORMATION: C34 polypeptide (nt)

<400> SEQUENCE: 30
tggatggaat gggatcgcga aattaacaac tataccagcc tgattcatag cctgattgaa    60
gaaagccaga accagcagga aaaaaacgaa caggaactgc tg                     102

<210> SEQ ID NO 31
<211> LENGTH: 114
<212> TYPE: DNA
<213> ORGANISM: Human immunodeficiency virus
<220> FEATURE:
<221> NAME/KEY: gene
<222> LOCATION: (1)..(114)
<223> OTHER INFORMATION: T-2635 polypeptide (nt)

<400> SEQUENCE: 31
accacctggg aagcgtggga tcgcgcgatt gcggaatatg cggcgcgcat tgaagcgctg    60
attcgcgcgg cgcaggaaca gcaggaaaaa aacgaagcgg cgctgcgcga actg        114
```

<210> SEQ ID NO 32
<211> LENGTH: 1230
<212> TYPE: DNA
<213> ORGANISM: Artificial Sequence
<220> FEATURE:
<223> OTHER INFORMATION: cDNA MOLECULE-0 (nt)
<220> FEATURE:
<221> NAME/KEY: gene
<222> LOCATION: (1)..(1230)
<223> OTHER INFORMATION: cDNA MOLECULE-0 (nt)

<400> SEQUENCE: 32

```
aagaaagtgg tgctgggcaa aaagggcgac accgtggaac tgacctgcac cgccagccag      60
aagaagtcca tccagttcca ctggaagaac agcaaccaga tcaagatcct gggcaaccag     120
ggcagcttcc tgaccaaggg ccccagcaag ctgaacgaca gagccgactc tcggcggagc     180
ctgtgggacc agggcaattt cccactgatc atcaagaacc tgaagatcga ggacagcgac     240
acctacatct gcgaggtgga agatcagaaa gaagaggtgc agctgctggt gttcggcctg     300
accgccaact ccgacaccca tctgctgcag gccagagctc tgaccctgac actgaaaagc     360
cctccaggca gctcccccag cgtgcagtgt agaagccctc ggggcaagaa catccagggc     420
ggcaagacac tgagcgtgtc ccagctggaa ctgcaggaca cggcacatg gacctgtacc      480 gtgctgcaga accagaaaaa ggtggaattc aagatcgaca tcgtggtgct ggccgagccc     540
aagagctgcg acaagaccca cacctgtccc ccttgtcctg ccctgaact gctgggcgga      600 cctagcgtgt tcctgttccc cccaaagccc aaggacaccc tgatgatctc ccggaccccc     660
gaagtgacct gcgtggtggt ggatgtgtcc cacgaggacc ctgaagtgaa gttcaattgg     720
tacgtggacg gcgtggaagt gcacaacgcc aagaccaagc ccagagagga acagtacaac     780
agcacctacc gggtggtgtc cgtgctgacc gtgctgcacc aggactggct gaacggcaaa     840
gagtacaagt gcaaggtgtc caacaaggcc ctgcctgccc ccatcgagaa aaccatcagc     900
aaggccaagg gccagccccg cgaacccag gtgtacacac tgccccctag cagggacgag      960
ctgaccaaga accaggtgtc cctgacctgt ctcgtgaagg gcttttaccc ctccgatatc    1020
gccgtggaat gggagagcaa cggccagccc gagaacaact acaagaccac cccccctgtg    1080
ctggactccg acggctcatt cttcctgtac agcaaactga ccgtggacaa gagccggtgg    1140
cagcagggca cgtgttcag ctgcagcgtg atgcacgagg ccctgcacaa ccactacacc     1200
cagaagtccc tgtccctgag ccctggcaaa                                     1230
```

<210> SEQ ID NO 33
<211> LENGTH: 1374
<212> TYPE: DNA
<213> ORGANISM: Artificial Sequence
<220> FEATURE:
<223> OTHER INFORMATION: cDNA MOLECULE-1 (nt)
<220> FEATURE:
<221> NAME/KEY: gene
<222> LOCATION: (1)..(1374)
<223> OTHER INFORMATION: cDNA MOLECULE-1 (nt)

<400> SEQUENCE: 33

```
atgcctatgg gaagcctgca gcctctggcc accctgtacc tgctgggaat gctggtggcc      60
tccgtgctgg ccaagaaagt ggtgctgggc aaaaagggcg acaccgtgga actgacctgc     120
accgccagcc agaagaagtc catccagttc cactggaaga acagcaacca gatcaagatc     180
ctgggcaacc agggcagctt cctgaccaag ggccccagca agctgaacga cagagccgac     240
tctcggcgga gcctgtggga ccagggcaat ttcccactga tcatcaagaa cctgaagatc     300
```

| | | |
|---|---|---|
| gaggacagcg acacctacat ctgcgaggtg aagatcaga aagaagaggt gcagctgctg | 360 | |
| gtgttcggcc tgaccgccaa ctccgacacc catctgctgc agggccagag cctgaccctg | 420 | |
| acactggaaa gccctccagg cagcagcccc agcgtgcagt gtagaagccc cagaggcaag | 480 | |
| aacatccagg gcggcaagac cctgagcgtg tcccagctgg aactgcagga tagcggcacc | 540 | |
| tggacctgca cagtgctgca gaaccagaaa aaggtggaat tcaagatcga catcgtggtg | 600 | |
| ctggccgctg ccgaccctga gcctaagagc tgcgacaaga cccacacctg tccccttgt | 660 | |
| cctgcccctg aactgctggg cggacctagc gtgttcctgt tccccccaaa gcccaaggac | 720 | |
| accctgatga tctcccggac ccccgaagtg acctgcgtgg tggtggatgt gtcccacgag | 780 | |
| gaccctgaag tgaagttcaa ttggtacgtg gacggcgtgg aagtgcacaa cgccaagacc | 840 | |
| aagcccagag aggaacagta caacagcacc taccgggtgg tgtccgtgct gaccgtgctg | 900 | |
| caccaggact ggctgaacgg caaagagtac aagtgcaagg tgtccaacaa ggccctgcct | 960 | |
| gcccccatcg agaaaaccat cagcaaggcc aagggccagc ccgcgaacc ccaggtgtac | 1020 | |
| acactgcccc ctagcaggga cgagctgacc aagaaccagg tgtccctgac ctgtctcgtg | 1080 | |
| aagggcttt accctccga tatcgccgtg gaatgggaga gcaacggcca gcccgagaac | 1140 | |
| aactacaaga ccacccccc tgtgctggac tccgacggct cattcttcct gtacagcaaa | 1200 | |
| ctgaccgtgg acaagagccg gtggcagcag ggcaacgtgt tcagctgcag cgtgatgcac | 1260 | |
| gaggccctgc acaaccacta cacccagaag tccctgtccc tgagccctgg caaaggcggc | 1320 | |
| ggaggcggag attacgccga ttacgatggc ggctactact acgacatgga ctga | 1374 | |

<210> SEQ ID NO 34
<211> LENGTH: 1374
<212> TYPE: DNA
<213> ORGANISM: Artificial Sequence
<220> FEATURE:
<223> OTHER INFORMATION: cDNA MOLECULE-2 (nt)
<220> FEATURE:
<221> NAME/KEY: gene
<222> LOCATION: (1)..(1374)
<223> OTHER INFORMATION: cDNA MOLECULE-2 (nt)

<400> SEQUENCE: 34

| | | |
|---|---|---|
| atgcctatgg gaagcctgca gcctctggcc accctgtacc tgctgggaat gctggtggcc | 60 | |
| tccgtgctgg ccaagaaagt ggtgctgggc aaaaagggcg acaccgtgga actgacctgc | 120 | |
| accgccagcc agaagaagtc catccagttc cactggaaga acagcaacca gatcaagatc | 180 | |
| ctgggcaaca agggcagctt cctgaccaag ggccccagca agctgaacga cagagccgac | 240 | |
| tctcggcgga gcctgtggga ccagggcaat ttcccactga tcatcaagaa cctgaagatc | 300 | |
| gaggacagcg acacctacat ctgcgaggtg aagatcaga aagaagaggt gcagctgctg | 360 | |
| gtgttcggcc tgaccgccaa ctccgacacc catctgctgc agggccagag cctgaccctg | 420 | |
| acactggaaa gccctccagg cagcagcccc agcgtgcagt gtagaagccc cagaggcaag | 480 | |
| aacatccagg gcggcaagac cctgagcgtg tcccagctgg aactgcagga tagcggcacc | 540 | |
| tggacctgca cagtgctgca gaaccagaaa aaggtggaat tcaagatcga catcgtggtg | 600 | |
| ctggccgctg ccgaccctga gcctaagagc tgcgacaaga cccacacctg tccccttgt | 660 | |
| cctgcccctg aactgctggc cggacccgac gtgttcctgt tccccccaaa gcccaaggac | 720 | |
| accctgatga tctcccggac ccccgaagtg acctgcgtgg tggtggatgt gtcccacgag | 780 | |
| gaccctgaag tgaagttcaa ttggtacgtg gacggcgtgg aagtgcacaa cgccaagacc | 840 | |

| | |
|---|---|
| aagcccagag aggaacagta caacagcacc taccgggtgg tgtccgtgct gaccgtgctg | 900 |
| caccaggact ggctgaacgg caaagagtac aagtgcaagg tgtccaacaa ggccctgcct | 960 |
| ctgcccgagg aaaagaccat cagcaaggcc aagggccagc ccagggaacc ccaggtgtac | 1020 |
| acactgcccc ccagcagaga tgagctgacc aagaaccagg tgtccctgac ctgtctcgtg | 1080 |
| aagggctttt accccctccga tatcgccgtg gaatgggaga gcaacggcca gcccgagaac | 1140 |
| aactacaaga ccaccccccc tgtgctggac tccgacggct cattcttcct gtacagcaaa | 1200 |
| ctgaccgtgg acaagagccg gtggcagcag ggcaacgtgt tcagctgcag cgtgatgcac | 1260 |
| gaggccctgc acaaccacta cacccagaag tccctgtccc tgagccctgg caaaggcggc | 1320 |
| ggaggcggag attacgccga ttacgatggc ggctactact acgacatgga ctga | 1374 |

<210> SEQ ID NO 35
<211> LENGTH: 1437
<212> TYPE: DNA
<213> ORGANISM: Artificial Sequence
<220> FEATURE:
<223> OTHER INFORMATION: cDNA MOLECULE-3 (nt)
<220> FEATURE:
<221> NAME/KEY: gene
<222> LOCATION: (1)..(1437)
<223> OTHER INFORMATION: cDNA MOLECULE-3 (nt)

<400> SEQUENCE: 35

| | |
|---|---|
| atgaatagag gcgtgcccctt ccggcatctg ctgctggtgc tgcagctggc tctgctgcct | 60 |
| gctgccaccc agggcaagaa agtggtgctg ggcaaaaagg gcgacaccgt ggaactgacc | 120 |
| tgcaccgcca gcagaagaa gtccatccag ttcactgga agaacagcaa ccagatcaag | 180 |
| atcctgggca accagggcag cttcctgacc aagggcccca gcaagctgaa cgacagagcc | 240 |
| gactctcggc ggagcctgtg ggaccagggc aatttcccac tgatcatcaa gaacctgaag | 300 |
| atcgaggaca gcgacaccta catctgcgag gtggaagatc agaaagaaga ggtgcagctg | 360 |
| ctggtgttcg gcctgaccgc caactccgac acccatctgc tgcagggcca gagcctgacc | 420 |
| ctgacactgg aaagccctcc aggcagctcc ccagcgtgc agtgtagaag ccctcggggc | 480 |
| aagaacatcc agggcggcaa gacactgagc gtgtcccagc tggaactgca ggacagcggc | 540 |
| acatggacct gtaccgtgct gcagaaccag aaaaaggtgg aattcaagat cgacatcgtg | 600 |
| gtgctggccg agcccaagag ctgcgacaag acccacacct gtcccccttg tcctgccccct | 660 |
| gaactgctgg ccggacccga cgtgttcctg ttcccccccaa agcccaagga caccctgatg | 720 |
| atctcccgga ccccgaagt gacctgcgtg gtggtggatg tgtcccacga ggaccctgaa | 780 |
| gtgaagttca attggtacgt ggacggcgtg gaagtgcaca acgccaagac caagcccaga | 840 |
| gaggaacagt acaacagcac ctaccgggtg gtgtccgtgc tgacagtgct gcaccaggac | 900 |
| tggctgaacg gcaaagagta caagtgcaag gtgtccaaca aggccctgcc tctgcccgag | 960 |
| gaaaagacca tcagcaaggc caagggccag cccagggaac cccaggtgta cacactgccc | 1020 |
| cccagcagag atgagctgac caagaaccag gtgtccctga cctgtctcgt gaagggcttt | 1080 |
| taccccctccg atatcgccgt ggaatgggag agcaacggcc agcccgagaa caactacaag | 1140 |
| accaccccccc ctgtgctgga ctccgacggc tcattcttcc tgtactccaa gctgaccgtg | 1200 |
| gacaagagca gatggcagca gggcaacgtg ttcagctgct ccgtgatgca cgaggccctg | 1260 |
| cacaaccact acacccagaa gtccctgagc ctgagcccag caaaggcgg aggcggagcg | 1320 |
| gccgcgtaca catctctgat ccacagcctg atcgaggaaa gccagaacca gcaggaaaag | 1380 |
| aacgagcagg aactgctgga actggacaag tgggccagcc tgtggaattg gttctga | 1437 |

<210> SEQ ID NO 36
<211> LENGTH: 1407
<212> TYPE: DNA
<213> ORGANISM: Artificial Sequence
<220> FEATURE:
<223> OTHER INFORMATION: cDNA MOLECULE-4 (nt)
<220> FEATURE:
<221> NAME/KEY: gene
<222> LOCATION: (1)..(1407)
<223> OTHER INFORMATION: cDNA MOLECULE-4 (nt)

<400> SEQUENCE: 36

```
atgaatagag gcgtgcccct tccggcatctg ctgctggtgc tgcagctggc tctgctgcct      60
gctgccaccc agggcaagaa agtggtgctg ggcaaaaagg gcgacaccgt ggaactgacc     120
tgcaccgcca gccagaagaa gtccatccag ttccactgga agaacagcaa ccagatcaag     180
atcctgggca accagggcag cttcctgacc aagggcccca gcaagctgaa cgacagagcc     240
gactctcggc ggagcctgtg ggaccagggc aatttcccac tgatcatcaa gaacctgaag     300
atcgaggaca gcgacaccta catctgcgag gtggaagatc agaaagaaga ggtgcagctg     360
ctggtgttcg gcctgaccgc caactccgac acccatctgc tgcagggcca gagcctgacc     420
ctgacactgg aaagccctcc aggcagctcc cccagcgtgc agtgtagaag ccctcggggc     480
aagaacatcc agggcggcaa gacactgagc gtgtcccagc tggaactgca ggacagcggc     540
acatggacct gtaccgtgct gcagaaccag aaaaaggtgg aattcaagat cgacatcgtg     600
gtgctggccg agcccaagag ctgcgacaag acccacacct gtccccttg tcctgcccct     660
gaactgctgg ccggacccga cgtgttcctg ttcccccaa gcccaagga caccctgatg     720
atctcccgga cccccgaagt gacctgcgtg gtggtggatg tgtcccacga ggaccctgaa     780
gtgaagttca attggtacgt ggacggcgtg gaagtgcaca acgccaagac caagcccaga     840
gaggaacagt acaacagcac ctaccgggtg gtgtccgtgc tgaccgtgct gcaccaggac     900
tggctgaacg gcaagagta caagtgcaag gtgtccaaca aggccctgcc tctgcccgag     960
gaaaagacca tcagcaaggc caagggccag ccccagggaaa cccaggtgta cacactgccc    1020
cccagcagag atgagctgac caagaaccag gtgtccctga cctgtctcgt gaagggcttt    1080
taccctccg atatcgccgt ggaatgggag agcaacggcc agcccgagaa caactacaag    1140
accacccccc ctgtgctgga ctccgacggc tcattcttcc tgtactccaa gctgaccgtg    1200
gacaagagca gatggcagca gggcaacgtg ttcagctgct ccgtgatgca cgaggccctg    1260
cacaaccact acacccagaa gtccctgagc ctgagcccag gcaaaggcgg cggaggcgat    1320
tatcaggtgt ccagccccat ctacgacatc aactactaca ccagcgagcc ctgccagaaa    1380
atcaacgtga agcagatcgc cgcctga                                        1407
```

<210> SEQ ID NO 37
<211> LENGTH: 1593
<212> TYPE: DNA
<213> ORGANISM: Artificial Sequence
<220> FEATURE:
<223> OTHER INFORMATION: cDNA MOLECULE-5 (nt)
<220> FEATURE:
<221> NAME/KEY: gene
<222> LOCATION: (1)..(1593)
<223> OTHER INFORMATION: cDNA MOLECULE-5 (nt)

<400> SEQUENCE: 37

```
atgaatagag gcgtgcccct tccggcatctg ctgctggtgc tgcagctggc tctgctgcct      60
```

```
gctgccaccc agggcaagaa agtggtgctg ggcaaaaagg gcgacaccgt ggaactgacc    120
tgcaccgcca gccagaagaa gtccatccag ttccactgga agaacagcaa ccagatcaag    180
atcctgggca accagggcag cttcctgacc aagggcccca gcaagctgaa cgacagagcc    240
gactctcggc ggagcctgtg ggaccagggc aatttcccac tgatcatcaa gaacctgaag    300
atcgaggaca gcgacaccta catctgcgag gtggaagatc agaaagaaga ggtgcagctg    360
ctggtgttcg gcctgaccgc caactccgac acccatctgc tgcagggcca gagcctgacc    420
ctgacactgg aaagccctcc aggcagctcc cccagcgtgc agtgtagaag ccctcggggc    480
aagaacatcc agggcggcaa gacactgagc gtgtcccagc tggaactgca ggacagcggc    540
acatggacct gtaccgtgct gcagaaccag aaaaaggtgg aattcaagat cgacatcgtg    600
gtgctggccg agcccaagag ctgcgacaag acccacacct gtccccttg tcctgccct    660 gaactgctgg ccggacccga cgtgttcctg ttccccccaa agcccaagga caccctgatg    720
atctcccgga cccccgaagt gacctgcgtg gtggtggatg tgtcccacga ggaccctgaa    780
gtgaagttca attggtacgt ggacggcgtg gaagtgcaca acgccaagac caagcccaga    840
gaggaacagt acaacagcac ctaccgggtg gtgtccgtgc tgacagtgct gcaccaggac    900
tggctgaacg gcaaagagta caagtgcaag gtgtccaaca aggccctgcc tctgcccgag    960
gaaaagacca tcagcaaggc caagggccag cccagggaac ccaggtgta cacactgccc    1020 cccagcagag atgagctgac caagaaccag gtgtccctga cctgtctcgt gaagggcttt    1080 taccctccg atatcgccgt ggaatgggag agcaacggcc agcccgagaa caactacaag    1140
accacccccc ctgtgctgga ctccgacggc tcattcttcc tgtactccaa gctgaccgtg    1200
gacaagagca gatggcagca gggcaacgtg ttcagctgct ccgtgatgca cgaggccctg    1260
cacaaccact acacccagaa gtccctgagc ctgagcccag gcaaaggcgg cggaggcgat    1320
tatcaggtgt ccagccccat ctacgacatc aactactaca ccagcgagcc ctgccagaaa    1380
atcaacgtga agcagatcgc cgctggcgga ggggatctg ggggcggagg aagcggaggc    1440
ggaggatcag gcgggggagg ctctggggga ggcggatctt acacaagcct gatccacagc    1500
ctgatcgagg aaagccagaa ccagcaggaa aagaacgagc aggaactgct ggaactggac    1560
aagtgggcca gcctgtggaa ttggttctga tga                                1593
```

<210> SEQ ID NO 38
<211> LENGTH: 1311
<212> TYPE: DNA
<213> ORGANISM: Artificial Sequence
<220> FEATURE:
<223> OTHER INFORMATION: cDNA MOLECULE-6 (nt)
<220> FEATURE:
<221> NAME/KEY: gene
<222> LOCATION: (1)..(1311)
<223> OTHER INFORMATION: cDNA MOLECULE-6 (nt)

<400> SEQUENCE: 38

```
atgaatagag gcgtgcccttt ccggcatctg ctgctggtgc tgcagctggc tctgctgcct    60
gctgccaccc agggcaagaa agtggtgctg ggcaaaaagg gcgacaccgt ggaactgacc    120
tgcaccgcca gccagaagaa gtccatccag ttccactgga agaacagcaa ccagatcaag    180
atcctgggca accagggcag cttcctgacc aagggcccca gcaagctgaa cgacagagcc    240
gactctcggc ggagcctgtg ggaccagggc aatttcccac tgatcatcaa gaacctgaag    300
atcgaggaca gcgacaccta catctgcgag gtggaagatc agaaagaaga ggtgcagctg    360
ctggtgttcg gcctgaccgc caactccgac acccatctgc tgcagggcca gagcctgacc    420
```

```
ctgacactgg aaagccctcc aggcagctcc cccagcgtgc agtgtagaag ccctcggggc    480
aagaacatcc agggcggcaa gacactgagc gtgtcccagc tggaactgca ggacagcggc    540
acatggacct gtaccgtgct gcagaaccag aaaaaggtgg aattcaagat cgacatcgtg    600
gtgctggccg agcccaagag ctgcgacaag acccacacct gtccccttg tcctgccct     660 gaactgctgg ccggacccga cgtgttcctg ttcccccaa agcccaagga caccctgatg    720
atctcccgga cccccgaagt gacctgcgtg gtggtggatg tgtcccacga ggaccctgaa    780
gtgaagttca attggtacgt ggacggcgtg gaagtgcaca cgccaagac caagcccaga    840 gaggaacagt acaacagcac ctaccgggtg gtgtccgtgc tgacagtgct gcaccaggac    900
tggctgaacg gcaaagagta caagtgcaag gtgtccaaca aggccctgcc tctgcccgag    960
gaaaagacca tcagcaaggc caagggccag cccagggaac cccaggtgta cacactgccc   1020
cccagcagag atgagctgac caagaaccag gtgtccctga cctgtctcgt gaagggcttt   1080 taccccctccg atatcgccgt ggaatgggag agcaacggcc agcccgagaa caactacaag   1140
accacccccc ctgtgctgga ctccgacggc tcattcttcc tgtactccaa gctgaccgtg   1200
gacaagagca gatggcagca gggcaacgtg ttcagctgct ccgtgatgca cgaggccctg   1260
cacaaccact acacccagaa gtccctgagc ctgagccccg gcaagtgatg a            1311

<210> SEQ ID NO 39
<211> LENGTH: 1542
<212> TYPE: DNA
<213> ORGANISM: Artificial Sequence
<220> FEATURE:
<223> OTHER INFORMATION: cDNA MOLECULE-7 (nt)
<220> FEATURE:
<221> NAME/KEY: gene
<222> LOCATION: (1)..(1542)
<223> OTHER INFORMATION: cDNA MOLECULE-7 (nt)

<400> SEQUENCE: 39
atgtggctgc agtctctgct gctgctgggc accgtggcct gcagcatcag caagaaagtg     60
gtgctgggca agaaaggcga caccgtggaa ctgacctgca ccgccagcca gaagaagtcc    120
atccagttcc actggaagaa cagcaaccag atcaagatcc tggcaaccca gggcagcttc    180
ctgaccaagg cccccagcaa gctgaacgac agagccgact ctcggcggag cctgtgggac    240
cagggcaatt tccactgat catcaagaac ctgaagatcg aggacagcga cacctacatc    300
tgcgaggtgg aagatcagaa agaagaggtg cagctgctgg tgttcggcct gaccgccaac    360
tccgacaccc atctgctgca gggccagagc ctgaccctga cactggaaag ccctccaggc    420
agcagcccca gcgtgcagtg tagaagcccc agaggcaaga acatccaggg cggcaagacc    480
ctgagcgtgt cccagctgga actgcaggat agcggcacct ggacctgtac cgtgctgcag    540
aaccagaaaa aggtggaatt caagatcgac atcgtggtgc tggccgagcc caagagctgc    600
gacaagaccc acacctgtcc ccttgtcct gcccctgaac tgctggccgg acccgacgtg    660
ttcctgttcc cccaaagcc caaggacacc ctgatgatct cccggacccc cgaagtgacc    720
tgcgtggtgg tggatgtgtc ccacgaggac cctgaagtga agttcaattg gtacgtggac    780
ggcgtggaag tgcacaacgc caagaccaag cccagagagg aacagtacaa cagcacctac    840
cgggtggtgt ccgtgctgac agtgctgcac caggactggc tgaacggcaa agagtacaag    900
tgcaaggtgt ccaacaaggc cctgcctctg cccgagaaa agaccatctc caaggccaag    960
ggccagccca gggaaccca ggtgtacaca ctgcccccca gcagagatga gctgaccaag   1020
```

```
aaccaggtgt ccctgacctg tctcgtgaag gcttttacc cctccgatat cgccgtggaa    1080
tgggagagca acggccagcc cgagaacaac tacaagacca cccccctgt gctggactcc    1140 gacggctcat tcttcctgta ctccaagctg accgtggaca agagccggtg gcagcagggc   1200
aacgtgttca gctgcagcgt gatgcacgag gccctgcaca accactacac ccagaagtcc   1260
ctgagcctga gcccaggcaa aggcggcgga ggatctggcg gaggcggatc tggggcgga   1320 ggaagtgggg gaggggaag cggagggga ggctcaggcg gggaggaag cggaggcggg   1380 ggaagtggcg gcggaggcag tggcgggga ggctccgggg gaggcggctc ttatacaagc   1440
ctgatccaca gcctgatcga ggaaagccag aaccagcagg aaaagaacga gcaggaactg   1500
ctggaactgg acaagtgggc cagcctgtgg aattggttct ga                     1542
```

<210> SEQ ID NO 40
<211> LENGTH: 1452
<212> TYPE: DNA
<213> ORGANISM: Artificial Sequence
<220> FEATURE:
<223> OTHER INFORMATION: cDNA MOLECULE-8 (nt)
<220> FEATURE:
<221> NAME/KEY: gene
<222> LOCATION: (1)..(1452)
<223> OTHER INFORMATION: cDNA MOLECULE-8 (nt)

<400> SEQUENCE: 40

```
atgtggctgc agtctctgct gctgctgggc accgtggcct gcagcatcag caagaaagtg     60
gtgctgggca agaaaggcga caccgtggaa ctgacctgca ccgccagcca gaagaagtcc    120
atccagttcc actggaagaa cagcaaccag atcaagatcc tggcaaccca gggcagcttc    180
ctgaccaagg gccccagcaa gctgaacgac agagccgact ctcggcggag cctgtgggac    240
cagggcaatt tcccactgat catcaagaac ctgaagatcg aggacagcga cacctacatc    300
tgcgaggtgg aagatcagaa agaagaggtg cagctgctgg tgttcggcct gaccgccaac    360
tccgacaccc atctgctgca gggccagagc ctgaccctga cactggaaag ccctccaggc    420
agcagcccca gcgtgcagtg tagaagcccc agaggcaaga acatccaggg cggcaagacc    480
ctgagcgtgt cccagctgga actgcaggat agcggcacct ggacctgtac cgtgctgcag    540
aaccagaaaa aggtggaatt caagatcgac atcgtggtgc tggccgagcc caagagctgc    600
gacaagaccc acacctgtcc cccttgtcct gcccctgaac tgctggccgg acccgacgtg    660
ttcctgttcc cccaaagcc caaggacacc ctgatgatct cccggacccc cgaagtgacc    720
tgcgtggtgg tggatgtgtc ccacgaggac cctgaagtga agttcaattg gtacgtggac   780
ggcgtggaag tgcacaacgc caagaccaag cccagagagg aacagtacaa cagcacctac   840
cgggtggtgt ccgtgctgac agtgctgcac caggactggc tgaacggcaa agagtacaag   900
tgcaaggtgt ccaacaaggc cctgcctctg cccgaggaaa agaccatctc caaggccaag   960
ggccagccca gggaacccca ggtgtacaca ctgccccca gcagagatga gctgaccaag   1020
aaccaggtgt ccctgacctg tctcgtgaag gcttttacc cctccgatat cgccgtggaa   1080
tgggagagca acggccagcc cgagaacaac tacaagacca cccccctgt gctggactcc   1140 gacggctcat tcttcctgta ctccaagctg accgtggaca agagccggtg gcagcagggc   1200
aacgtgttca gctgcagcgt gatgcacgag gccctgcaca accactacac ccagaagtcc   1260
ctgagcctga gcccaggcaa aggcggcgga ggatctggcg gaggcggatc tggggcgga   1320 ggaagtgggg gggaggctc ttacacaagc ctgatccaca gcctgatcga ggaaagccag   1380
aaccagcagg aaaagaacga gcaggaactg ctggaactgg acaagtgggc cagcctgtgg   1440
```
aattggttct ga                                                          1452

<210> SEQ ID NO 41
<211> LENGTH: 1503
<212> TYPE: DNA
<213> ORGANISM: Artificial Sequence
<220> FEATURE:
<223> OTHER INFORMATION: cDNA MOLECULE-10 (nt)
<220> FEATURE:
<221> NAME/KEY: gene
<222> LOCATION: (1)..(1503)
<223> OTHER INFORMATION: cDNA MOLECULE-10 (nt)

<400> SEQUENCE: 41
atgtggctgc agtctctgct gctgctgggc accgtggcct gcagcatcag caagaaagtg      60
gtgctgggca agaaaggcga caccgtggaa ctgacctgca ccgccagcca gaagaagtcc     120
atccagttcc actggaagaa cagcaaccag atcaagatcc tgggcaacca gggcagcttc     180
ctgaccaagg cccccagcaa gctgaacgac agagccgact ctcggcggag cctgtgggac     240
cagggcaatt tcccactgat catcaagaac ctgaagatcg aggacagcga cacctacatc     300
tgcgaggtgg aagatcagaa agaagaggtg cagctgctgg tgttcggcct gaccgccaac     360
tccgacaccc atctgctgca gggccagagc ctgacactga cactggaaag ccctccaggc     420
agcagcccca gcgtgcagtg tagaagcccc agaggcaaga acatccaggg cggcaagacc     480
ctgagcgtgt cccagctgga actgcaggat agcggcacct ggacctgtac cgtgctgcag     540
aaccagaaaa aggtggaatt caagatcgac atcgtggtgc tggccgagcc caagagctgc     600
gacaagaccc acacctgtcc cccttgtcct gcccctgaac tgctggccgg acccgacgtg     660
ttcctgttcc ccccaaagcc caaggacacc ctgatgatct cccggacccc cgaagtgacc     720
tgcgtggtgg tggatgtgtc ccacgaggac cctgaagtga agttcaattg gtacgtggac     780
ggcgtggaag tgcacaacgc caagaccaag cccagagagg aacagtacaa cagcacctac     840
cgggtggtgt ccgtgctgac agtgctgcac caggactggc tgaacggcaa agagtacaag     900
tgcaaggtgt ccaacaaggc cctgcctctg cccgaggaaa agaccatctc caaggccaag     960
ggccagccca gggaacccca ggtgtacaca ctgcccccca gcagagatga gctgaccaag    1020
aaccaggtgt ccctgacctg tctcgtgaag ggcttttacc cctccgatat cgccgtggaa    1080
tgggagagca acggccagcc cgagaacaac tacaagacca ccccccctgt gctggactcc    1140
gacggctcat tcttcctgta ctccaagctg accgtggaca gagccggtg gcagcagggc     1200
aacgtgttca gctgcagcgt gatgcacgag gccctgcaca accactacac ccagaagtcc    1260
ctgagcctga gcccaggcaa aggcggcgga ggcgattatc aggtgtccag ccccatctac    1320
gacatcaact actacaccag cgagccctgc agaaaatca acgtgaagca gatcgccgct    1380
ggcggagggg gctacacatc tctgatccac agcctgatcg aggaaagcca gaaccagcag    1440
gaaaagaacg agcaggaact gctggaactg gacaagtggg ccagcctgtg gaattggttc    1500
tga                                                                  1503

<210> SEQ ID NO 42
<211> LENGTH: 1626
<212> TYPE: DNA
<213> ORGANISM: Artificial Sequence
<220> FEATURE:
<223> OTHER INFORMATION: cDNA MOLECULE-11 (nt)
<220> FEATURE:
<221> NAME/KEY: gene
<222> LOCATION: (1)..(1626)

```
<223> OTHER INFORMATION: cDNA MOLECULE-11 (nt)

<400> SEQUENCE: 42
atgtggctgc agtctctgct gctgctgggc accgtggcct gcagcatcag caagaaagtg       60
gtgctgggca agaaaggcga caccgtggaa ctgacctgca ccgccagcca gaagaagtcc      120
atccagttcc actggaagaa cagcaaccag atcaagatcc tgggcaacca gggcagcttc      180
ctgaccaagg gccccagcaa gctgaacgac agagccgact ctcggcggag cctgtgggac      240
cagggcaatt tcccactgat catcaagaac ctgaagatcg aggacagcga cacctacatc      300
tgcgaggtgg aagatcagaa agaagaggtg cagctgctgg tgttcggcct gaccgccaac      360
tccgacaccc atctgctgca gggccagagc ctgaccctga cactggaaag ccctccaggc      420
agcagcccca gcgtgcagtg tagaagcccc agaggcaaga acatccaggg cggcaagacc      480
ctgagcgtgt cccagctgga actgcaggat agcggcacct ggacctgtac cgtgctgcag      540
aaccagaaaa aggtggaatt caagatcgac atcgtggtgc tggccgagcc caagagctgc      600
gacaagaccc acacctgtcc cccttgtcct gcccctgaac tgctggccgg acccgacgtg      660
ttcctgttcc ccccaaagcc caaggacacc ctgatgatct cccggacccc cgaagtgacc      720
tgcgtggtgg tggatgtgtc ccacgaggac cctgaagtga agttcaattg gtacgtggac      780
ggcgtggaag tgcacaacgc caagaccaag cccagagagg aacagtacaa cagcacctac      840
cgggtggtgt ccgtgctgac agtgctgcac caggactggc tgaacggcaa agagtacaag      900
tgcaaggtgt ccaacaaggc cctgcctctg cccgaggaaa agaccatctc caaggccaag      960
ggccagccca gggaacccca ggtgtacaca ctgcccccca gcagagatga gctgaccaag     1020
aaccaggtgt ccctgacctg tctcgtgaag ggcttttacc cctccgatat cgccgtggaa     1080
tgggagagca acggccagcc cgagaacaac tacaagacca ccccccctgt gctggactcc     1140
gacggctcat tcttcctgta ctccaagctg accgtggaca gagccggtg gcagcagggc     1200 aacgtgttca gctgcagcgt gatgcacgag gccctgcaca accactacac ccagaagtcc     1260
ctgagcctga gcccaggcaa aggcggcgga ggcgattatc aggtgtccag ccccatctac     1320
gacatcaact actacaccag cgagccctgc cagaaaatca acgtgaagca gatcgccgct     1380
ggcggagggg gatctggggg cggaggaagc ggaggcggag gatcaggcgg gggaggctct     1440
gggggaggcg gcagtggggg gggaggaagt ggcggaggcg gctcaggcgg aggcggaagc     1500
gggggaggcg gatcttacac aagcctgatc cacagcctga tcgaggaaag ccagaaccag     1560
caggaaaaga acgagcagga actgctggaa ctggacaagt gggccagcct gtggaattgg     1620
ttctga                                                                1626
```